(12) United States Patent  
Armstrong et al.

(10) Patent No.: US 7,858,370 B2
(45) Date of Patent: Dec. 28, 2010

(54) COMPOSITIONS FOR ENHANCING SEGREGATION OF TRANSGENES IN PLANTS

(75) Inventors: Toni Armstrong, St. Louis, MO (US); Kenneth Barton, Chesterfield, MO (US); Laura J. Crow, Middleton, WI (US); Larry A. Gilbertson, Chesterfield, MO (US); Shihshieh Huang, Stonington, CT (US); Yong Huang, Oakland, FL (US); Brian J. Martinell, Mount Horeb, WI (US); Michael W. Petersen, Hillpoint, WI (US); Kenneth J. Piller, Davidson, NC (US); Qi Wang, St. Louis, MO (US); Xudong Ye, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 550 days.

(21) Appl. No.: 11/856,978

(22) Filed: Sep. 18, 2007

(65) Prior Publication Data
US 2008/0064866 A1 Mar. 13, 2008

Related U.S. Application Data

(62) Division of application No. 10/190,217, filed on Jul. 5, 2002, now Pat. No. 7,288,694.

(60) Provisional application No. 60/303,375, filed on Jul. 6, 2001.

(51) Int. Cl.
*C12N 15/82* (2006.01)

(52) U.S. Cl. .................................. 435/320.1

(58) Field of Classification Search .................. None
See application file for complete search history.

(56) References Cited

U.S. PATENT DOCUMENTS

| 5,627,061 A | 5/1997 | Barry et al. |
| 5,731,179 A | 3/1998 | Komari et al. |
| 6,521,458 B1 | 2/2003 | Gutterson et al. |

(Continued)

FOREIGN PATENT DOCUMENTS

WO  WO9204454  3/1992

(Continued)

OTHER PUBLICATIONS

Lu et al 2001, Australian Journal of Plant Physiology 28: 241-248.*

(Continued)

*Primary Examiner*—David H Kruse
(74) *Attorney, Agent, or Firm*—Thompson Coburn LLP; Charles P. Romano

(57) ABSTRACT

The compositions and methods are provided that enhance the selection of transgenic plants having two T-DNA molecules integrated into a plant genome at different physical and genetic loci. The compositions are DNA constructs that comprise novel arrangements of T-DNA molecules containing genes of interest, positive selectable marker genes, and conditional lethal genes. The methods disclosed herein comprises transforming a plant cell to comprise the DNA constructs of the present invention, regenerating the plant cell into a plant and identifying independent transgene loci, where the selectable marker genes or transgenic elements can be segregated in the progeny.

9 Claims, 26 Drawing Sheets

U.S. PATENT DOCUMENTS

2002/0157129 A1    10/2002    Perez et al.

FOREIGN PATENT DOCUMENTS

| WO | WO9839462 | 9/1998 |
| WO | WO0037060 | 6/2000 |
| WO | WO0196583 | 12/2001 |

OTHER PUBLICATIONS

Huang et al 2004, Transgenic Research 13: 451-461.*

Dotson, Stanton, et al., A phosphonate monoester hydrolase from Burkholderia caryophilli PG2982 is useful as a conditional lethal gene in plants, The Plant Journal, 1996, 383-392, vol. 10 No. 2.

Dotson, Stanton, et al., Identification, Characterization, and Cloning of a Phosphonate Monoester Hydrolase from Burkholderia caryophilli PG2982, The Journal of Biological Chemistry, 1996, 25754-25761, vol. 271 No. 42.

Ebinuma, Hiroyasu, et al., Selection of marker-free transgenic plants using the isopentenyl transferase gene, Proceedings of the National Academy of Sciences USA, 1997, 2117-2121, vol. 94.

Ellstrand, Norman, et al., Hybridization as an Avenue of Escape for Engineered Genes, Bioscience, 1990, 438-442, vol. 40 No. 6.

Gleave, Andrew, et al., Selectable marker-free transgenic plants without sexual crossing: transient expression of cre recombinase and use of a conditional lethal dominant gene, Plant Molecular Biology, 1999, 223-235, vol. 40.

Hanson, Bill, et al., A simple method to enrich an Agrobacterium-transformed population for plants containing only T-DNA sequences, The Plant Journal, 1999, 727-734, vol. 19 No. 6.

Huang, Shihshieh, et al., Generation of marker-free transgenic maize by regular two-border Agrobacterium transformation vectors, Transgenic Research, 2004, 451-461, vol. 13.

Komari, Toshihiko, et al., Vectors carrying two separate T-DNAs for co-transformation of higher plants mediated by Agrobacterium tumefaciens and segregation of transformants free from selection markers, The Plant Journal, 1996, 165-174, vol. 10 No. 1.

Kononov, Maria, et al., Integration of T-DNA binary vector 'backbone' sequences into the tobacco genome: evidence for multiple complex patterns of integration, The Plant Journal, 1997, 945-957, vol. 11 No. 5.

Matthews, Peters, et al., Marker gene elimination from transgenic barley, using co-transformation with adjacent 'twin T-DNAs' on a standard Agrobacterium transformation vector, Molecular Breeding, 2001, 195-202, vol. 7.

McCormac, Alex, et al., Efficient co-transformation of Nicotiana tabacum by two independent T-DNAs, the effect of T-DNA size and implications for genetic separation, Transgenic Research, 2001, 143-155, vol. 10.

Miller, Michael, et al., High efficiency transgene segregation in co-transformed maize plants using an Agrobacterium tumefaciens 2 T-DNA binary system, Transgenic Research, 2002, 381-392, Vol. 11.

O'Keefe, Daniel, et al., Plant Expression of a Bacterial Cytochrome P450 That Catalyzes Activation of a Sulfonylurea Pro-Herbicide, Plant Physiology, 1994, 473-482, vol. 105.

International Search Report for PCT/US2002/021350 dated Feb. 4, 2003.

Rommens, Caius, et al., Crop Improvement through Modification of the Plant's Own Genome, Plant Physiology, 2004, 421-431, vol. 135.

Xing, Aiqiu, et al., The Use of the Two T-DNA Binary System to Derive Marker-Free Transgenic Soybeans, In Vitro Cellular and Developmental Biology, 2000, 456-463, vol. 36.

Yoder, John, et al., Transformation Systems for Generating Marker-Free Transgenic Plants, Bio/Technology, 1994, 263-267, vol. 12.

Depicker, Ann et al., Frequencies of simultaneous transformation with different T-DNAs and their relevance to the Agrobacterium/plant cell interaction, Molecular Genetics and Genomics, 1985, pp. 477-484, vol. 201.

Ramanathan, Vai. et al., Transfer of non-T-DNA portions of the Agrobacterium tumefaciens Ti plasmid pTiA6 from the left terminus of TL-DNA, Plant Molecular Biology, 1995, pp. 1149-1154, vol. 28 No. 6.

Wang, Kan et al., Sequence context of the T-DNA border repeat element determines its relative activity during T-DNA transfer to plant cells, Molecular Genetics and Genomics, 1987, pp. 338-346, vol. 210.

Martineau, Belinda et al., Letter to the Editor On Defining T-DNA, The Plant Cell, Aug. 1994, pp. 1032-1033, vol. 6.

* cited by examiner

SEQUENCE LISTING

<160> NUMBER OF SEQ ID NOS: 3

<210> SEQ ID NO 1
<211> LENGTH: 1542
<212> TYPE: DNA
<213> ORGANISM: Pseudomonas caryophilli PG2982

<400> SEQUENCE: 1

```
atggccagaa aaaatgtcct gcttatcgtc gttgatcaat ggcgagcaga tttatccct      60 cacctgatgc gggcggaggg gcgcgaacct ttccttaaaa ctcccaatct tgatcgtctt    120
tgccgggaag gcttgacctt ccgcaatcat gtcacgacgt gcgtgccgtg tggtccggca    180
agggcaagcc tgctgacggg cctctacctg atgaaccacc gggcggtgca gaacactgtt    240
ccgcttgacc agcgccatct aaaccttggc aaggccctgc gcgccattgg ctacgatccc    300
gcgctcattg gttacaccac cacgacacct gatccgcgca caacctctgc aagggatccg    360
cgtttcacgg tcctgggcga catcatggac ggctttcgtt cggtcggcgc attcgagccc    420
aatatggagg ggtattttgg ctgggtggcg cagaacggct tcgaactgcc agagaaccgc    480
gaagatatct ggctgccgga aggtgaacat tccgttcccg gtgctaccga caaaccgtcg    540
cgcattccga aggaatttc ggattcgaca ttcttcacgg agcgcgccct gacatatctg    600
aagggcaggg acggcaagcc tttcttcctg catcttggct attatcgccc gcatccgcct    660
```

-continued

```
ttcgtagcct ccgcgccta ccatgcgatg tacaaagccg aagatatgcc tgcgcctata      720
cgtgcggaga atccggatgc cgaagcggca cagcatccgc tcatgaagca ctatatcgac      780
cacatcagac gcggctcgtt cttccatggc gcggaaggct cgggagcaac gcttgatgaa      840
ggcgaaattc gccagatgcg cgctacatat tgcggactga tcaccgagat cgacgattgt      900
ctggggaggg tctttgccta tctcgatgaa accggtcagt gggacgacac gctgattatc      960
ttcacgagcg atcatggcga acaactgggc gatcatcacc tgctcggcaa gatcggttac     1020
aatgccgaaa gcttccgtat tcccttggtc ataaaggatg cgggacagaa ccggcacgcc     1080
ggccagatcg aagaaggctt ctccgaaagc atcgacgtca tgccgaccat cctcgaatgg     1140
ctgggcgggg aaacgcctcg cgcctgcgac ggccgttcgc tgttgccgtt tctggctgag     1200
ggaaagccct ccgactggcg cacggaacta cattacgagt tcgattttcg cgatgatgtc     1260
ttctacgatc agccgcagaa ctcggtccag ctttcccagg atgattgcag cctctgtgtg     1320
atcgaggagc aaactacaag tacgtgcatt ttgcccgcct gccgccgctg ttcttcgatc     1380
tgaaggcaga cccgcatgaa ttcagcaatc tggctggcga tcctgcttat gcggccctcg     1440
ttcgtgacta tgcccagaag gcattgtcgt ggcgactgtc tcatgccgac cggacactca     1500
cccattacag atccagcccg caactggaca acgcgcaacc at                        1542
```

<210> SEQ ID NO 2
<211> LENGTH: 1542
<212> TYPE: DNA
<213> ORGANISM: Pseudomonas caryophilli PG2982

<400> SEQUENCE: 2

```
atggccagaa aaatgtcct gcttatcgtc gttgatcaat ggcgagcaga ttttatccct       60
cacctgatgc gggcggaggg gcgcgaacct ttccttaaaa ctcccaatct tgatcgtctt      120
tgccgggaag gcttgacctt ccgcaatcat gtcacgacgt gcgtgccgtg tggtccggca      180
agggcaagcc tgctgacggg cctctacctg atgaaccacc gggcggtgca gaacactgtt      240
ccgcttgacc agcgccatct aaaccttggc aaggccctgc gcgccattgg ctacgatccc      300
gcgctcattg gttacaccac cacgacacct gatccgcgca aacctctgc aagagatccg      360
cgtttcacgg tcctgggcga catcatggac ggctttcgtt cggtcggcgc attcgagccc      420
aatatggagg ggtatttttgg ctgggtggcg cagaacggct cgaactgcc agagaaccgc      480
gaagatatct ggctgccgga aggtgaacat tccgttcccg gtgctaccga caaaccgtcg     540
cgcattccga aggaatttc ggattcgaca ttcttcacgg agcgcgcct gacatatctg      600
aagggcaggg acggcaagcc tttcttcctg catcttggct attatcgccc gcatccgcct     660
ttcgtagcct ccgcgccta ccatgcgatg tacaaagccg aagatatgcc tgcgcctata      720
cgtgcggaga atccggatgc cgaagcggca cagcatccgc tcatgaagca ctatatcgac      780
cacatcagac gcggctcgtt ctttcatggt gcggaaggct cgggagcaac gcttgatgaa      840
ggcgaaattc gccagatgcg cgctacatat tgcggactga tcaccgagat cgacgattgt      900
ctggggaggg tctttgccta tctcgatgaa accggtcagt gggacgacac gctgattatc      960
ttcacgagcg atcatggcga acaactgggc gatcatcacc tgctcggcaa gatcggttac     1020
aatgccgaga gcttccgtat tcccttggtc ataaaggatg cgggacagaa ccggcacgcc     1080
ggccagatcg aagaaggctt ctccgaaagc atcgacgtca tgccgaccat cctcgaatgg     1140
ctgggcgggg aaacgcctcg cgcctgcgac ggccgttcgc tgttgccgtt tctggctgag     1200
ggaaagccct ccgactggcg cacggaacta cattacgagt tcgattttcg cgatgtcttc     1260
```

-continued

```
tacgatcagc cgcagaactc ggtccagctt tcccaggatg attgcagcct ctgtgtgatc    1320
gaggacgaaa actacaagta cgtgcatttt gccgccctgc cgccgctgtt cttcgatctg    1380
aaggcagacc cgcatgagtt cagcaatctg gctggcgatc ctgcttatgc ggccctcgtt    1440
cgtgactatg cccagaaggc attgtcgtgg cgactgtctc atgccgaccg gacactcacc    1500
cattacagat ccagcccgca agggctgaca acgcgcaacc at                      1542
```

<210> SEQ ID NO 3
<211> LENGTH: 1293
<212> TYPE: DNA
<213> ORGANISM: Agrobacterium tumefaciens

<400> SEQUENCE: 3

```
atgcttgaga accacaagaa ggttggtatc gctggagctg gaatcgttgg tgtttgcact      60
gctttgatgc ttcaacgtcg tggattcaag gttaccttga ttgatccaaa cccaccaggt     120
gaaggtgctt ctttcggtaa cgctggttgc ttcaacggtt cctccgttgt tccaatgtcc     180
atgccaggaa acttgactag cgttccaaag tggcttcttg acccaatggg tccattgtcc     240
atccgtttca gctactttcc aaccatcatg ccttggttga ttcgtttctt gcttgctgga     300
agaccaaaca aggtgaagga gcaagctaag gcactccgta acctcatcaa gtccactgtg     360
cctttgatca agtccttggc tgaggaggct gatgctagcc accttatccg tcacgaaggt     420
caccttaccg tgtaccgtgg agaagcagac ttcgccaagg accgtggagg ttgggaactt     480
cgtcgtctca acggtgttcg tactcaaatc ctcagcgctg atgcattgcg tgatttcgat     540
cctaacttgt ctcacgcctt taccaaggga atccttatcg aagagaacgg tcacaccatc     600
aacccacaag gtctcgtgac tctcttgttt cgtcgtttca tcgctaacgg tggagagttc     660
gtgtctgctc gtgttatcgg attcgagact gaaggtcgtg ctctcaaggg tatcaccacc     720
accaacggtg ttcttgctgt tgatgcagct gttgttgcag ctggtgcaca ctccaagtct     780
cttgctaact cccttggtga tgacatccca ttggataccg aacgtggata ccacatcgtg     840
atcgccaacc cagaagctgc tccacgtatt ccaactaccg atgcttctgg aaagttcatc     900
gctactccta tggagatggg tcttcgtgtt gctggaaccg ttgagttcgc tggtctcact     960
gctgctccta actggaagcg tgctcacgtt ctctacactc acgctcgtaa gttgcttcca    1020
gctctcgctc ctgccagttc tgaagaacgt tactccaagt ggatgggttt ccgtccaagc    1080
atcccagatt cccttccagt gattggtcgt gctacccgta ctccagacgt tatctacgct    1140
ttcggtcacg gtcacctcgg tatgactggt gctccaatga ccgcaaccct cgtttctgag    1200
ctcctcgcag gtgagaagac ctctatcgac atctctccat tcgcaccaaa ccgtttcggt    1260
attggtaagt ccaagcaaac tggtcctgca tcc                                1293
```

COMPOSITIONS FOR ENHANCING SEGREGATION OF TRANSGENES IN PLANTS

This application is a divisional application of U.S. patent application Ser. No. 10/190,217, filed on Jul. 5, 2002, now U.S. Pat. No. 7,288,694, which claims benefit of U.S. Provisional Application Ser. No. 60/303,375, filed on Jul. 6, 2001.

FIELD OF THE INVENTION

The present invention relates to the field of plant genetic engineering. Particularly, the invention relates to DNA constructs and methods that enhance the segregation of transgenes in plants.

BACKGROUND OF THE INVENTION

The methods for introducing transgenes in plants by *Agrobacterium* mediated transformation utilizes a T-DNA (transfer DNA) that incorporates the genetic elements of the transgene and transfers those genetic elements into the genome of a plant. Generally, the transgene(s) bordered by a right border DNA molecule (RB) and a left border DNA molecule (LB) is transferred into the plant genome at a single locus. It has been previously observed that when a DNA construct contains more than one T-DNA these T-DNAs and the transgenes contained within may be integrated into the plant genome at separate loci and is referred to a co-transformation (U.S. Pat. No. 5,731,179, WO 00/18939). The process of co-transformation, where two T-DNAs are at different loci in the plant genome and therefore segregate independently in the progeny, can be achieved by delivery of the T-DNAs with a mixture of Agrobacteria transformed with plasmids carrying the separate T-DNA (Depicker et al., Mol. Gen. Genet. 201:477-484, 1985; Petit et al., Mol. Gen. Genet. 202:388-393, 1986; McKnight et al., Plant Mol. Biol. 8:439-445, 1987; DeBlock et al., Theor. Appl. Genet. 82:257-263, 1991; Komari et al., Plant J. 10: 165-174, 1996; De Neve et al., Plant J. 11: 15-29, 1997; Poirier et al., Theor. Appl. Genet. 100:487-493, 2000, herein incorporated by reference in their entirety). Co-transformation can also be achieved by transforming one *Agrobacterium* strain with two binary DNA constructs, each containing one T-DNA (Daley et al., Plant Cell Reports 17:489-496 1998). An additional method employs constructing the two T-DNAs on a single DNA vector, transforming the vector into a plant cell and then identifying the transgenic cells or plants that have integrated the T-DNAs at different loci (U.S. Pat. No. 5,731,179, WO 00/18939, Komari et al., Plant J. 10: 165-174, 1996; Xing et al., In Vitro Cell Devel. Biol. Plant 36:456-463, 2000).

Unlinking T-DNAs that contain different plant expression cassettes can be useful in the development of transgenic plants, especially if one of the plant expression cassettes does not contribute to an agronomically useful trait introduced into the crop plant. It has been previously observed that *Agrobacterium* Ti plasmid T-DNAs can insert into the genome of a transformed plant at more than one loci and will segregate in the progeny of the plant (Framond et al., Mol. Gen. Genet. 202:125-131, 1986). The identification of unnecessary or unwanted transgene DNA in transformed plants has been the subject of numerous investigations and many different methods have been examined in efforts to eliminate these transgenes or vector DNA from the plants (Hanson et al., Plant J. 19:727-734, 1999; Dale et al., Proc. Natl. Acad. Sci. 88:10558-10562, 1991; Ebinuma et al., Proc. Natl. Acad. Sci. 94:2117-2121, 1997; Yoder et al., Bio/Technology 12:263-268, 1994; Kononov et al., Plant J. 11:945-957, 1997).

A two T-DNA system is a useful method to segregate the marker gene from the agronomically important gene of interest (GOI) in a transgenic plant. The marker gene generally has no further utility after it has been used to select or score for the transformed plant cell. The research effort to develop an efficient two T-DNA system that provides separate and distinct genomic integration sites has been extensive. A single DNA vector carrying the two-T-DNAs is the preferred method to construct a two T-DNA transformation system. However, because of the occurrence of both T-DNAs on a single DNA construct often both are transferred into the plant genome at the same loci. This occurs when one of the border DNA molecule of the first T-DNA is not recognized during the integration process. This reduced efficiency adds to the cost of producing the events and selecting for the individuals that have T-DNAs integrated at an independent locus. It would be of general utility to have DNA constructs and a method where it is possible to chemically select against individuals that have incorporated the two T-DNAs at the same loci or have incorporated unnecessary DNA that occurs in the spacer region between the two T-DNAs, or unnecessary DNA that occurs in the region of the DNA construct flanking the two T-DNAs.

Heterologous dominant conditional lethal genes have the greatest potential for controlled cell lethality. The genes are by definition, non-lethal in the absence of the controlled application of a heterologous protoxin and utilize protoxins which are not substrates for normal cellular enzymes. In plants, some examples of heterologous conditional lethal genes are the pehA gene that converts a nontoxic phosphonate of glyphosate into glyphosate (U.S. Pat. No. 5,254,801, the entirety of which is herein incorporated by reference), argE gene that converts a nontoxic N-acetyl-phosphinothricin to toxic phosphinothricin (Kriete et al. Plant J. 9:809-818, 1996, the entirety of which is herein incorporated by reference), the iaaH gene encoding indoleacetamide hydrolase which can convert non-toxic levels of naphthalene acetamide into toxic levels of the auxin, naphthalene acetic acid (Klee et al., Genes Dev. 1:86-96, 1987). A bacterial cytosine deaminase gene has been shown to function as a conditional lethal gene for negative selection in plants (Kobayashi et al. Jpn. J. Genet. 70:409-422; Perera et al. Plant Mol. Biol. 23:793-799, 1993, the entirety of which is herein incorporated by reference). P450 monooxygenase expression in plant cells converts a sulphonylurea compound (R7402) with low toxicity into a more highly phytotoxic form (O'Keefe et al. Plant Physiol. 105: 473-482, 1994, the entirety of which is herein incorporated by reference). Transgenic plants expressing β-glucuronidase in male tissues can convert a glucuronic acid conjugated protoxin into a phytotoxic molecule providing a gametocide (WO9204454, the entirety of which is herein incorporated by reference). Viral thymidine kinase is an example of a heterologous dominant conditional lethal gene in mammalian cells the functions in plants (Czako et al. Plant Physiol. 104:1067-1071, 1994). Unlike the cellular thymidine kinase, the viral thymidine kinase protein is able to activate pyrimidine analogs such as acycolvir and gancyclovia into toxic products. The most effective conditional lethal gene enzymes have no affect on cellular metabolism in the absence of the protoxin and utilizes a protoxin that is at least several fold less toxic than the activated toxin.

The present invention provides a conditional lethal transgene in the two T-DNA construct and a method to select against a plant cell, plant or progeny thereof that express a conditional lethal phenotype. A conditional lethal phenotype involves the expression of a gene product that is not lethal to a cell under normal conditions. To this end the conditional lethal phenotype is used to eliminate the unwanted plant cells, plant tissues or plants when it is most desirable to do so. The present invention provides DNA constructs in novel combinations with positive selectable marker transgenes and methods for the use of these DNA constructs with or without a conditional lethal phenotype in a two T-DNA system for plants. The methods of the present invention enhance the identification and selection of transgenic events in which the two T-DNA segments have integrated into the plant genome at different physical and genetic loci, and provide transgenic plants with agronomically useful transgenes and phenotypes free of the marker transgenes.

SUMMARY OF THE INVENTION

The present invention provides a DNA construct comprising at least two T-DNA molecules and at least two DNA segments separating said T-DNA molecules, wherein a conditional lethal gene resides in at least one DNA segment. In another aspect of the invention, a DNA construct is provided comprising at least two T-DNA molecules and at least two DNA segments separating said T-DNA molecules, wherein a conditional lethal gene resides in each DNA segment.

In another aspect of the invention, a DNA construct is provided comprising at least two T-DNA molecules and at least two DNA segments separating said T-DNA molecules, wherein a first conditional lethal gene resides in any one DNA segment and a second conditional lethal gene heterologous to said first conditional lethal gene resides in any one of the T-DNA molecules. In a further aspect of the invention, a DNA construct is provided comprising at least two T-DNA molecules and at least two DNA segments separating said T-DNA molecules, wherein a first conditional lethal gene resides in one DNA segment and a second conditional lethal gene resides in the second DNA segment; and a third conditional lethal gene heterologous to said first and second conditional lethal gene resides in any one of the T-DNA molecules. In a further aspect of the invention, the expression of a conditional lethal gene residing in a T-DNA molecule is under the control of a tissue specific or inducible promoter.

In a further aspect of the invention, a DNA construct is provided comprising at least two T-DNA molecules and at least two DNA segments separating said T-DNA molecules, wherein one of the T-DNA molecules contains a selectable marker gene and a conditional lethal gene. In another aspect of the invention, a DNA construct is provided comprising at least two T-DNA molecules and at least two DNA segments separating said T-DNA molecules, wherein one of the T-DNA molecules contains a selectable marker gene and a first conditional lethal gene; and a second conditional lethal gene heterologous to said first conditional lethal gene resides in any one DNA segment. In still another aspect of the invention, a DNA construct is provided comprising at least two T-DNA molecules and at least two DNA segments separating said T-DNA molecules, wherein one of the T-DNA molecules contains a selectable marker gene and a first conditional lethal gene; and a second conditional lethal gene resides in one DNA segment and a third conditional lethal gene resides in the other DNA segment, the second and third conditional lethal genes being heterologous to said first conditional lethal gene.

In still a further aspect of the invention, a DNA construct is provided comprising at least two T-DNA molecules and at least two DNA segments separating said T-DNA molecules, wherein one of the T-DNA molecules contains an agronomic gene of interest and a conditional lethal gene. In another aspect of the invention, a DNA construct is provided comprising at least two T-DNA molecules and at least two DNA segments separating said T-DNA molecules, wherein one of the T-DNA molecules contains an agronomic gene of interest and a first conditional lethal gene; and a second conditional lethal gene heterologous to said first conditional lethal gene resides in any one DNA segment. In still another aspect of the invention, a DNA construct is provided comprising at least two T-DNA molecules and at least two DNA segments separating said T-DNA molecules, wherein one of the T-DNA molecules contains an agronomic gene of interest gene and a first conditional lethal gene; and a second conditional lethal gene resides in one DNA segment and a third conditional lethal gene resides in the other DNA segment and the second and third conditional lethal genes are heterologous to said first conditional lethal gene. In an aspect of the invention, the expression of the conditional lethal gene contained within the T-DNA is preferably driven by a tissue specific promoter or inducible promoter.

In another aspect of the invention, a DNA construct is provided comprising at least two T-DNA molecules and at least two DNA segments separating said T-DNA molecules, wherein the T-DNA molecules each contain at least two plant expression cassettes, one plant expressing cassette comprising a conditional lethal gene, the other plant expression cassette containing a selectable marker gene or agronomic gene of interest expressible in plants.

In another aspect of the invention, a DNA construct is provided comprising at least two T-DNA molecules and at least two DNA segments separating said T-DNA molecules, wherein the T-DNA molecules each contain at least two plant expression cassettes, one plant expressing cassette comprising a conditional lethal gene, the other plant expression cassette containing a selectable marker gene or agronomic gene of interest expressible in plants; and the conditional lethal genes are heterologous to each other.

A further aspect of the invention, a DNA construct is provided comprising at least two T-DNA molecules and at least two DNA segments separating said T-DNA molecules, wherein the T-DNA molecules contain at least two plant expression cassettes, wherein the first T-DNA molecule comprises a first plant expression cassette comprising a first conditional lethal gene and a second plant expression cassette containing a selectable marker gene or agronomic gene of interest expressible in plants; and wherein the second T-DNA molecule comprises a third plant expression cassette comprising a second conditional lethal gene heterologous to said first conditional lethal gene and a fourth plant expression cassette containing a selectable marker gene or agronomic gene of interest expressible in plants; and an additional conditional lethal gene that is heterologous to the conditional lethal genes comprising the T-DNA molecules is located in at least one DNA segment. In a further aspect of the invention, the expression of the T-DNA conditional lethal genes is under the control of a tissue specific or inducible promoter.

A method for enhancing the segregation of transgenes in plants described herein for producing transgenic plant cells and plants comprising the steps of:

a) introducing a DNA construct into a plant cell, wherein said DNA construct comprises a first DNA molecule comprising a first T-DNA molecule, and a second DNA molecule comprising a second T-DNA molecule, and a plant expression cassette that expresses a conditional lethal gene product is located in a DNA segment positioned between said first T-DNA molecule and said second T-DNA molecule; and b) treating said plant cell with a protoxin in amounts sufficient to cause the impairment of the cells when said protoxin is converted to a toxic compound by the expression product of the conditional lethal gene; and c) regenerating unimpaired plant cells into plants.

In a method for enhancing the segregation of transgenes in plants, the present invention further providing a method for producing transgenic plant cells and plants comprising the steps of:

a) introducing a DNA construct into a plant cell, said DNA construct comprises at least two T-DNA molecules and at least two DNA segments, wherein a plant expression cassette that expresses a conditional lethal gene product is located in any one of said DNA segments; and b) growing said plant cell into a plant; and c) collecting seeds from said plant; and d) planting the seeds to cause germination of the seeds and growth of seedling plants; and e) treating the seedling plants with a protoxin in amounts sufficient to cause impairment of cells of the treated seedling plants when said protoxin is converted to a toxic compound by the expression product of the conditional lethal gene.

The afore described method, wherein the conditional lethal gene product encodes for a protein comprising phosphonate monoester hydrolase, carboxylate ester hydrolase, glyphosate oxidase, N-acetyl-L-ornithine deacetylase, P450 monooxygenase CPY105A1, cytosine deaminase, indoleacetamide hydrolase, or β-glucuronidase.

The afore described method, wherein said protoxin comprises phosphonate ester of glyphosate, carboxylate ester of glyphosate, glyphosate, N-acetyl-L-phosphinothricin, sulfonamide R7402 protoxin, 5-fluorocytosine, naphthyl-acetamide, or glucuronic acid conjugates of herbicides.

The afore described method, wherein said DNA construct is introduced into a plant cell by an *Agrobacterium* mediated transformation method.

The afore described method, wherein a first T-DNA molecule and a second T-DNA molecule further comprise plant expression cassettes encoding for traits selected from the group consisting of herbicide tolerance, antibiotic resistance, insect resistance, disease resistance, stress resistance, pharmaceutical protein expression, enhanced nutrition, and enhanced yield.

The afore described method, wherein said treated seedling plants that convert the protoxin into a toxic compound by the expression product of the conditional lethal gene are killed.

A DNA construct is provided wherein a first T-DNA molecule is bordered by a first right border DNA sequence (RB) and a first left border DNA sequence (LB) linked to a second T-DNA molecule that is bordered by a second right border DNA sequence and a second left border DNA sequence, and the two T-DNA molecules are positioned in the DNA construct to have an orientation with respect to each other consisting of RB-first T-DNA-LB-LB-second T-DNA-RB, wherein the first RB and second RB are linked and contained in any one of the T-DNA molecules is at least one functional element required for maintenance of the DNA construct as a plasmid in a bacteria cell and a plant selectable marker gene that provides antibiotic or herbicide selection resides in this T-DNA.

A method for providing a transgenic plant with independently segregating transgenes comprising the steps of: a) introducing a DNA molecule into a plant cell by an *Agrobacterium* mediated method, wherein said DNA molecule consists of a first right border region linked to at least one transgene of agronomic interest linked to a first left border region linked to a second left border region linked to a positive selectable marker transgene linked to a plasmid maintenance element linked to a second right border region, wherein the second right border region is linked to the first right border region; and b) regenerating said plant cell into a transgenic plant by positive selection provided by expression of said positive selectable marker transgene; and c) selecting said transgenic plant for the presence of said transgene of agronomic interest; and d) screening said transgenic plant by a DNA detection method that identifies the linkage of said transgene of agronomic interest and said positive selectable marker transgene; and e) growing said transgenic plant into a fertile plant in which said transgene of agronomic interest and said positive selectable marker transgene are not linked. The method further comprises the steps of: a) harvesting progeny from said fertile plant; and b) selecting from said progeny those individuals that contain said transgene of agronomic interest and do not contain said positive selectable marker transgene.

A method for providing a transgenic plant with independently segregating transgenes comprising the steps of: a) introducing a DNA molecule into a plant cell by an *Agrobacterium* mediated method, wherein said DNA molecule consists of an *Agrobacterium* Ti plasmid first border region linked to at least one transgene of agronomic interest linked to an *Agrobacterium* Ti plasmid second border region linked to a positive selectable marker transgene; and b) regenerating said plant cell into a transgenic plant by positive selection provided by expression of said positive selectable marker transgene; and c) selecting said transgenic plant for the presence of said transgene of agronomic interest; and d) screening said transgenic plant by a DNA detection method that identifies the linkage of said transgene of agronomic interest and said positive selectable marker transgene; and e) growing said transgenic plant into a fertile plant. The method further comprising the steps of: a) harvesting progeny from said fertile plant; and b) selecting from said progeny those that contain said transgene of agronomic interest and do not contain said positive selectable marker transgene, wherein said progeny are seeds or seedlings thereof. The transgene of agronomic interest provides an agronomic trait comprising herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress tolerance, increased digestibility, industrial enzyme production, pharmaceutical peptides and small molecule production, improved processing traits, proteins improved flavor, nitrogen fixation, hybrid seed production, reduced allergenicity, biopolymers, or biofuel production. The method further provides a transgenic plant that is a crop plant and a positive selectable marker transgene provides tolerance to an antibiotic or herbicide. The positive selectable marker transgene is also linked to a plasmid maintenance element. The positive selectable marker transgene and plasmid maintenance element may also be linked to a conditional lethal transgene.

A method for providing a transgenic plant with independently segregating transgenes comprising the steps of: a) introducing a DNA molecule into a plant cell, wherein said DNA molecule consists of an *Agrobacterium* Ti plasmid first border region linked to at least one transgene of agronomic interest linked to an *Agrobacterium* Ti plasmid second border region linked to a positive selectable marker transgene; and b)

regenerating said plant cell into a transgenic plant by positive selection provided by expression of said positive selectable marker transgene; and c) selecting said transgenic plant for the presence of said transgene of agronomic interest; and c) growing said transgenic plant into a fertile plant that contains said transgene of agronomic interest and said positive selectable marker transgene; and e) harvesting seeds from said fertile plant; and f) selecting the seeds or seedlings thereof, that contain said transgene of agronomic interest and do not contain said positive selectable marker transgene.

A DNA plasmid consisting of a first *Agrobacterium* Ti plasmid right border region linked to at least one transgene of agronomic interest linked to a second *Agrobacterium* Ti plasmid right border region linked to an antibiotic selectable marker transgene or a herbicide selectable marker transgene wherein said antibiotic selectable marker transgene or herbicide selectable marker transgene is linked to a plasmid maintenance element. The antibiotic selectable marker transgene or herbicide selectable marker transgene may also be linked to a conditional lethal transgene.

A DNA plasmid consisting of a first *Agrobacterium* Ti plasmid left border region linked to at least one transgene of agronomic interest linked to a second *Agrobacterium* Ti plasmid left border region linked to an antibiotic selectable marker transgene or a herbicide selectable marker transgene wherein said antibiotic selectable marker transgene or herbicide selectable marker transgene is linked to a plasmid maintenance element. The antibiotic selectable marker transgene or herbicide selectable marker transgene may also be linked to a conditional lethal transgene.

A DNA plasmid consisting of an *Agrobacterium* Ti plasmid right border region linked to at least one transgene of agronomic interest linked to an *Agrobacterium* Ti plasmid left border region linked to an antibiotic selectable marker transgene or a herbicide selectable marker transgene wherein said antibiotic selectable marker transgene or herbicide selectable marker transgene is linked to a plasmid maintenance element. The antibiotic selectable marker transgene or herbicide selectable marker transgene may also be linked to a conditional lethal transgene.

A method of determining the expression pattern of a tissue specific DNA promoter for use in transgenic plants the steps comprising:

b) constructing of a DNA construct containing at least a first and a second plant expression cassette, wherein the first plant expression cassette has a constitutive promoter and the second plant expression cassette has a tissue specific promoter and wherein the plant expression cassettes are in separate T-DNAs and:

c) transforming the DNA construct into a plant cell; and d) regenerating said plant cell into a fertile plant; and e) assaying said plant for the presence of the plant expression cassettes; and f) assaying said plant by a DNA detection method that identifies the linkage of the plant expression cassettes; and g) assaying said plant for the expression pattern, or expression rate, or expression level of a gene product produced by the expression cassette having the tissue specific promoter; and f) selecting said tissue specific promoter for use in the construction of additional DNA constructs.

In a method for enhancing the segregation of transgenes in plants, the present invention further provides a method for stacking transgene traits in plants comprising the steps of: a) constructing a first DNA construct comprising at least two T-DNA molecules, wherein a first T-DNA molecule comprises a first plant expression cassette that provides at least one agronomic gene of interest; and a second T-DNA molecule comprising a second plant expression cassette that provides a positive selectable marker gene product functional in plant cells and a third plant expression cassette that provides a conditional lethal gene product functional in plant cells; and b) transforming said first DNA construct into a plant cell; and c) treating said plant cell with an effective amount of a positive selection compound for which tolerance is provided by said positive selectable marker gene product; and d) regenerating a positive selection compound tolerant plant cell into a fertile plant; and e) collecting seeds from said fertile plant; and f) planting seeds from said fertile plant that germinate to produce seedling plants; and g) treating the seedling plants with a protoxin in amounts sufficient to cause damage or death to the plant cells of the treated seedlings when said protoxin is converted to a toxic compound by said conditional lethal gene product; and h) selecting a seedling plant from the treated seedling plants for the presence of the first T-DNA and for no plant cell impairment of the type caused by the conversion of the protoxin to a toxic compound; and i) propagating said seedling plant selected in step (h) into a fertile plant; and j) constructing a second DNA construct comprising at least two T-DNA molecules, wherein a third T-DNA molecule comprises a fourth plant expression cassette that provides at least one agronomic gene of interest; and the second T-DNA molecule of the first DNA construct; and k) retransforming said fertile plant of step (i) with said second DNA construct; and l) repeating steps c-g; and m) selecting a seedling plant for the presence of the agronomic gene of interest of the first DNA construct and the agronomic gene of interest of the second DNA construct and for no plant cell impairment of the type caused by the conversion of the protoxin to a toxic compound; and n) propagating said seedling plant selected in step (m) into a fertile plant.

In a method for enhancing the segregation of transgenes in plants, the present invention further provides a method of controlling the dissemination of transgenes by pollen outcrossing comprising the steps of: a) constructing a DNA construct comprising a first T-DNA molecule and a second T-DNA molecule, said first T-DNA molecule comprising a first plant expression cassette and a second plant expression cassette, wherein said first plant expression cassette provides a selectable gene product and said second plant expression cassette provides a first conditional lethal gene product expressed under the control of a plant male reproductive tissue specific promoter; and said second T-DNA segment comprising a third plant expression cassette and a fourth plant expression cassette, wherein said third plant expression cassette provides an agronomic gene of interest and said fourth plant expression cassette provides a second conditional lethal gene product expressed under the control of a plant pollen specific promoter, wherein said second conditional lethal gene product is heterologous to said first conditional lethal gene product; and b) transforming said DNA vector into a plant cell; and c) growing said plant cell into a fertile first parent plant homozygous for said first and second T-DNA segments; and d) crossing said fertile first parent plant with a fertile second parent plant to produce a hybrid plant; and e) harvesting seed from said hybrid plant; and f) planting said seed from said hybrid plant in a field under conditions that cause the germination of said seed and growth into plants; and h) treating the plants of step (f) with an effective amount of a compound that is converted to a toxin by the conditional lethal gene product expressed under the control of a plant male tissue specific promoter to cause impairment or death of pollen expressing the conditional lethal gene product.

A method for enhancing the segregation of transgenes in plants comprising the steps of:

a) introducing at least two DNA constructs into a plant cell, wherein a first and second DNA construct comprises at least one T-DNA molecule and at least one DNA segment, wherein a plant expression cassette that expresses a conditional lethal gene product is located in the DNA segment; and b) growing said plant cell into a plant; and c) collecting seeds from said plant; and d) planting the seeds to cause germination of the seeds and growth of seedling plants; and e) treating the seedling plants with a protoxin in amounts sufficient to cause death of cells of the treated seedling plants when said protoxin is converted to a toxic compound by the expression product of the conditional lethal gene.

The afore described method, wherein the conditional lethal gene product encodes for a protein comprising phosphonate monoester hydrolase, carboxylate ester hydrolase, glyphosate oxidase, N-acetyl-L-ornithine deacetylase, P450 monooxygenase CPY105A1, cytosine deaminase, indoleacetamide hydrolase, or β-glucuronidase The afore described method, wherein said protoxin comprises phosphonate ester of glyphosate, carboxylate ester of glyphosate, glyphosate, N-acetyl-L-phosphinothricin, sulfonamide R7402 protoxin, 5-fluorocytosine, naphthyl-acetamide, or glucuronic acid conjugates of herbicides.

The afore described method, wherein said DNA construct is introduced into a plant cell by an *Agrobacterium* mediated transformation method and the *Agrobacteria* comprise nopaline and octopine strains.

The present invention provides DNA constructs that express a conditional lethal gene product comprising phosphonate monoester hydrolase, glyphosate oxidoreductase, carboxy ester hydrolase, N-acetyl-L-ornithine deacetylase, P450 monooxygenase CPY105A1, cytosine deaminase, indoleacetamide hydrolase, or β-glucuronidase, wherein the gene product interacts with a compound that is converted to a toxin by the conditional lethal gene product, the compound comprising phosphonate ester of glyphosate, glyphosate, carboxylate ester of glyphosate, N-acetyl-L-phosphinothricin, sulfonamide R7402 protoxin, 5-fluorocytosine, naphthyl-acetamide, glucuronic acid conjugates of herbicides, respectively.

The present invention provides DNA constructs that contain a herbicide resistant gene product comprising genes for class II EPSPS inhibitor resistant enzymes, class I EPSPS inhibitor resistant enzymes, aceto-lactone synthase inhibitor resistant enzymes, glutamine synthase inhibitor enzymes.

The present invention further comprises DNA constructs that contain additional agronomic genes of interest selected from the group consisting of herbicide tolerance, antibiotic resistance, insect resistance, disease resistance, stress resistance, pharmaceutical protein expression, enhanced nutrition, and enhanced yield.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
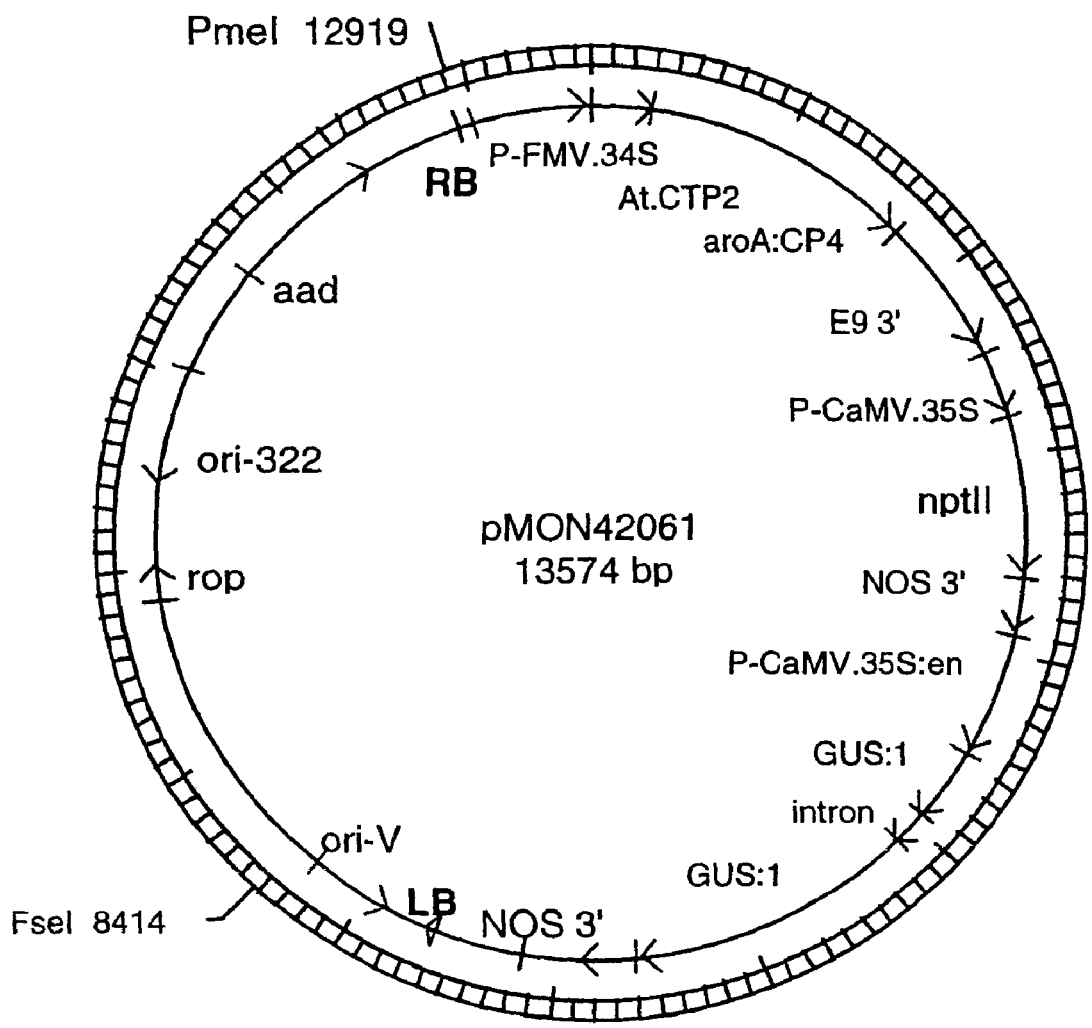
FIG. 1. Plasmid map of pMON42061
FIG. 2. Plasmid map of pMON51652
FIG. 3. Plasmid map of pMON51653
FIG. 4. Plasmid map of pMON54237
FIG. 5. Plasmid map of pMON51658
FIG. 6. Plasmid map of pMON51661
FIG. 7. Plasmid map of pMON51676
FIG. 8. Plasmid map of pMON42073
FIG. 9. Plasmid map of pMON42070
FIG. 10. Plasmid map of pMON42071
FIG. 11. Plasmid map of pMON42072
FIG. 12. Plasmid map of pMON9443
FIG. 13. Plasmid map of pMON9430
FIG. 14. Plasmid map of pMON17164
FIG. 15. Plasmid map of pMON73105
FIG. 16. Plasmid map of pMON73107
FIG. 17. Plasmid map of pMON73106
FIG. 18. Plasmid map of pMON73108
FIG. 19. Plasmid map of pMON62400
FIG. 20. Plasmid map of pMON65178
FIG. 21. Plasmid map of pMON65179
FIG. 22. Plasmid map of pMON65180
FIG. 23. Plasmid map of pLagILB01
FIG. 24. Plasmid design with duplicated border regions
FIG. 25. Alternative plasmid designs with duplicated border regions
FIG. 26. Plasmid design with two border regions

Herein we describe and exemplify compositions and methods that are useful for enhancing the occurrence of segregating agronomic genes of interest transformed into plants as transgenes, comprising T-DNA molecules that include, but not limited to, herbicide resistance genes; insecticidal protein genes from *Bacillus* species and other bacteria, fungi, and plants; antibiotic protein genes from viruses, bacteria, fungi, plants and animals; genes affecting plant growth and development, such as genes involved in plant hormone biosynthesis or degradation, vitamin biosynthesis, and cellular architecture, comprising herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress tolerance, increased digestibility, industrial enzyme production, pharmaceutical peptides and small molecule production, improved processing traits, proteins improved flavor, nitrogen fixation, hybrid seed production, reduced allergenicity, biopolymers, or biofuel production.

The DNA constructs of the present invention comprises at least two T-DNA molecules and at least two *Agrobacterium* Ti plasmid border regions. In a method of the present invention steps comprise the treatment of plant cells transformed with the DNA constructs, plants or segregating progeny thereof derived from the transformed plant cells, with a protoxin that when converted into a toxin by any one of the conditional lethal gene products described herein, eliminates the cells or progeny plants from the population of treated cells or plants.

Additionally, it may be desirable to reduce or eliminate a T-DNA molecule in a particular cell, tissue, or organ, but not in other parts of a plant in which the transgene is expressed. The elimination of pollen that is expressing insecticidal proteins is desirable as well as eliminating the potential for the outcrossing of transgenes to related plants and into adjacent fields from hybrid crops. In this aspect of the invention, a method is provided applicable to hybrid plants including monocotyledons such as rice, wheat, oats, barley, corn and the like, as well as dicotyledons such as alfalfa, canola, carrot, cotton, oil seed rape, sugar beet, sunflower, soybean, tomato and the like. Generally, this process comprises applying a selected protoxin compound to the transgenic hybrid crop plant that is expressing a conditional lethal gene product by a male specific promoter, thereby causing the death of pollen where the expression of the enzyme converts the protoxin into a toxin. Any agronomic gene(s) of interest associated with the alleles contributed by the transgenic parent that carry the conditional lethal gene will be eliminated. In a related method, there is provided a process to eliminate a certain T-DNA molecule and the expression cassettes contained therein from a plant breeding program in which it has become desirable to remove a particular transgene from the breeding plant parent populations. Such compositions and methods may be used with respect to any plant that can be genetically modified by biotechnology.

Additionally, the two T-DNAs integrated at physically and genetically distinct locations in the plant genome reduce the interactions that can occur between closely linked genetic elements in a plant expression cassette. Strong constitutive promoters may influence the expression pattern or rate of transcription of a closely associated transgenic tissue specific promoter. The segregation of the T-DNAs by the methods of the present invention can reduce the promoter/promoter interactions that can be problematic when multiple expression cassettes are used in a single T-DNA. The methods of the present invention can be applied to determine if transgene plant expression cassettes interact to influence the expression pattern of the genes of interest, and as a result, the combinations of expression cassettes can be optimized to enable a more predictive pattern of expression of the transgenes. The use of the method for this purpose saves considerable time and expense in designing and making DNA constructs and in producing and evaluating transgenic plants.

The methods of the present invention provide enhanced plant transformation efficiency, wherein the efficiency is measured in the transformed plants as a high frequency of expression of both T-DNA inserts from a two T-DNA construct and the T-DNA inserts are located at unlinked genetic loci and the transformed plants have a low occurrence of extraneous vector DNA in the plant genome. In these methods, the DNA construct comprising a two T-DNA construct, have T-DNA border sequences that form an orientation dependent enhancement within the DNA construct, the orientation being a right border-first T-DNA-left border, left border-second T-DNA-right border.

In a further aspect of the method, at least two DNA constructs each comprising at least one T-DNA and a DNA segment containing a conditional lethal gene are introduced into disarmed *Agrobacteria* cells, one DNA construct into a nopaline *Agrobacterium* strain and one DNA construct into an octopine *Agrobacterium* strain. The two strains, each containing a different DNA construct, are mixed together in an *Agrobacterium* mediated plant transformation method.

The following definitions and methods are provided to better define the present invention and to guide those of ordinary skill in the art in the practice of the present invention.

Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York (1991); and Lewin, Genes V, Oxford University Press: New York (1994). The nomenclature for DNA bases as set forth at 37 CFR §1.822 is used. The standard one- and three-letter nomenclature for amino acid residues is used.

Abbreviations for nucleotide bases in nucleic acid codes as used herein are: A=adenosine; C=cytosine; G=guanosine; T=thymidine. Codes used for synthesis of oligonucleotides as used herein are: N=equimolar A, C, G, and T; I=deoxyinosine; K=equimolar G and T; R=equimolar A and G; S=equimolar C and G; W=equimolar A and T; Y=equimolar C and T.

"Carboxylate ester of glyphosate" comprise a class of protoxin compounds that can be converted to active glyphosate by hydrolysis of the ester bond between the carboxy group and N-phosphonomethyl-glycine.

"conditional lethal gene product" as defined herein, as a peptide, protein or enzyme that when expressed in transgenic plant cells converts a chemical compound that has low phytotoxicity or is nonphytotoxic in the present environment of the plant cell into a compound that is highly toxic in a plant cell environment that now includes the conditional lethal gene product. Examples of conditional lethal gene products include, but are not limited to phosphonate monoester hydrolase, carboxylate ester hydrolase, glyphosate oxidase, N-acetyl-L-ornithine deacetylase, P450 monooxygenase CPY105A1 or β-glucuronidase. This definition includes a herbicide tolerant plant cell environment in which the herbicide is converted into a compound for which the plant cell is no longer tolerant.

As used herein, the term "comprise" can be used interchangeably with the phrase "includes, but is not limited to."

"CP4", "aroA:CP4", "AGRTU.aroA:CP4", "CP4 EPSPS" and "EPSPS CP4" refer to the EPSP synthase gene or protein purified from *Agrobacterium tumefaciens* (AGRTU) strain CP4 that when expressed in plants confers tolerance to glyphosate and glyphosate containing herbicide formulations (U.S. Pat. No. 5,633,435, herein incorporated by reference in it's entirety). The gene sequence may be native or modified for enhanced expression in plants.

A DNA "segment" refers a region of DNA sequence of a DNA construct for which it is generally not desirable to have it integrated into a plant genome. A DNA segment is between or flanks the T-DNA molecules. A DNA segment often contains the genetic elements for replication of plasmids in bacteria and is the DNA sequence that various elements and expression cassettes of the present invention are located.

"GOX" refers to glyphosate oxidoreductase protein and the gene that encodes for enzymes that can degrade glyphosate (N-phosphonomethyl-glycine) and other substrates to aminomethylphosphonate (AMPA). The glyphosate oxidoreductase gene nucleotide sequence and modifications made to the nucleotide sequence as described in U.S. Pat. No. 5,463,175 and U.S. Pat. No. 5,312,910, herein incorporated by reference in their entirety.

A "homolog" of a gene of one species is a nucleic acid sequence to which a probe or primer derived from the gene that binds under at least moderately stringent hybridization conditions to a nucleic acid sequence of a second species.

"Impairment" of a plant cell or a plant by the presence of a toxin molecule refers to a reduction in the normal function of a plant cell or a plant. The impairment can be determined by a visual observation or by measuring a physiological or chemical change in the plant cell or plant. Impairment in the extreme results in death of the plant cell, plant tissues or plants.

An "isolated" nucleic acid is substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

The term "chimeric" refers to the product of the fusion of portions of two or more different nucleic acids or proteins.

For the purposes of the present invention, the term "glyphosate" includes any herbicidally active form of N-phosphonomethylglycine (including any salt thereof) and other forms that result in the production of the glyphosate anion in plants. Glyphosate is the active ingredient of Roundup® and Roundup Ultra® herbicide formulations, for example (Monsanto Company, St. Louis, Mo.). Treatments with "glyphosate" refer to treatments with the Roundup® or Roundup Ultra® herbicide formulation, unless otherwise stated. Plant transformation and regeneration in tissue culture use glyphosate or salts of glyphosate. Whole plant assays use formulated Roundup® Ultra. Additional formulations with herbicide activity that contain N-phosphonomethylglycine or any of its salts are herein included as a glyphosate herbicide.

"Glycerol glyphosate" refers to the compound glycine, N-([hydroxy (2,3 dihydroxy propoxy)phosphonyl]methyl) is representative of the general class of phosphonate esters of glyphosate that is a substrate for phosphonate monoester hydrolases, is relatively non-cytotoxic and translocates to developing plant tissues.

The term "glyphosate resistance gene" refers to any gene that, when expressed as a transgene in a plant, confers the ability to tolerate levels of the herbicide glyphosate that would otherwise damage or kill the plant. Any glyphosate tolerance gene known to the skilled individual are suitable for use in the practice of the present invention. Glyphosate inhibits the shikimic acid pathway that leads to the biosynthesis of aromatic compounds including amino acids, plant hormones and vitamins. Specifically, glyphosate inhibits the enzyme 5-enolpyruvylshikimate-3-phosphate synthase (EPSPS). A variety of native and variant EPSPS enzymes have been expressed in transgenic plants in order to confer glyphosate tolerance (Singh et al., In "Biosynthesis and Molecular Regulation of Amino Acids in Plants", Amer. Soc. Plant Phys., 1992), any of which can be used in the invention. Examples of some of these EPSPSs include those described and/or isolated in accordance with U.S. Pat. No. 4,940,835, U.S. Pat. No. 4,971,908, U.S. Pat. No. 5,145,783, U.S. Pat. No. 5,188,642, and U.S. Pat. No. 5,310,667, herein incorporated by reference in their entirety. They can also be derived from a structurally distinct class of non-homologous EPSPS genes, such as the class II EPSPS genes isolated from *Agrobacterium* sp. strain CP4 (AGRTU.aroA:CP4) as described in U.S. Pat. Nos. 5,633,435, 5,804,425 and 5,627,061, herein incorporated by reference in their entirety.

The term "native" refers to a naturally-occurring ("wild-type") nucleic acid or polypeptide.

A first nucleic-acid sequence is "operably" connected or "linked" with a second nucleic acid sequence when the first nucleic acid sequence is placed in a functional relationship with the second nucleic acid sequence. For instance, a promoter is operably linked to a protein-coding sequence if the promoter affects the transcription or expression of the coding sequence. Generally, operably linked DNA sequences are contiguous and, where necessary to join two protein-coding regions, are in the same reading frame.

The enzyme "phosphonate monoester hydrolase" (PEH) of the present invention catalyzes the cleavage of phosphonate esters into the free phosphonate and an alcohol. The enzyme was first identified by its ability to hydrolyze the glyceryl glyphosate into glycerol and glyphosate. The enzyme has since been shown to hydrolyze other protoxin compounds as well as numerous other phosphonate monoesters including colorimetric substrates. The gene (pehA) encoding the subject phosphonate monoester hydrolase enzyme is directed to the isolation of such a gene from *Pseudomonas caryophilli* PG2982 (NCIMB #12533) as described in U.S. Pat. No. 5,254,801, herein incorporated by reference in its' entirety.

The term "plant" encompasses any higher plant and progeny thereof, including monocots (e.g., lily, corn, rice, wheat, barley, etc.), dicots (e.g., tomato, potato, soybean, cotton, canola, tobacco, etc.), and includes parts of plants, including reproductive units of a plant (e.g., seeds), fruit, flowers, etc.

A "recombinant" nucleic acid is made by an artificial combination of two otherwise separated segments of sequence, e.g., by chemical synthesis or by the manipulation of isolated segments of nucleic acids by genetic engineering techniques.

A "reproductive unit" or propagule of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

The terms "DNA construct" or "DNA vector" refers to any plasmid, cosmid, virus, autonomously replicating sequence, phage, or other circular single-stranded or double-stranded DNA or RNA derived from any source that includes one or more DNA sequences, such as promoters, protein-coding sequences, 3' untranslated regions, etc., that have been linked in a functionally operative manner by recombinant DNA techniques. Recombinant DNA vectors for plant transformation are commonly double-stranded circular plasmids capable of replication in a bacterial cell. Conventional compositions and methods for making and using recombinant nucleic acid constructs are discussed, inter alia, in Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). See also, e.g., Mailga et al., Methods in Plant Molecular Biology, Cold Spring Harbor Press (1995); Birren et al., Genome Analysis Detecting Genes, 1, Cold Spring Harbor, N.Y. (1998); Birren et al., Genome Analysis: Analyzing DNA, 2, Cold Spring Harbor, N.Y. (1998); and Clark et al., Plant Molecular Biology: A Laboratory Manual, Springer, New York (1997).

Methods for chemical synthesis of nucleic acids are discussed, for example, in Beaucage and Carruthers, Tetra. Letts. 22:1859-1862 (1981), and Matteucci et al., J. Am. Chem. Soc. 103:3185 (1981). Chemical synthesis of nucleic acids can be performed, for example, on commercial automated oligonucleotide synthesizers.

A number of vectors suitable for stable transformation of plant cells or for the establishment of transgenic plants have been described in, e.g., Pouwels et al., Cloning Vectors: A Laboratory Manual (1985, supp. 1987); Weissbach and Weissbach, Methods for Plant Molecular Biology, Academic Press (1989); and Gelvin et al., Plant Molecular Biology Manual, Kluwer Academic Publishers (1990). Typically, plant expression vectors include one or more transcription units, each of which includes: a 5' untranslated region, which includes sequences that control transcription (e.g., cis-acting promoter sequences such as enhancers, the transcription initiation start site, etc.) and translation (e.g., a ribosome binding site) of an operably linked protein-coding sequence ("open reading frame", ORF); a 3' untranslated region that includes additional regulatory regions from the 3' end of plant genes (Thornburg et al., Proc. Natl. Acad. Sci. USA 84:744 (1987); An et al., Plant Cell 1:115 (1989), e.g., a 3' terminator region to increase mRNA stability. In addition, such constructs commonly include a selectable or screenable marker and optionally an origin of replication or other sequences required for replication of the vector in a host cell.

Plant expression vectors optionally include RNA processing signals, e.g., introns, which may be positioned upstream or downstream of a polypeptide-encoding sequence in the transgene. An intron element is identified in a description of an expression cassette by "I-" preceding a gene name, coding sequence name or genomic identification number. In addition, the expression vectors may also include additional regulatory sequences from the 3'-untranslated region of plant genes. These 3' untranslated regions contain mRNA transcription termination signals, thus these regions when used in chimeric expression cassettes are designated with "T-" followed by a gene name, coding sequence name or genomic identification number. Other movable elements contained in plant expression vectors may include 5' leader sequences, designated by "L-" and transit signal sequences designated by "TS-", each followed by a gene name, coding sequence name or genomic identification number. The elements of a plant expression cassette are described in a 5' to 3' orientation of the linked elements using the element names separated by a "/".

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA. A "P-" preceding a gene, coding sequence name or genomic identification number designates the element as a promoter. The genus species of the source of the promoter element is used in the promoter name, for example, *Zea mays* (corn) is abbreviated to Zm, Cauliflower mosaic virus is CaMV, *Triticum aesativum* (wheat) is Ta, *Orysae sativa* (rice) is Os and so forth. The 35S promoter of CaMV is therefore, P-CaMV.35S.

"Regeneration" refers to the process of growing a plant from a plant cell (e.g., plant protoplast or explant).

"Reporter" refers to a gene and corresponding gene product that when expressed in transgenic organisms produces a product detectable by chemical or molecular methods or produces an observable phenotype.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Retransformation" refers to a method, wherein a new transgene is introduced by the methods of plant transformation into a plant cell that in itself is a transgenic cell produced by transformation at an earlier time.

"Selectable marker" refers to a nucleic acid sequence whose expression confers a phenotype facilitating identification of cells containing the nucleic acid sequence. Selectable markers include those that confer resistance to toxic chemicals (e.g. ampicillin resistance, kanamycin resistance), complement a nutritional deficiency (e.g. uracil, histidine, leucine), or impart a visually distinguishing characteristic (e.g. color changes or fluorescence). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase, modified ALS, modified class I EPSPSs, class II EPSPSs). A useful strategy for selection of transformants for herbicide resistance is described, e.g., in Vasil, Cell Culture and Somatic Cell Genetics of Plants, Vols. I-III, Laboratory Procedures and Their Applications Academic Press, New York (1984).

The term "specific for (a target sequence)" indicates that a probe or primer hybridizes under given hybridization conditions only to the target sequence in a sample comprising the target sequence.

"T-DNA molecule" refers to a DNA molecule that integrates into a plant genome via an *Agrobacterium* mediated transformation method. The ends of the T-DNA molecule are defined in the present invention as being flanked by the border regions of the T-DNA from *Agrobacterium* Ti plasmids. These border regions are generally referred to as the Right border and Left border regions and exist as variations in nucleotide sequence and length depending on whether they are derived from nopaline or octopine producing strains of *Agrobacterium*. The border regions commonly used in DNA constructs designed for transferring transgenes into plants are often several hundred polynucleotides in length and comprise a nick site where an endonuclease digests the DNA to provide a site for insertion into the genome of a plant. The T-DNA molecule generally contain one or more plant expression cassettes.

"Tolerant" refers to a reduced toxic effect of a herbicide on the growth and development of microorganisms and plants.

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast that exogenous nucleic acid is incorporated into a chromosome or is capable of autonomous replication.

"Transformed" or "transgenic" refers to a cell, tissue, organ, or organism into that has been introduced a foreign nucleic acid, such as a recombinant vector. A "transgenic" or "transformed" cell or organism also includes progeny of the cell or organism and progeny produced from a breeding program employing such a "transgenic" plant as a parent in a cross and exhibiting an altered phenotype resulting from the presence of the foreign nucleic acid.

The term "transgene" refers to any nucleic acid sequence normative to a cell or organism transformed into said cell or organism. "Transgene" also encompasses the component parts of a native plant gene modified by insertion of a normative nucleic acid sequence by directed recombination.

The term "translation" refers to the production the corresponding gene product, i.e., a peptide, polypeptide, or protein from a mRNA.

"Isolated," "Purified," "Homogeneous" Polypeptides. A polypeptide is "isolated" if it has been separated from the cellular components (nucleic acids, lipids, carbohydrates, and other polypeptides) that naturally accompany it or that is chemically synthesized or recombinant. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Coat proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, New York, 1982.

There are a variety of conventional methods and reagents for "labeling" polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., *Molecular Cloning: A Laboratory Manual*, Cold Spring Harbor Press (1989) and Ausubel et al., Greene Publishing and Wiley-Interscience, New York, (1992).

Mature protein coding region. This term refers to the sequence of a post-translationally processed protein product, for example, EPSP synthase remaining after the chloroplast transit peptide sequence has been removed.

Polypeptide fragments. The present invention also encompasses fragments of a coding sequence that lacks at least one residue of a native full-length protein, but that specifically maintains functional activity of the protein.

Transit peptide or targeting sequence (TS-). These terms generally refer to peptide sequences that when linked to a protein of interest directs the protein to a particular tissue, cell, subcellular location, or cell organelle. Examples include, but are not limited to, chloroplast transit peptides, nuclear targeting signals, and vacuolar signals. The chloroplast transit peptide is of particular utility in the present invention to direct expression of the EPSPS enzyme to the chloroplast.

The term "plant" encompasses any higher plant and progeny thereof, including monocots (e.g., corn, rice, wheat, barley, etc.), dicots (e.g., soybean, cotton, tomato, canola, potato, *Arabidopsis*, tobacco, etc.), gymnosperms (pines, firs, cedars, etc.) and includes parts of plants, including reproductive units of a plant (e.g., seeds, bulbs, tubers, or other parts or tissues from that the plant can be reproduced), fruit, flowers, etc.

Included within the terms "scorable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin acetyltransferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

A vector or construct may also include various regulatory elements. The 5' non-translated leader sequence can be derived from the promoter selected to express the heterologous gene sequence of the DNA molecule of the present invention, and can be specifically modified if desired so as to increase translation of mRNA. For a review of optimizing expression of transgenes, see Koziel et al., (Plant Mol. Biol. 32:393-405 (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347, herein incorporated by reference in their entirety.), and the TMV omega element (Gallie et al., The Plant Cell 1:301-311 (1989). Intron sequences are known in the art to aid in the expression of transgenes in monocot plant cells. Examples of such introns include the Adh intron 1 (Callis et al., Genes and Develop. 1:1183-1200 (1987), the sucrose synthase intron (Vasil et al., Plant Physiol. 91:1575-1579 (1989), U.S. Pat. No. 5,955, 330), first intron of the rice actin gene (U.S. Pat. No. 5,641, 876), herein incorporated by reference in their entirety.

A vector may also include a transit peptide nucleic acid sequence (TS-). The glyphosate target in plants, the 5-enolpyruvyl-shikimate-3-phosate synthase (EPSPS) enzyme, is located in the chloroplast. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of Ribulose-1,5,-bisphosphate carboxylase, Ferredoxin, Ferredoxin oxidoreductase, the light-harvesting complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* (At.) EPSPS CTP (Klee et al., Mol. Gen. Genet. 210:437-442), and the *Petunia hybrida* (Ph.) EPSPS CTP (della-Cioppa et al., Proc. Natl. Acad. Sci. USA 83:6873-6877) has been shown to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299, herein incorporated by reference din their entirety). Those skilled in the art will recognize that various chimeric constructs can be made that utilize the functionality of a particular CTP to import conditional lethal gene products into the plant cell chloroplast when necessary to provide the product there for efficacy of the phenotype.

The termination of transcription is accomplished by a 3' non-translated DNA sequence operably linked in the chimeric vector to the gene of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region (Fraley et al., Proc. Natl. Acad. Sci. 80:4803-4807

(1983), the 3' untranslated region from pea small subunit Rubisco gene (Coruzzi et al., EMBO J. 3:1671-1679, 1994), the 3' untranslated region from soybean 7S seed storage protein gene (Schuler et al., Nuc Acids Res. 10:8225-8244, 1982) are commonly used in this capacity. The 3' transcribed, non-translated regions containing the polyadenylate signal of Agrobacterium tumor-inducing (Ti) plasmid genes are also suitable.

For embodiments of the invention in which the use of a constitutive promoter is desirable, any well-know constitutive plant promoter may be used. Constitutive plant promoters include, for example, the cauliflower mosaic virus (CaMV) $^{35}$S promoter, which confers constitutive, high-level expression in most plant tissues (see, e.g., Odel et al., Nature 313: 810, 1985), including monocots (see, e.g., Dekeyser et al., Plant Cell 2:591, 1990); Terada et al., Mol. Gen. Genet. 220:389, 1990); the nopaline synthase promoter (An et al., Plant Physiol. 88:547, 1988), the octopine synthase promoter (Fromm et al., Plant Cell 1:977, 1989), cauliflower mosaic virus 19S promoter, figwort mosaic virus $^{35}$S promoter, sugarcane bacilliform virus promoter, commelina yellow mottle virus promoter, rice cytosolic triosephosphate isomerase promoter, adenine phosphoribosyltransferae promoter, rice actin 1 promoter, mannopine synthase promoter, histone promoter, and a tobacco constitutive promoter as disclosed in U.S. Pat. No. 5,824,872.

For other embodiments of the invention, well-known plant gene promoters that are regulated in response to environmental, hormonal, chemical, and/or developmental signals may be used, including promoters regulated by (1) heat (Callis et al., Plant Physiol. 88:965, 1988), (2) light (e.g., pea rbcS-3A promoter, Kuhlemeier et al., Plant Cell 1:471 (1989); maize rbcS promoter, Schaffner and Sheen, Plant Cell 3:997 (1991); or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, etc. It may also be advantageous to employ (6) organ-specific promoters (e.g., Roshal et al., EMBO J. 6:1155 (1987); Schernthaner et al., EMBO J. 7:1249, 1988); Bustos et al., Plant Cell 1:839, 1989).

It is desirable in one aspect of the invention to use promoters that are preferentially expressed in a reproductive tissue. Any well-known male- or female-specific plant promoter may be used. Promoters that are preferentially expressed in a male tissue, include, but are not limited to, the following: the Xyl promoter (Bih et al., J. Biol. Chem. 274:2884-2894, 1999), RA8 (Jeon et al., Plant Mol. Biol. 39:3544, 1999), Ms45 (WO 9859061), SGB6 (U.S. Pat. No. 5,837,850), Tap1 (WO 9827201), Osg6B (Matsuda et al., Plant Biotechnol. (Tokyo) 14:157-161 (1997), Sta44 (CA 2165934), MS2 (Aarts et al., Plant J. 12:615-623, 1997), Zmg13, TA29 (WO 9325695), SLG and SLR1 (WO 9425613), RST2 (WO 9713401), ZmC5 (WO 9942587), and A3, A6, A9 (WO 9302197, U.S. Pat. No. 5,723,754) promoters, the rice YY1 and YY2 anther-specific promoters (Hihara et al., Plant Mol. Biol. 30:1181-1193 (1996), the corn pollen-specific promoters ZmABP1 and ZmABP2 (Lopez et al., Proc. Nat. Acad. Sci. USA 93:7415-7420 (1996), the tapetum-specific oleosin-like gene promoters in brassica (Ross et al., Plant J. 9:625-637 (1996), the pollen-specific DEFH125 gene promoter from Antirrhinum (Zachgo et al., Plant J. 11: 1043-1050 (1997), the pollen-specific LePro 1 promoter (Yu et al., Plant Mol. Biol. 36:699-707 (1998), the anther-specific MROS gene promoters (Matsunaga et al., Plant J. 10:679-689 (1990), the pollen-specific polygalaturonase gene promoter from brassica (U.S. Pat. No. 5,689,053) and maize (U.S. Pat. No. 5,412,085), the pollen-specific Lat52 and Lat59 promoters (Twell et al., Development 109:705-713 (1990), the anther-specific 1,3-beta-glucanase gene promoter (U.S. Pat. No. 5,955,653), and the Zea mays profilin multigene family anther and pollen promoters (Staiger et al., Plant J. 4:631-641 (1993). Promoter hybrids can be made that combine the functions of pollen, anther, tapetal cell and other male tissue specific expression into a single DNA molecule, for example, a fusion of the DNA sequences of the Osg6B promoter from rice and the P-Zm.Tas9 promoter (an element isolated from a corn tassel genomic library wherein the Zm.Tas9 coding sequence has homology to Zea mays profilin coding sequences) to create P-Os.Osg6B-Zm.Tas9 where the TATA box of the 5' Osg6B promoter sequence is modified or deleted to prevent transcription from that element. An additional promoter element can be combined with the rice-corn male promoter by the same method, for example, the wheat P-Ta.1674-19 promoter isolated from wheat sporophyll tissue, this triple promoter fusion provides broad spectrum monocot and dicot male tissue expression. The resulting promoter, P-Os.Osg6B-Zm.Tas9-Ta.1674-19 can be combined with the regulatory RNA binding protein coding sequences of the present invention to enable high levels of protein expression in the male tissues. These hybrid promoters are useful for providing expression at all stages of male tissue development.

Promoters that are preferentially expressed in a female tissue of the plant, include, but not limited to, the following promoters: the style and stigma specific promoters (EP 412006) and S-locus specific glycoprotein gene promoters; P26, P19, B200i4-2 (WO 9839462); DefH9 (WO 9828430); cysteine-rich extension-like protein gene promoters (Goldman et al., Plant Cell 4:1041-1051, 1992); ovule-specific O39, O126, O108 and O141 gene promoters from orchid (Nadeau et al., Plant Cell 8:213-239, 1996), the potato pistil-specific SK2 gene promoter (Ficher et al., Plant Mol. Biol. 35:425-431, 1997); and the rice pistil-specific RPC312 gene promoter and its monocot homolog (JP 11098986).

According to certain embodiments of the invention, expression of a conditional lethal gene is modulated in a tissue other than a reproductive tissue. For this purpose, one may choose from a number of promoters for genes with tissue- or cell-specific or -enhanced or induced expression. Examples of promoters that are preferentially expressed in leaves and other photosynthetically active tissues include the chloroplast glutamine synthetase GS2 promoter from pea (Edwards et al., Proc. Natl. Acad. Sci. U.S.A. 87:3459-3463, 1990), the chloroplast fructose-1,6-biphosphatase (FBPase) promoter from wheat (Lloyd et al., Mol. Gen. Genet. 225: 209-216, 1991), the nuclear photosynthetic ST-LS1 promoter from potato (Stockhaus et al., EMBO J. 8: 2445-2451, 1989), the serine/threonine kinase (PAL) promoter and the glucoamylase (CHS) promoter from Arabidopsis thaliana. Also reported to be active in photosynthetically active tissues are the ribulose-1,5-bisphosphate carboxylase (RBCS) promoter from eastern larch (Larix laricina), the promoter for the Cab gene, Cab6, from pine (Yamamoto et al., Plant Cell Physiol. 35: 773-778, 1994), the promoter for the Cab-1 gene from wheat (Fejes et al., Plant Mol. Biol. 15: 921-932, 1990), the promoter for the Cab-1 gene from spinach (Lubberstedt et al., Plant Physiol. 104:997-1006, 1994), the promoter for the Cab1R gene from rice (Luan et al., Plant Cell. 4:971-981, 1992), the pyruvate, orthophosphate dikinase (PPDK) promoter from Zea mays (Matsuoka et al., Proc. Natl. Acad. Sci. U.S.A. 90: 9586-9590, 1993), the promoter for the tobacco Lhcb1*2 gene (Cerdan et al., Plant Mol. Biol. 33:245-255, 1997), the Arabidopsis thaliana Suc2 sucrose-H$^+$ symporter promoter (Truemit et al., Planta. 196:564-570, 1995), and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention, such as the promoters for LhcB gene and PsbP gene from white mustard (Sinapis alba) (Kretsch et al., Plant Mol. Biol. 28: 219-229, 1995).

For the purpose of expression of agronomic genes of interest in sink tissues other than reproductive tissue of the plant, such as the tuber of the potato plant, the fruit of tomato, or the seed of soybean, canola, cotton, Zea mays, wheat, rice, and barley, it is preferred that the promoters utilized in the present invention have relatively high expression in these specific tissues. A number of promoters for genes with tuber-specific or -enhanced expression are known, including the class I patatin promoter (Bevan et al., EMBO J. 8:1899-1906 (1986); Jefferson. et al., Plant Mol. Biol. 14:995-1006, 1990), the promoter for the potato tuber ADPGPP genes, both the large and small subunits, the sucrose synthase promoter (Salanoubat et al., Gene 60:47-56, 1987); Salanoubat et al., Gene 84:181-185, 1989), the promoter for the major tuber proteins including the 22 kDa protein complexes and proteinase inhibitors (Hannapel, Plant Physiol. 101:703-704, 1993), the promoter for the granule bound starch synthase gene (GBSS) (Visser et al., Plant Mol. Biol. 17:691-699, 1991), and other class I and II patatin promoters (Koster-Topfer et al., Mol. Gen. Genet. 219:390-396 (1989); Mignery et al., Gene 62:27-44, 1988).

Other promoters can also be used to express a protein in specific tissues, such as seeds or fruits. The promoter for β-conglycinin (Chen et al., Dev. Genet. 10:112-122, 1989) or other seed-specific promoters such as the napin and phaseolin promoters, can be used. The zeins are a group of storage proteins found in Zea mays endosperm. Genomic clones for zein genes have been isolated (Pedersen et al., Cell 29:1015-1026, 1982), and the promoters from these clones, including the 15 kDa, 16 kDa, 19 kDa, 22 kD, 27 kDa, and gamma genes, could also be used. Other promoters known to function, for example, in Zea mays include the promoters for the following genes: waxy, Brittle, Shrunken 2, Branching enzymes I and II, starch synthases, debranching enzymes, oleosins, glutelins, and sucrose synthases. A particularly preferred promoter for Zea mays endosperm expression is the promoter for the glutelin gene from rice, more particularly the Osgt-1 promoter (Zheng et al., Mol. Cell. Biol. 13:5829-5842, 1993). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1 gene. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., Plant Mol. Biol. 25:587-596, 1994). Expression in root tissue could also be accomplished by utilizing the root specific subdomains of the CaMV35S promoter that have been identified (Lam et al., Proc. Natl. Acad. Sci. U.S.A. 86: 7890-7894, 1989). Other root cell specific promoters include those reported by Conkling et al. (Plant Physiol. 93: 1203-1211, 1990).

Germination and early seedling growth promoter specificity could be provided to drive expression of a conditional lethal transgene in a germination and early seedling growth specific or intensive process. Germination and early seedling growth promoters could be used specifically to affect a gene function that is essential for germination, but its gene expression is not limited to this time in the plant growth cycle. The preferred germination specific promoter would be most highly expressed in the appropriate tissues and cells at the appropriate developmental time to inhibit the germination enzyme or gene product only during germination or early seedling growth. Tissues and cells that comprise the germination and early seedling growth stages of plants may include: the radical, hypocotyl, cotyledons, epicotyl, root tip, shoot tip, meristematic cells, seed coat, endosperm, true leaves, internodal tissue, and nodal tissue. Germination-enhanced promoters have been isolated from genes encoding the glyoxysomal enzymes isocitrate lyase (ICL) and malate synthase (MS) from several plant species (Zhang et al, Plant Physiol. 104: 857-864, 1994); Reynolds and Smith, Plant Mol. Biol. 27: 487-497, 1995); Comai et al, Plant Physiol. 98: 53-61, 1992). Other promoters include SIP-seedling imbibition protein (Heck, G., Ph.D. Thesis, 1992, Washington University, St. Louis, Mo.) and others such as a cysteine endopeptidase promoter (Yamauchi et al, Plant Mol. Biol. 30: 321-329, 1996). Additionally, promoters could be isolated from other genes whose mRNAs appear to accumulate specifically during the germination process, for example class I β-1,3-glucanase B from tobacco (Vogeli-Lange et al., Plant J. 5: 273-278, 1994); canola cDNAs CA25, CA8, AX92 (Harada et al., Mol. Gen. Genet. 212: 466-473, 1988); Dietrich et al., J. Plant Nutr. 8: 1061-1073, 1992), lipid transfer protein (Sossountzove et al, Plant Cell 3: 923-933, 1991); or rice serine carboxypeptidases (Washio et al., Plant Phys. 105: 1275-1280, 1994); and repetitive proline rich cell wall protein genes (Datta et al., Plant Mol. Biol. 14: 285-286, 1990).

Chimeric promoters that express in plants include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant. Mol. Biol. 15:373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Chimeric promoters that contain regulatory elements from heterologous sources can be constructed by those skilled in the art to direct the expression of the agronomic gene of interest and the conditional lethal gene to the desired tissue or cell in the amounts necessary to achieve the desired phenotype.

The 5' UTR can be derived from a promoter selected to express a selected protein-coding region and can be specifically modified if desired so as to increase translation of mRNA. For a review of optimizing expression of transgenes, see Koziel et al., Plant Mol. Biol. 32:393405, 1996). The 5' non-translated regions can be a native sequence obtained, for example, from eukaryotic (e.g., plant) genes, from bacterial or viral genes that are expressed in plant cells (e.g., genes from *Agrobacterium tumefaciens* (AGRTU), or from a chimeric or synthetic gene sequence. The operator that is bound by an RNA-binding protein is inserted into the 5, UTR of the first DNA molecule positioned with respect to the 5' end of the mRNA and the start site for protein translation such that binding of an RNA-binding protein to the operator inhibits or substantially reduces translation of an operably linked protein-coding sequence.

The aforesaid described genetic elements and other regulatory elements of similar function may be substituted when appropriate by those skilled in the art of plant molecular biology to provide necessary function to the plant expression cassettes of the present invention.

A vector may also include a screenable or scorable marker gene plant expression cassettes. Screenable or scorable marker gene cassettes may be used in the present invention to monitor expression in segregating cells or progeny or loss of expression. Exemplary markers include a β-glucuronidase or uidA gene (GUS) that encodes an enzyme for that various chromogenic substrates are known (Jefferson et al., Plant Mol. Biol, Rep. 5:387-405 (1987); Jefferson et al., EMBO J. 6:3901-3907, 1987); an R-locus gene, that encodes a product that regulates the production of anthocyanin pigments (red color) in plant tissues (Dellaporta et al., Stadler Symposium 11:263-282, 1988); a β-lactamase gene (Sutcliffe et al., Proc. Natl. Acad. Sci. (U.S.A.) 75:3737-3741, 1978); a gene that encodes an enzyme for that various chromogenic substrates are known (e.g., PADAC, a chromogenic cephalosporin); a luciferase gene (Ow et al., Science 234:856-859, 1986); a xylE gene (Zukowsky et al., Proc. Natl. Acad. Sci. (U.S.A.) 80:1101-1105, 1983) that encodes a catechol dioxygenase that can convert chromogenic catechols; an α-amylase gene (Ikatu et al., Bio/Technol. 8:241-242, 1990); a tyrosinase gene (Katz et al., J. Gen. Microbiol. 129:2703-2714, 1983) that encodes an enzyme capable of oxidizing tyrosine to DOPA and dopaquinone that in turn condenses to melanin; green flourescence protein (Elliot et al., Plant cell Rep. 18:707-714, 1999) and an α-galactosidase.

*Agrobacterium*-mediated transfer is the preferred method of the present invention. The use of *Agrobacterium*-mediated plant integrating vectors to introduce DNA into plant cells is well known in the art. See, for example the methods described by Fraley et al., Bio/Technology 3:629-635 (1985) and Rogers et al., Methods Enzymol. 153:253-277 (1987). The region of DNA to be transferred is defined by the border sequences (T-DNA), and intervening DNA usually comprising a plant expression cassette is usually inserted into the plant genome as described by Spielmann et al., Mol. Gen. Genet. 205:34 (1986).

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203, 1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., Methods Enzymol. 153:253-277, 1987). These base Agro-vectors, as well as others known in the art can be used to incorporate the DNA constructions and methods of the present invention. In addition, *Agrobacterium* containing both armed and disarmed Ti genes can be used for the transformations.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Back-crossing to a parental plant and out-crossing with a non-transgenic plant are contemplated, as is vegetative propagation. Descriptions of other breeding methods that are commonly used for different traits and crops can be found in Fehr, In: *Breeding Methods for Cultivar Development*, Wilcox J. ed., American Society of Agronomy, Madison Wis. (1987).

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et al, Bio/Technology 6:923 (1988), Christou et al., Plant Physiol. 87:671-674, 1988); *Brassica* (U.S. Pat. No. 5,463,174); peanut (Cheng et al., Plant Cell Rep. 15:653-657 (1996), McKently et al, Plant Cell Rep. 14:699-703, 1995); and pea (Grant et al., Plant Cell Rep. 15:254-258, 1995), herein incorporated by reference in their entirety.

Transformation of monocotyledons using electroporation, particle bombardment, and *Agrobacterium* have also been reported. Transformation and plant regeneration have been achieved in asparagus (Bytebier et al., Proc. Natl. Acad. Sci. (USA) 84:5354-5349, 1987); barley (Wan et al., Plant Physiol 104:37-48 (1994); *Zea mays* (Rhodes et al., Science 240:204-207 (1988), Gordon-Kamm et al., Plant Cell 2:603-618 (1990), Fromm et al., Bio/Technology 8:833-839 (1990), Koziel et al., Bio/Technology 11: 194-200 (1993), Armstrong et al., Crop Science 35:550-557 (1995); oat (Somers et al., Bio/Technology 10:1589-1594 (1992); orchard grass (Horn et al., Plant Cell Rep. 7:469-472 (1988); rice (Toriyama et al., Theor Appl. Genet. 205:34-(1986), Part et al., Plant Mol. Biol. 32:1135-1148, (1996), Abedinia et al., Aust. J. Plant Physiol. 24:133-141 (1997), Battraw et al., Plant Mol. Biol. 15:527-538 (1990), Christou et al., Bio/Technology 9:957-962 (1991); rye (De la Pena et al., Nature 325:274-276 (1987); sugarcane (Bower et al., Plant J. 2:409-416 (1992); tall fescue (Wang et al., Bio/Technology 10:691-696 (1992); and wheat (Vasil et al., Bio/Technology 10:667-674 (1992); U.S. Pat. No. 5,631,152), herein incorporated by reference in their entirety.

Assays for gene expression based on the transient expression of cloned nucleic acid vectors have been developed by introducing the nucleic acid molecules into plant cells by polyethylene glycol treatment, electroporation, or particle bombardment (Marcotte et al., Nature 335:454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522, 1990). Transient expression systems may be used to functionally dissect gene constructs (see generally, Mailga et al., Methods in Plant Molecular Biology, Cold Spring Harbor Press, 1995). It is understood that any of the nucleic acid molecules of the present invention can be introduced into a plant cell in a permanent or transient manner in combination with other genetic elements such as promoters, leaders, transit peptide sequences, enhancers, introns, 3' nontranslated regions and other elements known to those skilled in the art that are useful for control of transgene expression in plants.

In addition to the above discussed procedures, practitioners are familiar with the standard resource materials that describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Mailga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Clark et al., Plant Molecular Biology: A Laboratory Manual, Springer, New York (1997); and Innis et al., PCR Protocols: A Guide to Methods and Applications, Academic Press: San Diego, (1990).

Examples of suitable structural genes of agronomic interest envisioned by the present invention would include but are not limited to one or more genes for insect tolerance, such as a *Bacillus thuringiensis* (B.t.) gene, disease tolerance such as genes for fungal disease control, virus disease control, bacteria disease control and nematode disease control; herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 9931248 herein incorporated by reference in its entirety, U.S. Pat. No. 5,689,052 herein incorporated by reference in its entirety, U.S. Pat. Nos. 5,500,365 and 5,880,275, herein incorporated by reference in its entirety. The herbicide tolerance polynucleotide sequences include, but are not limited to polynucleotide sequences encoding for proteins involved in herbicide tolerance encoding for 5-enolpyruvylshikimate-3-phosphate synthase (EPSPS, described in U.S. Pat. Nos. 5,627,061, and 5,633,435, herein incorporated by reference in its entirety; Padgette et al. (1996) *Herbicide Resistant Crops*, Lewis Publishers, 53-85, and in Penaloza-Vazquez, et al. (1995) *Plant Cell Reports* 14:482-487) and aroA (U.S. Pat. No. 5,094,945) for glyphosate tolerance; bromoxynil nitrilase (Bxn) for Bromoxynil tolerance (U.S. Pat. No. 4,810,648); phytoene desaturase (crtI (Misawa et al, (1993) *Plant Journal* 4:833-840, and (1994) *Plant Jour* 6:481-489) for tolerance to norflurazon, acetohydroxyacid synthase (AHAS, Sathasiivan et al. (1990) *Nucl. Acids Res.* 18:2188-2193); and the bar gene for tolerance to glufosinate (DeBlock, et al. (1987) *EMBO J.* 6:2513-2519. Herbicides for which transgenic plant tolerance has been demonstrated and the method of the present invention can be applied include, but are not limited to: glyphosate, glufosinate, sulfonylureas, imidazolinones, bromoxynil, delapon, cyclohezanedione, protoporphyrinogen oxidase inhibitors, and isoxaslutole herbicides.

DNA Constructs

Figure 8:
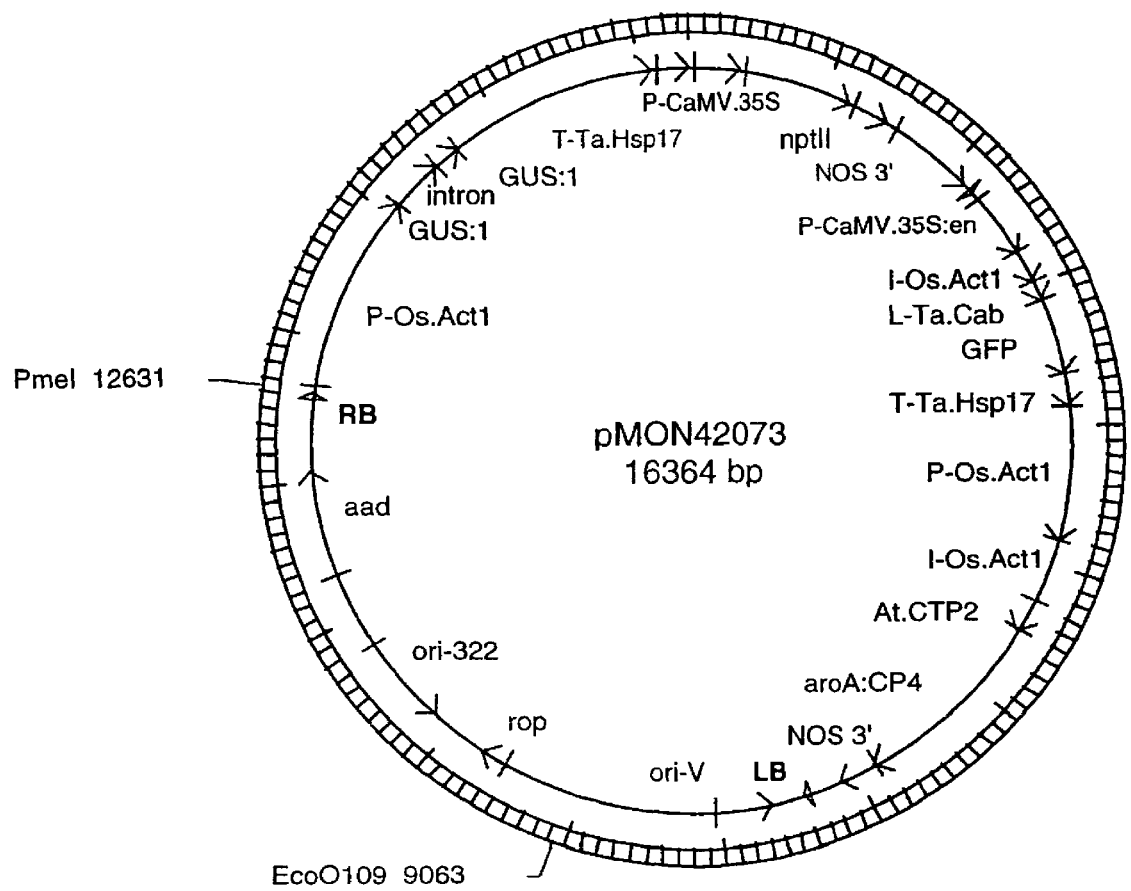

DNA constructs in an aspect of the present invention contain at least two T-DNAs and the DNA segments residing between the two T-DNAs. Each T-DNA comprises an *Agrobacterium* right border (RB) and left border (LB) sequence, and contain 1 or more plant expression cassettes. It is common to construct a T-DNA containing multiple plant expression cassettes. FIG. 1, pMON42061 illustrates a single T-DNA construct containing 3 plant expression cassettes (P-FMV.34S/At.CTP2/aroA:CP4/E93'; PCaMV.35S/nptII/Nos 3'; and P-CaMV.35S:en/GUS:1/intron/GUS:1/Nos 3') and FIG. 8, pMON42073 illustrates a single T-DNA construct containing 4 plant expression cassettes (P-Os.Act1/GUS:1/intron/GUS:1/T-TaHsp17; P-CaMV.35S/nptII/Nos3'; P-CaMV.35S:en/I-Os.Act1/L-Ta.Cab/GFP/T-Ta.Hsp17, P-Os.Act1/I-OsAct1/At.CTP2/aroA:CP4/Nos 3' between a RB and a LB. As illustrated in pMON42061 and pMON42073 multiple expression cassettes containing agronomic genes of interest, selectable and scorable marker genes can be included in a single T-DNA. These constructs also have unique endonuclease restriction sites for the further engineering of the construct, for example, the FseI site of pMON42061 and the EcoO109 site of pMON42073. Additional endonuclease restriction sites that can be used for further engineering of the DNA constructs of the present invention include, but are not limited to, Not1, Pme1, Xho1, Sma1, HindIII, and Nhe1. Those of ordinary skill in the art of plant molecular biology can remove, replace, modify or add restriction sites and polylinker DNA molecules to provide modification of the DNA constructs that enhance the mobility of DNA segments, genetic elements, expression cassettes, and T-DNAs into and out of the DNA constructs.

Figure 2:
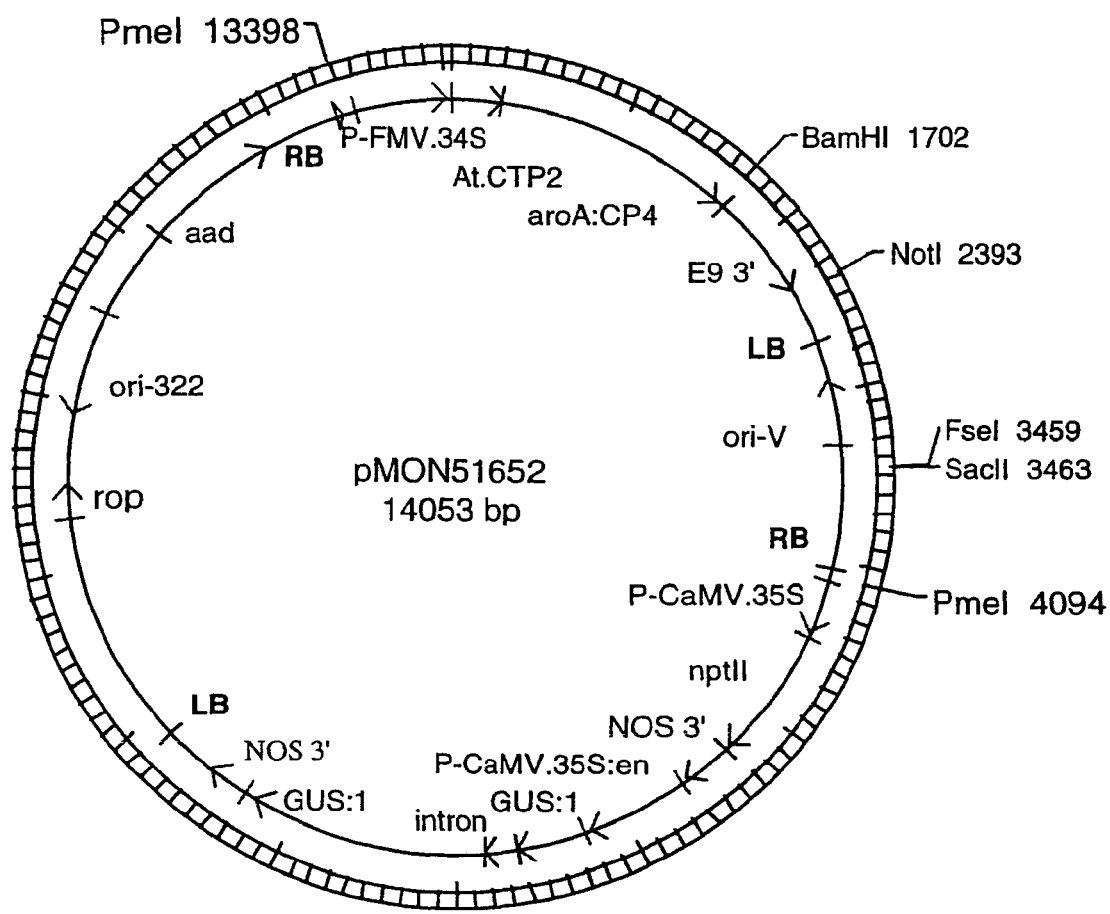
Figure 6:
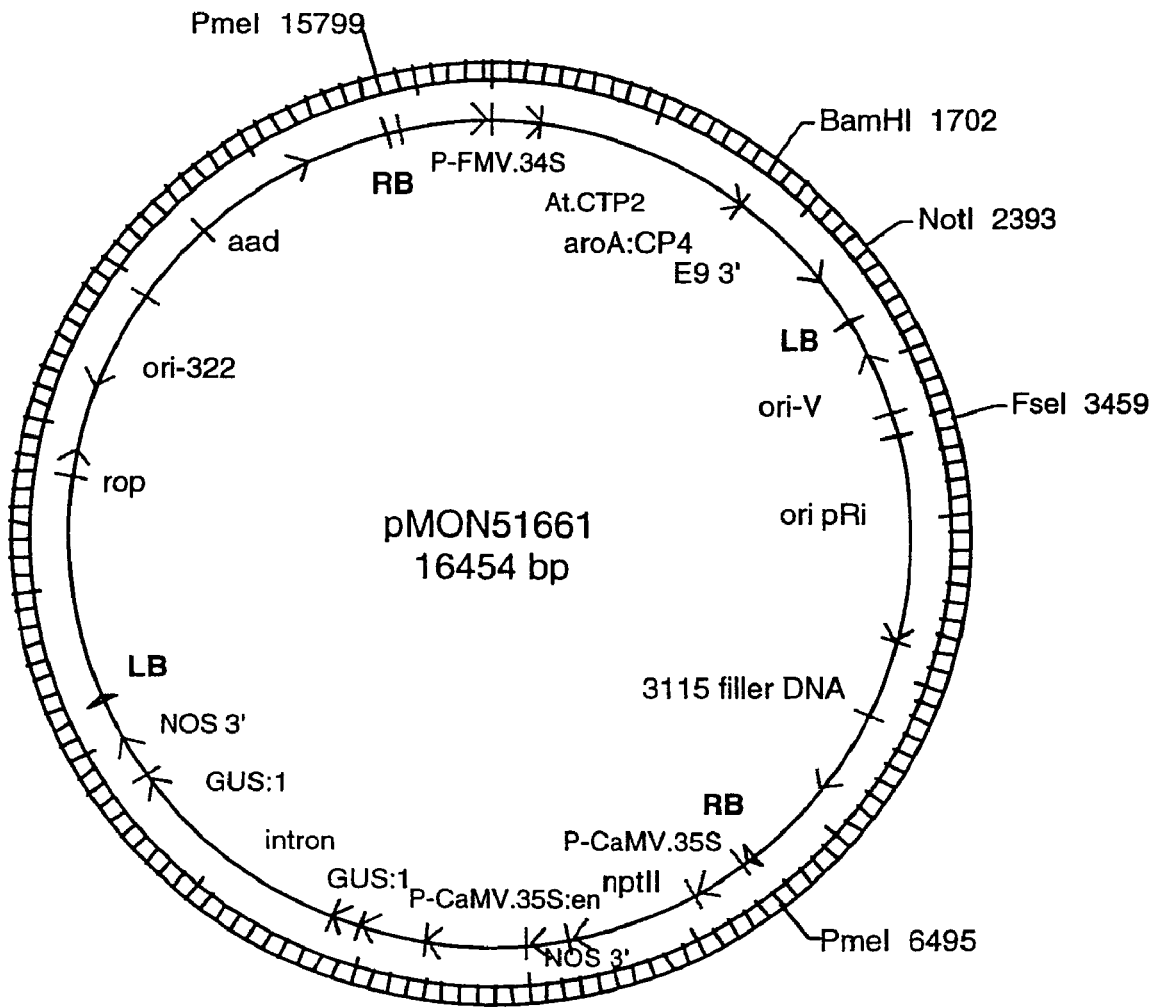

A DNA construct of this aspect of the present invention contains at least two T-DNAs allowing for a multitude of combinations of plant expression cassettes. Also, the DNA segments between the T-DNAs can be used to insert various plant and bacterial expression cassettes. The DNA constructs that comprise the Two T-DNAs can include various modifications that decrease T-DNA insert complexity and increase independent segregation. These include the length of the DNA segments residing between the T-DNAs in a DNA construct. This length is a variable that can be manipulated to enhance the separate integration of the T-DNAs in the plant genome and low copy number of the insertions. The range of the length of the DNA segments can be from about 1000 nucleotide base pairs (1 kb) to about 15 kb. The DNA construct, pMON51652, illustrated in FIG. 2 is an example of a construct with a small DNA segment spacer of about 1400 base pairs and a larger segment of about 4.5 kb. The DNA construct, pMON51661, illustrated in FIG. 6 is an example of a construct with DNA segment spacers of about 4 kb. Both of these constructs contain a unique Not1 site for insertion of additional plant expression cassettes of agronomic genes of interest and a unique Fse1 site for insertion of a conditional lethal gene expression cassette.

Figure 3:
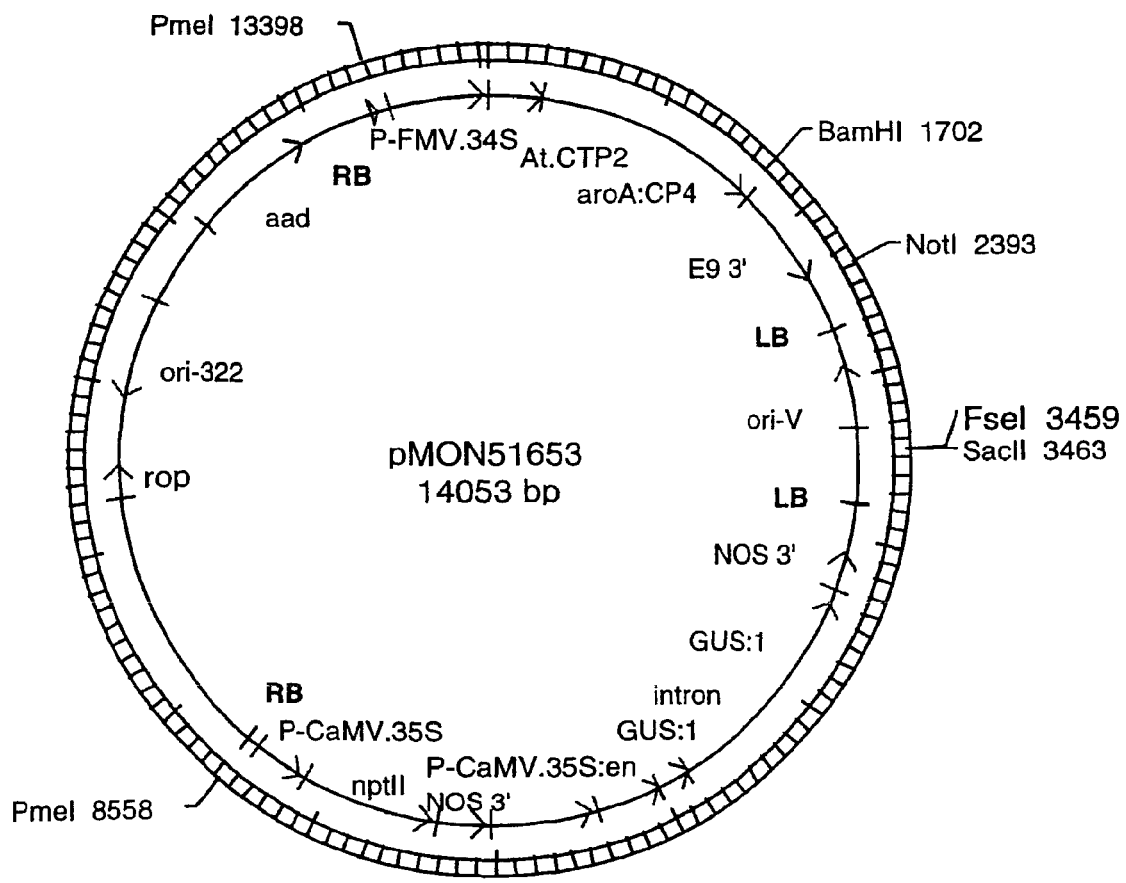
Figure 10:
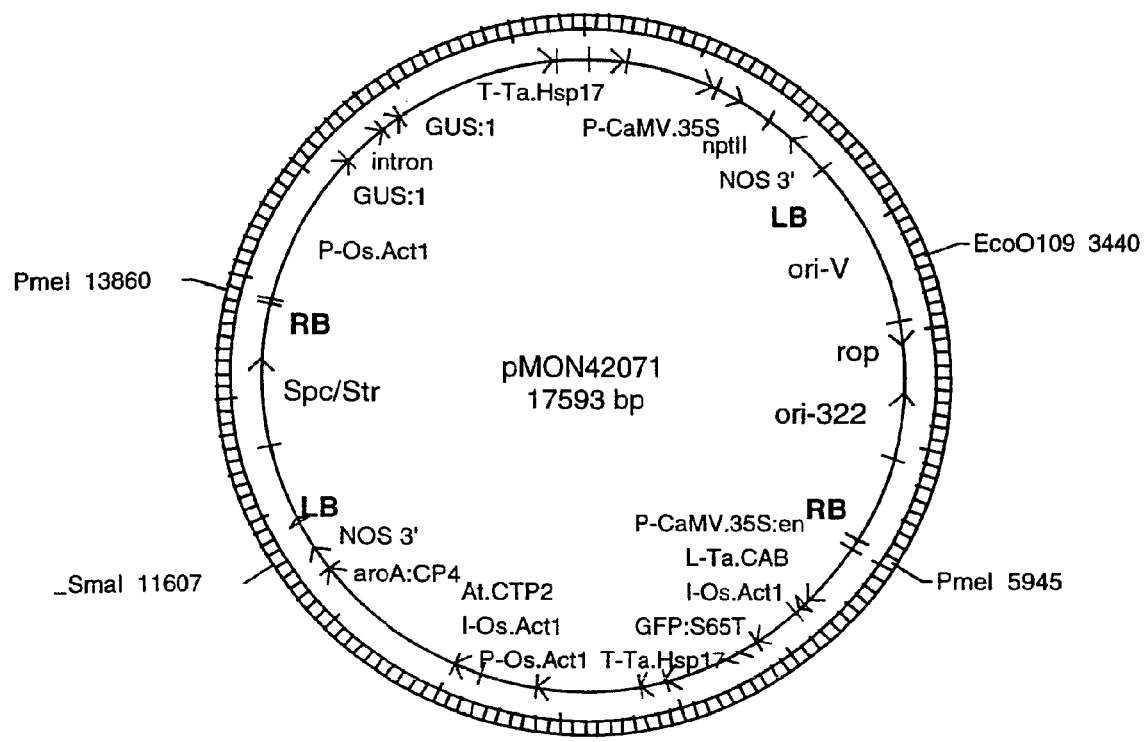
Figure 11:
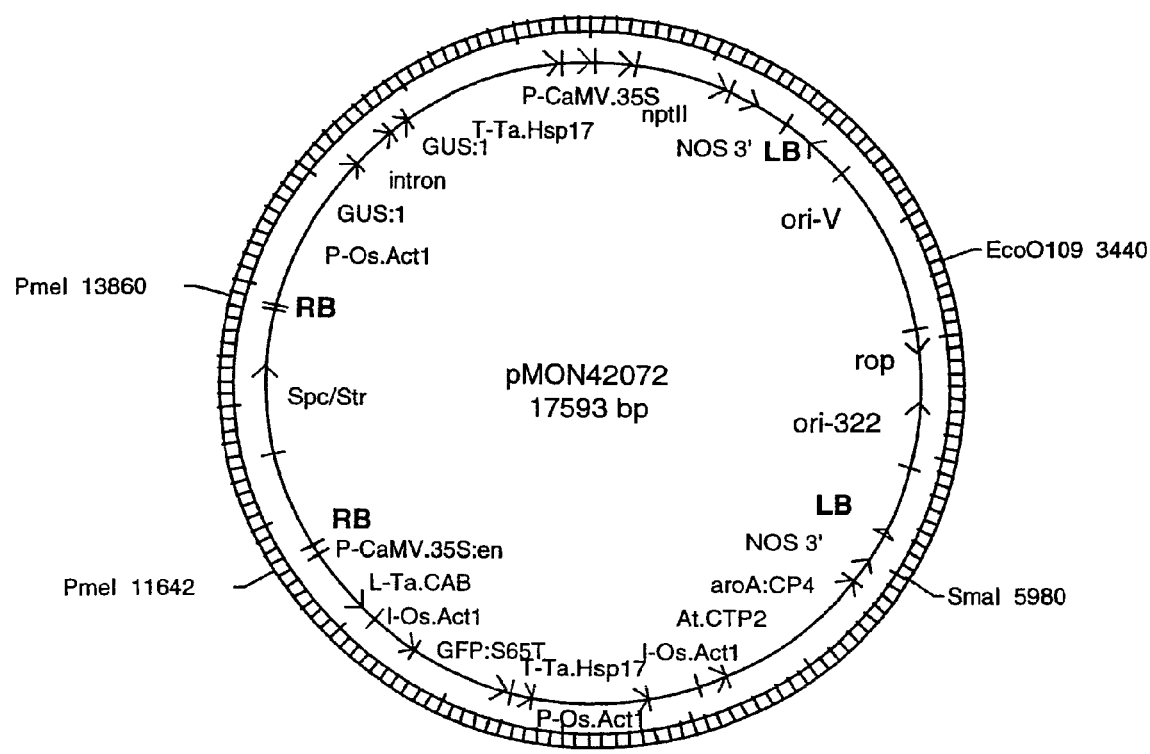

Another modification is the orientation of the border sequences of the T-DNAs, this can also affect the efficiency of independent segregation of the T-DNAs. In pMON51652, the clockwise orientation of the T-DNAs is RB-LB for T-DNA 1 that contains the plant expression cassette expressing the aroA:CP4 gene (glyphosate tolerance), and RB-LB for T-DNA 2 that contains the plant expression cassettes expressing nptII (kanamycin tolerance) and GUS: 1 (β-glucuronidase, visual marker). The pMON51652 construct has a unique FseI and SacII endonuclease enzyme site in the DNA segment that can be used to insert plant expression cassettes that provide conditional lethal gene products to further enhance independent segregation of the T-DNAs. The DNA construct, pMON42071, illustrated in FIG. 10, is similar in design to pMON51652 except that it contains in its T-DNAs genetic elements designed for enhanced expression in monocot plants. The clockwise orientation of the borders of the T-DNAs in this construct is RB-LB for T-DNA 1 (GUS; nptII) and RB-LB for T-DNA 2 (GFP; aroA:CP4). The DNA construct, pMON51653, illustrated in FIG. 3, has a clockwise orientation of the border sequences of RB-LB for T-DNA 1 (aroA:CP4) and LB-RB for T-DNA 2 (GUS; nptII). The pMON42072 construct, illustrated in FIG. 11, is similar in design to pMON51653 except that it contains in its T-DNAs genetic elements designed for enhanced expression in monocot plants, its T-DNAs have a clockwise orientation of the border sequences of RB-LB for T-DNA 1 (GUS; nptII) and LB-RB for T-DNA 2 (aroA:CP4; GFP). The constructs has a unique endonuclease enzyme sites in the DNA segment that can be used to insert plant expression cassettes that provide the conditional lethal gene products to further enhance independent segregation of the T-DNAs. Constructs that have two T-DNAs orientated RB-first T-DNA-LB, LB-second T-DNA-RB can show an increase in independent segregation of the T-DNAs, reduced occurrence of the construct DNA segments and an increase in detection of expression of the transgenes from each of the T-DNAs.

Figure 4:
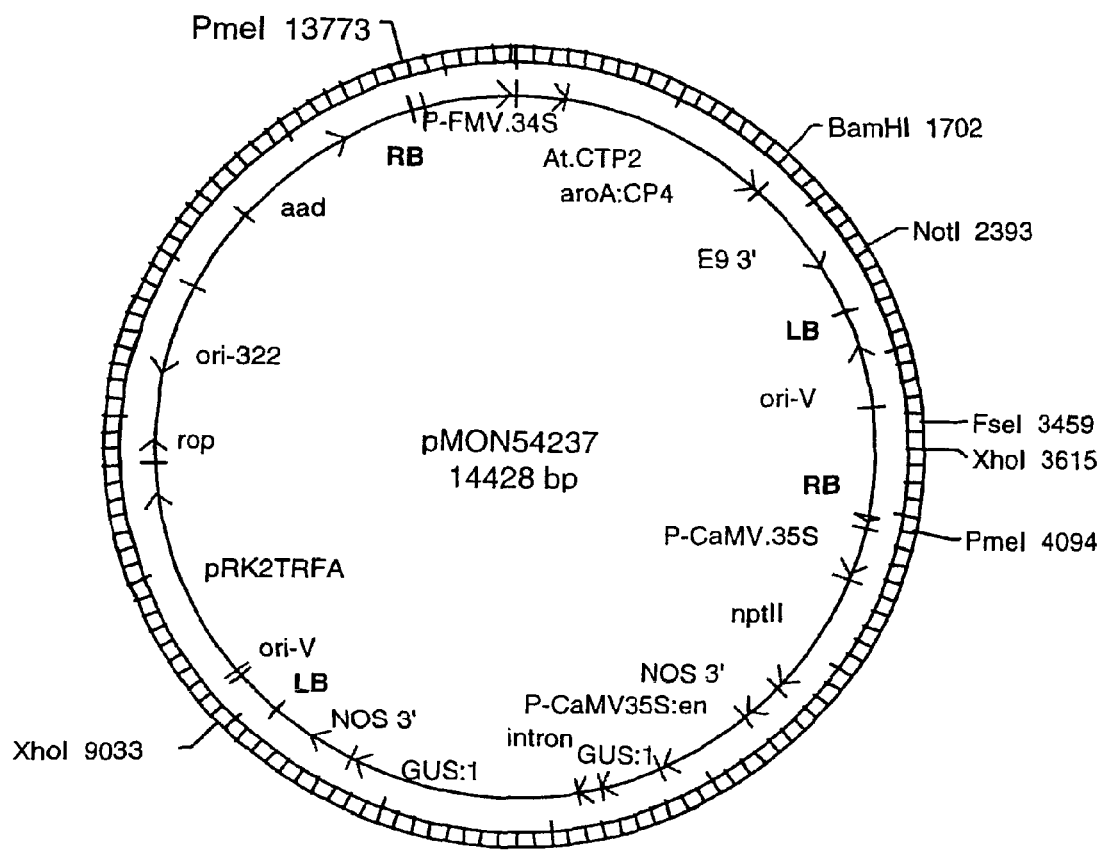
Figure 7:
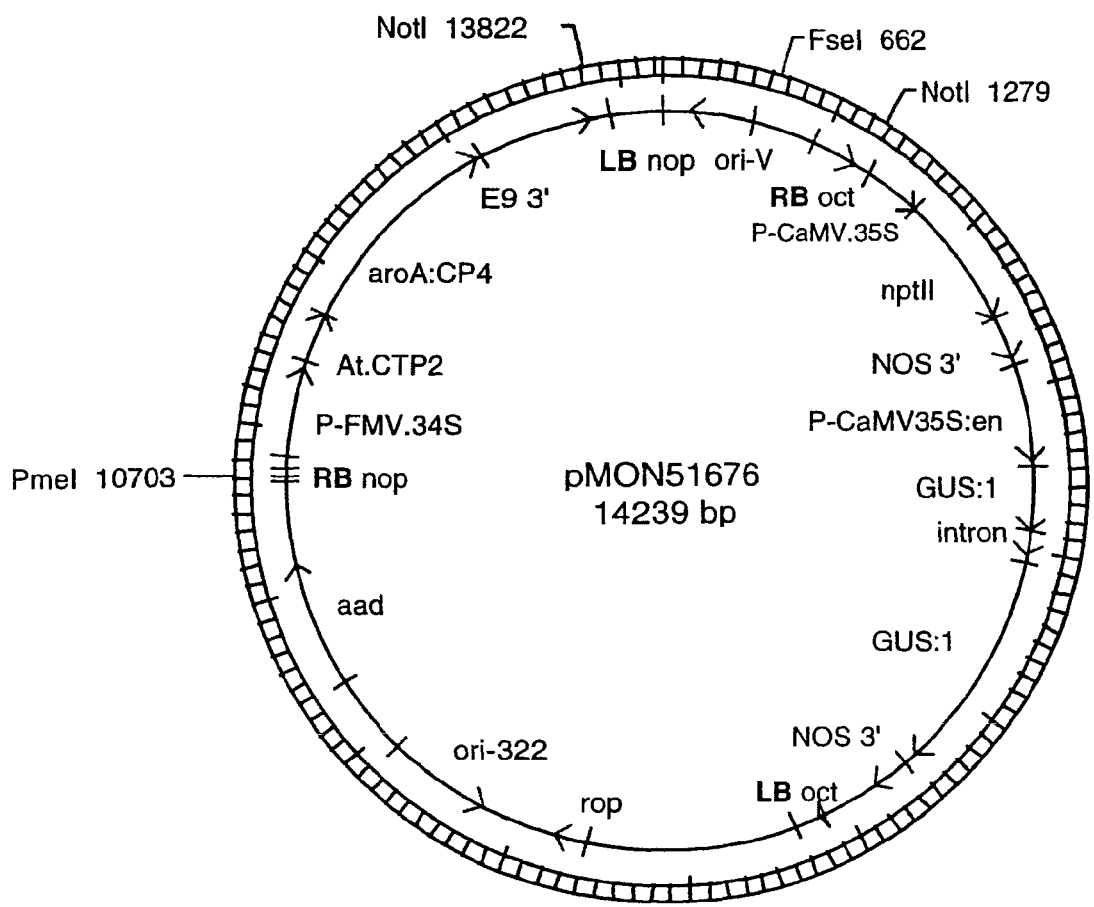

The DNA constructs of the present invention are transformed into plant cells by an *Agrobacterium* mediated transformation methods. Various strains of *Agrobacterium* are hosts for the DNA constructs and function to transfer the T-DNAs of the constructs dependent on the presence of compatible transfer elements. The element trfA (pRK2TRFA) provides complementation of the transfer function for strain LBA4404 (an octopine strain) and when inserted into pMON51653 to create pMON54237 (FIG. 4) will permit the T-DNAs of this construct to be transferred into plants by LBA4404. The construct, pMON54237 contains a unique Not1 site for insertion of additional plant expression cassettes of agronomic genes of interest and a unique Fse1 site for insertion of a conditional lethal gene expression cassette. For comparison, pMON51653 and pMON51652 are transferred into plants via strain ABI (a nopaline strain). *Agrobacterium* strain differences is a modification of the T-DNA transfer method that can influence the efficiency of T-DNA transfer and the segregation of the T-DNAs in the transformed plant. The border regions are derived from octopine or nopaline strains of *Agrobacterium*. The construct, pMON51676 (FIG. 7) contains two T-DNAs, the T-DNA 1 contains a RB nop and a LB nop region from a nopaline strain, and T-DNA 2 contains a RB oct and a LB oct region from an octopine strain. These arrangement of T-DNA borders in combination with homologous and heterologous *Agrobacterium* nopaline and octopine strains will allow for more control of the T-DNA processing and provides a differential that can be manipulated for the preferential insertion of a T-DNA. The different strains of disarmed *Agrobacterium* that serve as the host for the DNA constructs, i.e., nopaline and octopine strains when combined with T-DNAs with that vary in the origin of the border sequences can provide enhancement to insertion of the T-DNAs when these strains are mixed together in a co-transformation *Agrobacterium* mediated plant transformation method. In this aspect of the invention, the DNA constructs that are used in a co-transformation method with different strains may contain only one T-DNA and a conditional lethal gene residing in the DNA segment. Additionally, DNA constructs can be selected for use in a co-transformation method with different strains, wherein at least one of the DNA constructs does not contain a conditional lethal gene.

Figure 5:
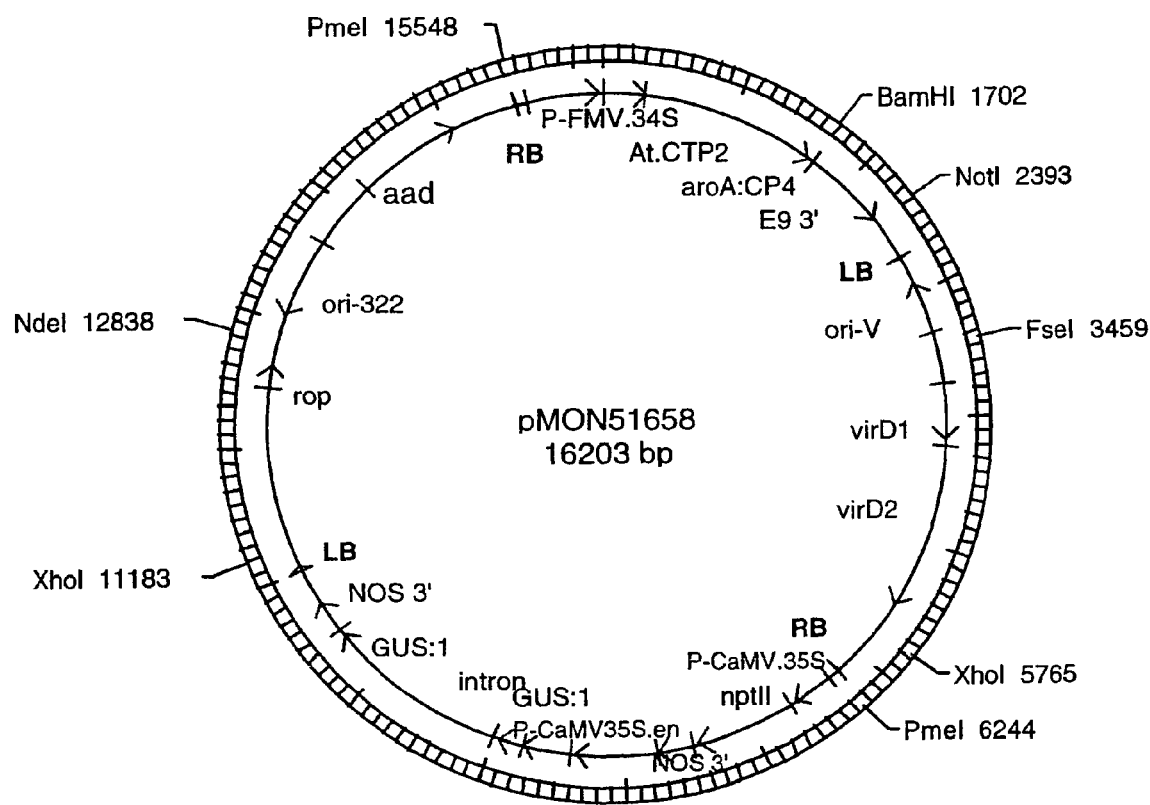
Figure 9:
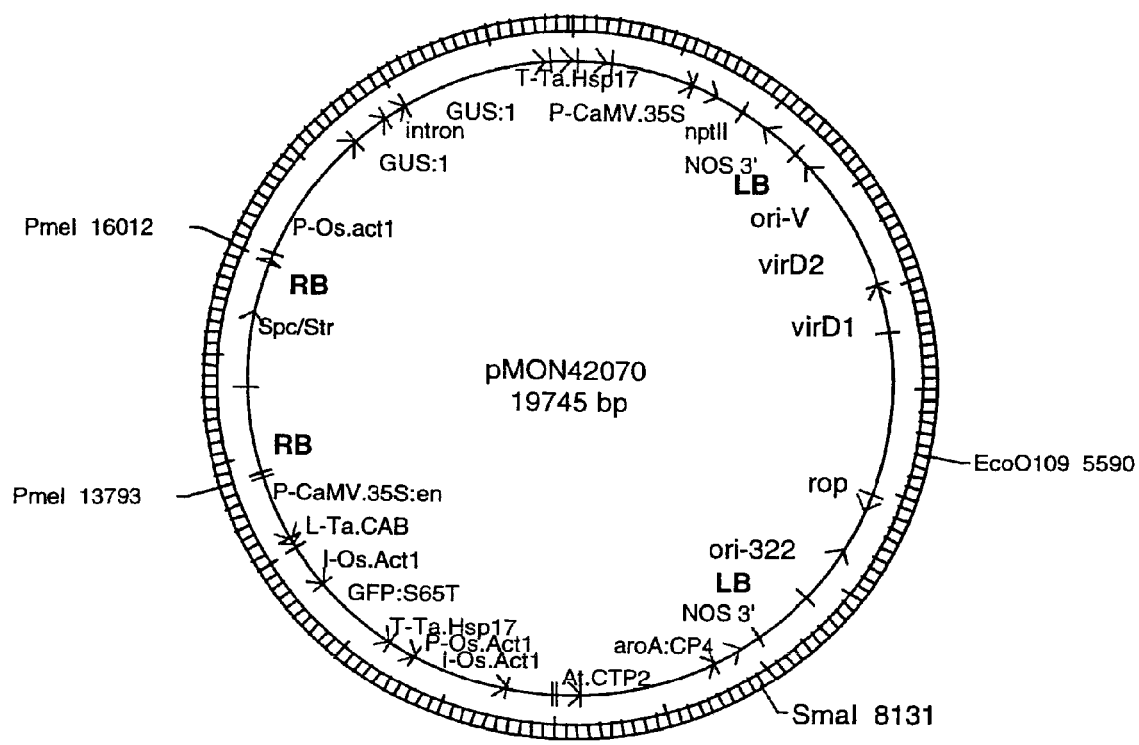

The present invention also provides modification in a DNA construct to enhance the integrity of the T-DNAs and reduce the often observed left border readthrough. The *Agrobacterium* virulence genes, virD1 and virD2 encode for endonucleases that nick within the 25 bp RB and LB nucleotide sequences, providing a template with clearly defined 5' and 3' ends. The inclusion of the virD1 and virD2 genes in the DNA segments outside of the T-DNAs will increase efficiency of nicking at the borders, particularly the LB, and prevent border readthrough during plant genomic integration. The prevention of border readthrough will increase the integrity of the T-DNA and enhance the segregation of the T-DNAs in the plant genome and therefore the quality of transformed events. The expression of virD1 and virD2 genes is by the native virD promoter which has been PCR amplified and placed upstream of the coding regions. The construct, pMON51658 (FIG. 5) contains the virD1 and virD2 expression cassettes in the DNA segment located between T-DNA 1 (aroA:CP4) and T-DNA 2 (nptII; GUS) of this construct. Additional unique endonuclease sites, Nde1 and Fse1 are positioned to permit the insertion of conditional lethal gene expression cassettes. pMON42070 (FIG. 9) contains within its T-DNAs, plant expression cassettes that contain genetic elements for enhanced expression in monocot plants, the virD1 and virD2 genes, and a unique endonuclease site EcoO109 for insertion of conditional lethal gene expression cassettes. The constructs containing the virD1 and virD2 genes and the conditional lethal genes will have the properties of enhanced termination at the border sequences and a method to eliminate any plants that have the T-DNAs linked at the same locus. Additional plant expression cassettes containing agronomic genes of interest can be inserted into the construct at the endonuclease sites residing within the T-DNAs as illustrated in FIGS. 5 and 9. *Agrobacterium* mediated transformation of dicot and monocot plant cells with genetic elements designed for enhanced expression in these plants are known to those skilled in the art of plant molecular biology. These genetic elements in operable linkage contained within the two T-DNAs of a DNA construct and containing a conditional lethal gene is within the scope of the present invention. In subsequent generations of the plants transformed with these DNA constructs, the plants are treated with a protoxin that is processed by the conditional lethal gene product into a phytotoxin. Surviving plants contain T-DNAs that can be genetically separated in breeding populations.

Conditional Lethal Gene Elements

Figure 12:
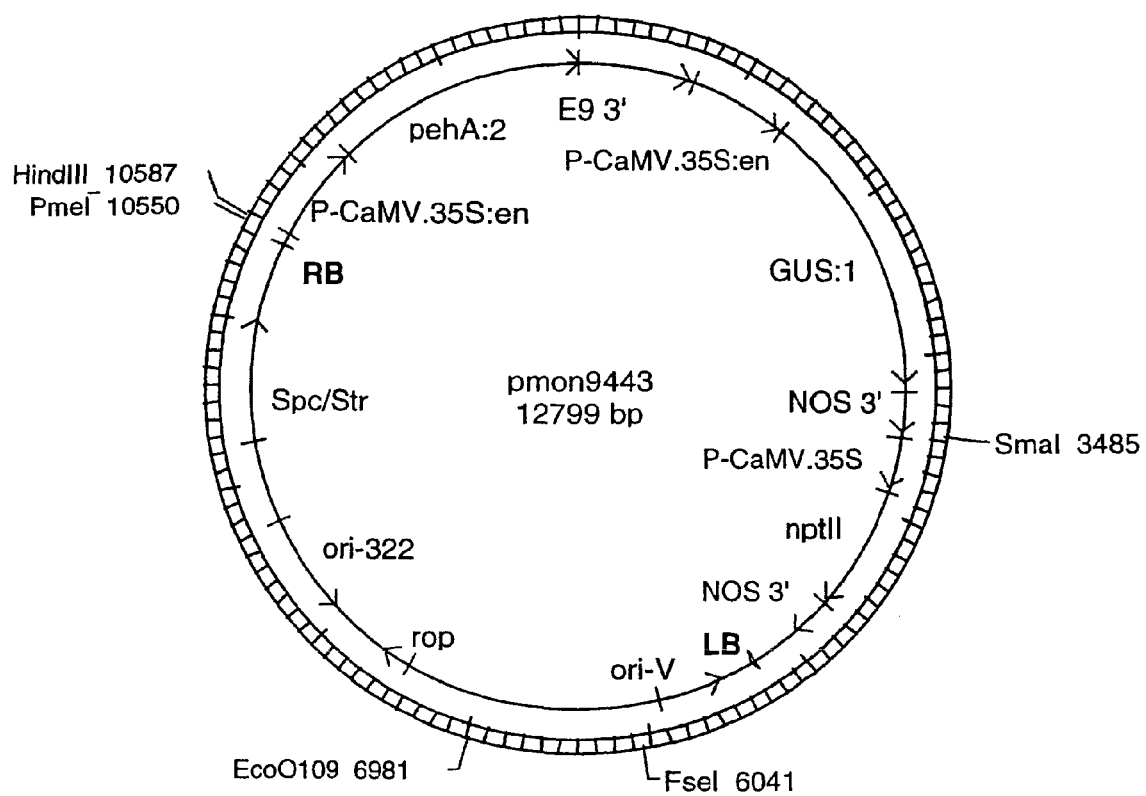
Figure 13:
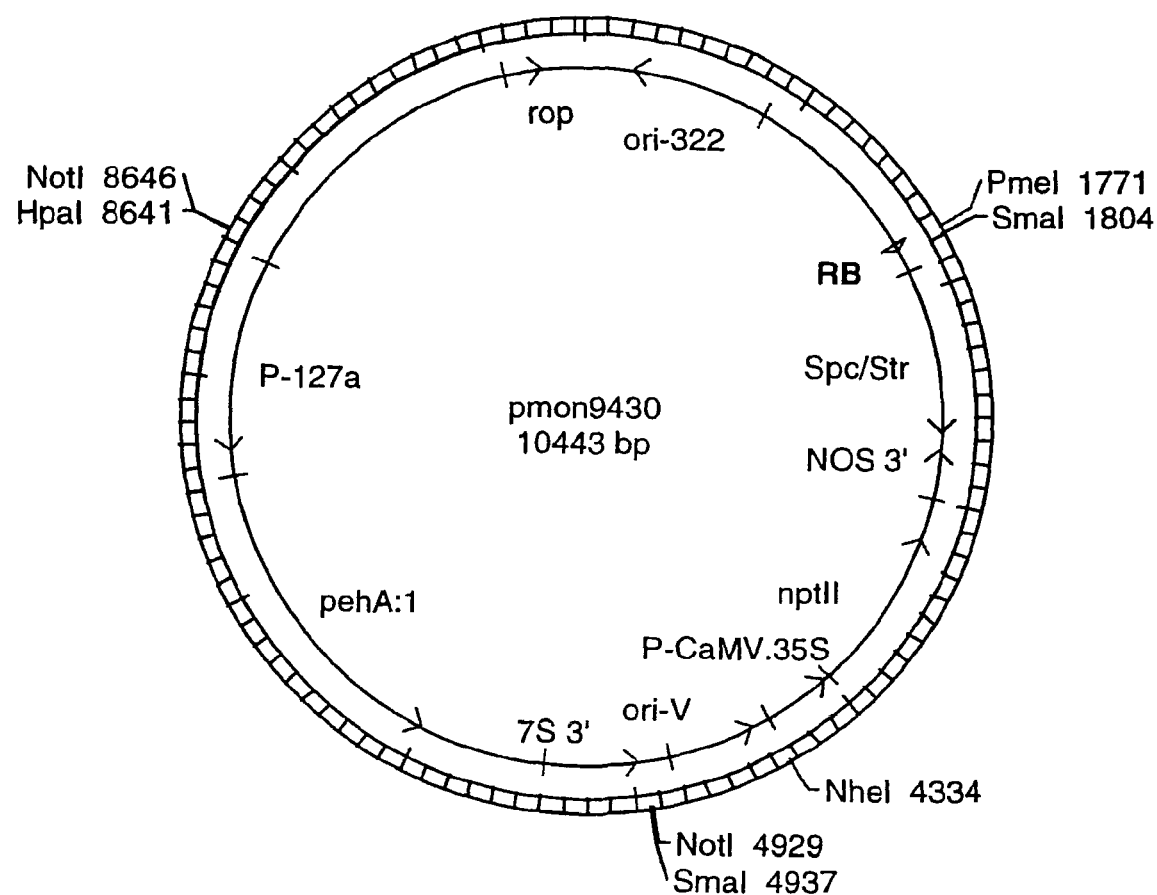
Figure 14:
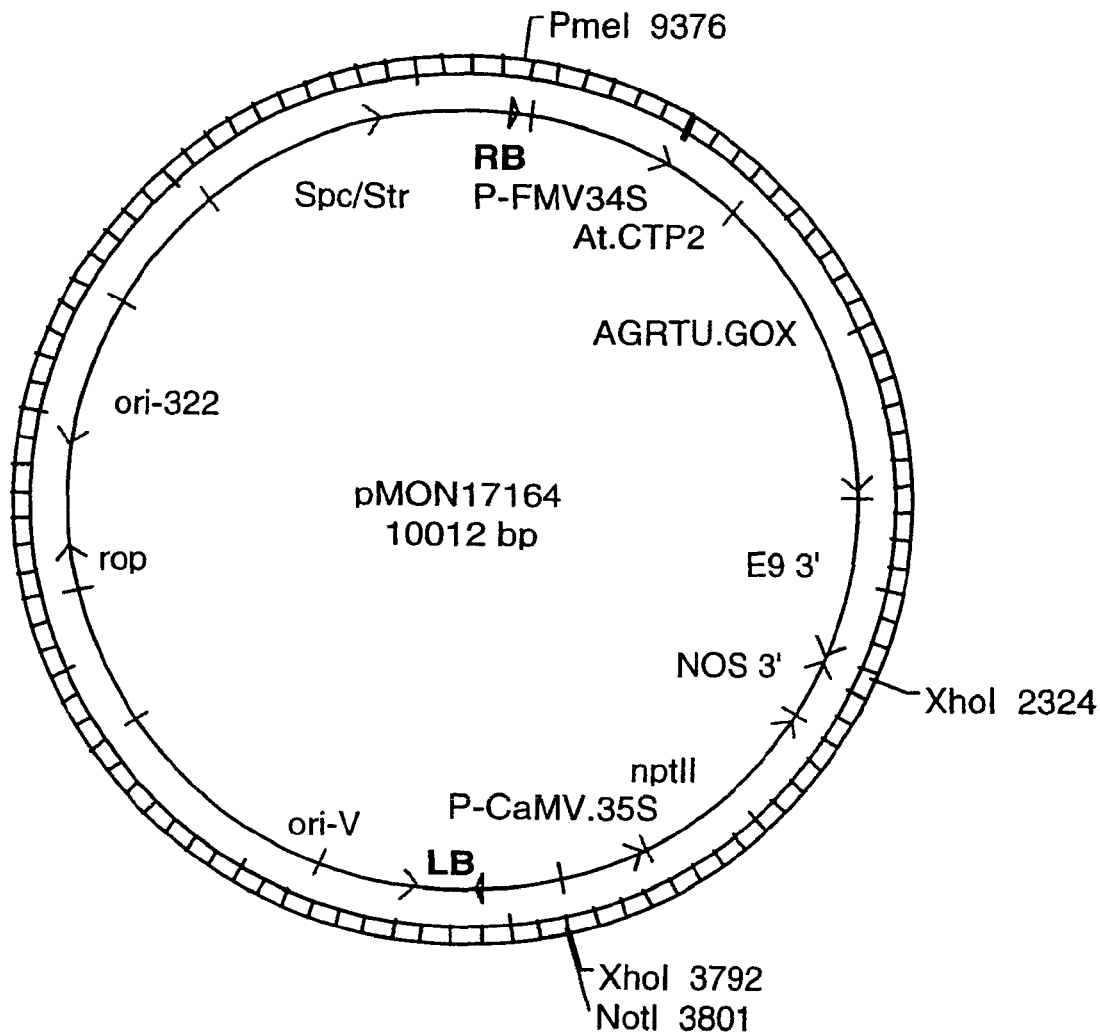

The conditional lethal gene, pehA, expression cassette is illustrated in pMON9443 construct (FIG. 12). Expression cassettes and regulatory elements found in the DNA segment outside of the plant expression elements contained in the T-DNA are common in many plasmid DNA backbones and function as plasmid maintenance elements, these include, but are not limited to, the aad (Spc/Str) gene for bacterial spectinomycin/streptomycin resistance, the pBR322 ori (ori322) that provides the origin of replication for maintenance in *E. coli*, the bom site for the conjugational transfer into the *Agrobacterium tumefaciens* cells, and a DNA segment is the 0.75 kb oriV containing the origin of replication from the RK2 plasmid.

Within the T-DNA borders are various plant expression cassettes. One of these contains the enhanced CaMV 35S promoter (P-CaMV.35S.en) (U.S. Pat. No. 5,359,142, herein incorporated in its entirety) in front of a poly-cloning site where the conditional lethal gene pehA:2 (U.S. Pat. No. 5,254,801) is encoded, followed by the pea ribulose-1,5-bisphosphate carboxylase small subunit E9 3' non-translated region (Coruzzi et al., EMBO J. 3:1671, 1984). A scorable marker gene, GUS:1 (U.S. Pat. No. 5,268,463, herein incorporated by reference in its entirety) expression is driven by the enhanced CaMV35S promoter and terminated by the 3'-non-translated region of the nopaline synthase gene (NOS 3'). A chimeric kanamycin resistance gene that permits selection of transformed plant cells, P-CaMV.35S/nptII/NOS 3' consists of the cauliflower mosaic virus (CaMV) 35S promoter (U.S. Pat. No. 5,858,742, herein incorporated in its entirety), the neomycin phosphotransferase type II (nptII) gene (U.S. Pat. No. 6,174,724, herein incorporated in its entirety) and the 3'-nontranslated region of the nopaline synthase gene (NOS 3'). The expression cassette containing the pehA:2 gene is mobilized from pMON9443 to comprise a functional location in anyone of the DNA constructs of the present invention and provide constitutive expression of the conditional lethal gene product there from.

Constitutive expression of the pehA:1 (SEQ ID NO:1) and pehA:2 (SEQ ID NO:2) phosphonate monoester hydrolase enzyme in plants has no direct effect on plant growth or development. Only in the present of a phosphonate ester of glyphosate protoxin does the enzyme function to convert the protoxin into a toxin in the tissue in which it is expressed. The pehA gene constitutive expression cassette, for example, the P-CaMV.35S:en/pehA:2/E9 3' of pMON9443 can be inserted into the two T-DNA constructs of the present invention at the unique endonuclease sites residing in the DNA segments outside of the two T-DNAs. The progeny of parents transformed with the DNA constructs of the present invention containing a constitutively expressed PEHA enzyme will be killed when treated with a phosphonate ester of glyphosate. The remaining progeny can be screened by bioassay, molecular diagnostics, field performance, trait efficacy or other methods particular to the agronomic genes of interest and known to those skilled in the art.

Tissue specific expression conditional lethal genes in combination with the DNA constructs of the present invention are particularly useful for eliminating unwanted cell or tissue types during breeding or propagation of the progeny. The DNA construct, pMON9430, illustrated in FIG. 13, contains a plant expression cassette where the pehA:1 gene expression is driven by a tissue specific promoter. In this example, the tissue specific promoter P-127a from tomato (U.S. Pat. No. 5,254,801) expresses in tapetal cells, a male tissue. Other promoters that have specific cell type expression patterns can be used to drive the expression of the pehA gene coding sequences. These promoters may be particularly selected to express in dicot or monocot plants, more preferably selected to express in the gametophytic cell of a transgenic dicot or monocot plant, or more preferably selected to express in the pollen cells of a transgenic dicot or monocot plant. A DNA molecule containing the pehA:1 expression cassette from pMON9430 can be mobilized by digestion with Not1 or HpaI/SmaI restriction endonucleases and inserted into the two T-DNA constructs of the present invention at the unique endonuclease restriction sites illustrated in the FIGS. 3-11. These insertions can occur in the DNA segments outside of the T-DNAs to select against plants containing these segments or the insertions can occur inside of the T-DNAs to select against plant cells or plants that contain a particular T-DNA.

The argE gene (N-acetyl-L-ornithine deacetylase) and its substrate N-acetyl-L-phosphinothricin (Kriete et al. Plant J. 9:809-818, 1996; Beriault et al. Plant Physiol. 121:619-628, 1999; herein incorporated by reference in its entirety) is another example of a protoxin substrate that can be converted into a toxic molecule in plants. An argE gene plant expression cassette can be inserted into the two T-DNA constructs of the present invention at sites in the DNA constructs located in the DNA segments between the two T-DNAs. Alternatively, the argE gene plant expression cassette can be inserted into one of the T-DNAs and used to select against the T-DNA at some future stage of plant development or in the process of plant breeding or plant cultivation. Tissue specific expression can direct the expression of the enzyme and hence the conversion of protoxin to certain cells or at a certain stage of development depending on the need. For example, the TA29 promoter driving expression of the argE coding sequence in tapetal cell was able to specifically able to convert the protoxin substrate into a toxin in these cells resulting in male sterility (Kriete et al. Plant J. 9:809-818, 1996, the entirety of which is herein incorporated by reference).

Glyphosate metabolism (degradation) has been examined in a wide variety of plants and little degradation has been reported in most of those studies. In those instances where degradation has been reported, the initial breakdown product is usually aminomethylphosphonate (AMPA) (Coupland, 1985. *The Herbicide Glyphosate* pp 25-34, Butterworths publ.; Marshall et al., 1987. Pestic. Sci 18:65-77). AMPA has been reported to be much less phytotoxic than glyphosate for most plant species (Franz, 1985. *The Herbicide Glyphosate* pp 25-34, Butterworths publ.) but not for all plant species (Tanaka et al., 1988. J. Fac. Agr. Kyushu Univ. 30:209-223). A number of pure cultures of bacteria have been identified that degrade glyphosate by one of the two known routes (Moore et al., 1983. Appl. Environ. Microbiol. 46:316-320; Talbot et al., 1984. Current Microbiol. 10:255-260; Shinabarger and Braymer, 1986. J. Bacteriol. 168:702-707; Balthazor and Hallas, 1986. Appl. Environ. Microbiol. 51:432-434; Kishore and Jacob, 1987. J. Biol. Chem. 262:12164-12168; Wackett et al., 1987. J. Bacteriol. 169:710-717; Pipke et al., 1987. Appl. Environ. Microbiol. 53:974-978; Pipke et al., 1987. Appl. Environ. Microbiol. 54:1293-1296; Hallas et al., 1988. J. Industrial Microbiol. 3:377-385; Jacob et al., 1988. Appl. Environ. Microbiol. 54:2953-2958; Liu et al., 1991. Appl. Environ. Microbiol. 57:1799-1804). Pure cultures capable of degrading glyphosate to AMPA have been reported for a *Flavobacterium* sp. (Balthazor and Hallas, 1986), for a *Pseudomonas* sp. (Jacob et al., 1988. Appl. Environ. Microbiol. 54:2953-2958) and for *Arthrobacter atrocyaneus* (Pipke and Amrhein, 1988). In addition, a large number of isolates that convert glyphosate to AMPA have been identified from industrial activated sludges that treat glyphosate wastes (Hallas et al., 1988).

Glyphosate oxidoreductase (GOX) (SEQ ID NO:3) degrades glyphosate to AMPA. This enzyme has been engineered into plants with DNA constructs, for example, pMON17164, illustrated in FIG. 14, as well as other constructs described in U.S. Pat. No. 5,463,175, the entirety of which is herein incorporated by reference, and confers glyphosate tolerance to these plants. AMPA being generally less phytotoxic than glyphosate is vegetatively tolerated by the transgenic plants. However, plant male gametophytic cells are particularly sensitive to AMPA. AMPA alone can function as a gametocide in plants. A transgenic plant that is expressing a glyphosate resistant EPSPS, for example, aroA:CP4, although highly tolerant to glyphosate still retains sensitivity to AMPA. The GOX gene expression directed by a pollen specific promoter converts glyphosate to AMPA in a glyphosate tolerant plant. The increased levels of AMPA would be toxic to the pollen cells expressing GOX and would be impaired or killed. In the present invention, a GOX plant expression cassette functions as a conditional lethal gene in a glyphosate tolerant plant. The GOX expression cassette can be inserted in the DNA segments between two T-DNAs and transgenic plants produced. When the plants are treated with glyphosate, the pollen cells containing the GOX expression cassette will be impaired or killed, leaving only the pollen that contains the segregated T-DNAs. In a similar method, when the GOX expression cassette is included within a T-DNA, then the pollen containing that T-DNA will be specifically impaired or killed. This application has utility for limiting the outcrossing of transgenes in a plant breeding environment and in a field environment by treatment with glyphosate.

Additional conditional lethal genes include, but are not limited to the iaaH gene encoding indoleacetamide hydrolase which can convert non-toxic levels of naphthalene acetamide into toxic levels of the auxin, naphthalene acetic acid (Klee et al., Genes Dev. 1:86-96, 1987, the entirety of which is herein incorporated by reference), the bacterial cytosine deaminase gene has been shown to function as a conditional lethal gene for negative selection in plants (Kobayashi et al. Jpn. J. Genet. 70:409-422; Perera et al. Plant Mol. Biol. 23:793-799, the entirety of which is herein incorporated by reference), and the viral thymidine kinase (Czako et al. Plant Physiol 104:1067-1071, 1994, the entirety of which is herein incorporated by reference).

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense. All references cited herein are hereby expressly incorporated herein by reference.

EXAMPLES

Example 1

The use of conditional lethal transgenes in two T-DNA constructs involves the construction of plant transformation vectors that include the appropriate combination of genetic elements necessary to direct adequate expression levels in target tissues. For monocotyledonous crop plants, a monocot vector that utilizes a plant expression cassette that contains a promoter (P) and first intron (I) for example, from the rice (Os) actin gene (P-Os.Act1/I-Os.Act1 (U.S. Pat. No. 5,641,876, herein incorporated by reference in its entirety). DNA molecules that encode targeting sequences may be used when determined by those skilled in the art that it would contribute to the desired phenotype, for example the plastid transit peptide sequence from the *Arabidopsis thaliana* (At) EPSP synthase gene (At.CTP2) (Klee et al. Mol. Gen. Genet. 210:437-442, the entirety of which is herein incorporated by reference) would be an appropriate choice. The choice of the conditional lethal transgene coding sequence is dependent on the method most useful for the operator. For example, constitutive expression of the coding sequences encoding phosphonate monoester hydrolase, carboxylate monester hydrolase, N-acetyl-L-ornithine deacetylase, and P450 monooxygenase CPY105A1 in transgenic plants will result in impairment or death of the plant after application of the respective protoxin. Modification of the nucleotide DNA sequence for each conditional lethal gene coding sequence for enhanced expression in monocots can be determined by those skilled in the art. A plant expression cassettes needs a polyadenylation/termination (T) region, such a region isolated from the *Agrobacterium tumefaciens* nopaline synthase gene (T-AGRTU.nos), would be an appropriate choice.

For specific dicotyledonous species, a plant expression vector that utilizes the promoter and 5' untranslated region (including intron I), for example, the plant elongation factor 1a gene (Elfα-A1) as described in U.S. Pat. No. 5,177,011, herein incorporated by reference in its entirety, constitutive plant viral promoters of the caulimovirus family, including by not limited to Cauliflower mosaic virus (P-CaMV.35S, U.S. Pat. No. 5,858,742, herein incorporated by reference in its entirety), and Figwort mosaic virus (P-FMV.34S, U.S. Pat. No. 5,378,619, herein incorporated by reference in its entirety). Transit peptide sequences can be used when necessary to enhance the desired phenotype, for example, the chloroplast transit peptide from the *Arabidopsis thaliana* EPSP synthase gene (At.CTP2). Termination regions for example, the polyadenylation/3' termination region from the *Pisum sativum* ribulose-1,5-bisphosphate carboxylase gene (E9 3') is a useful genetic element of a plant expression cassette.

Example 2

Figure 15:
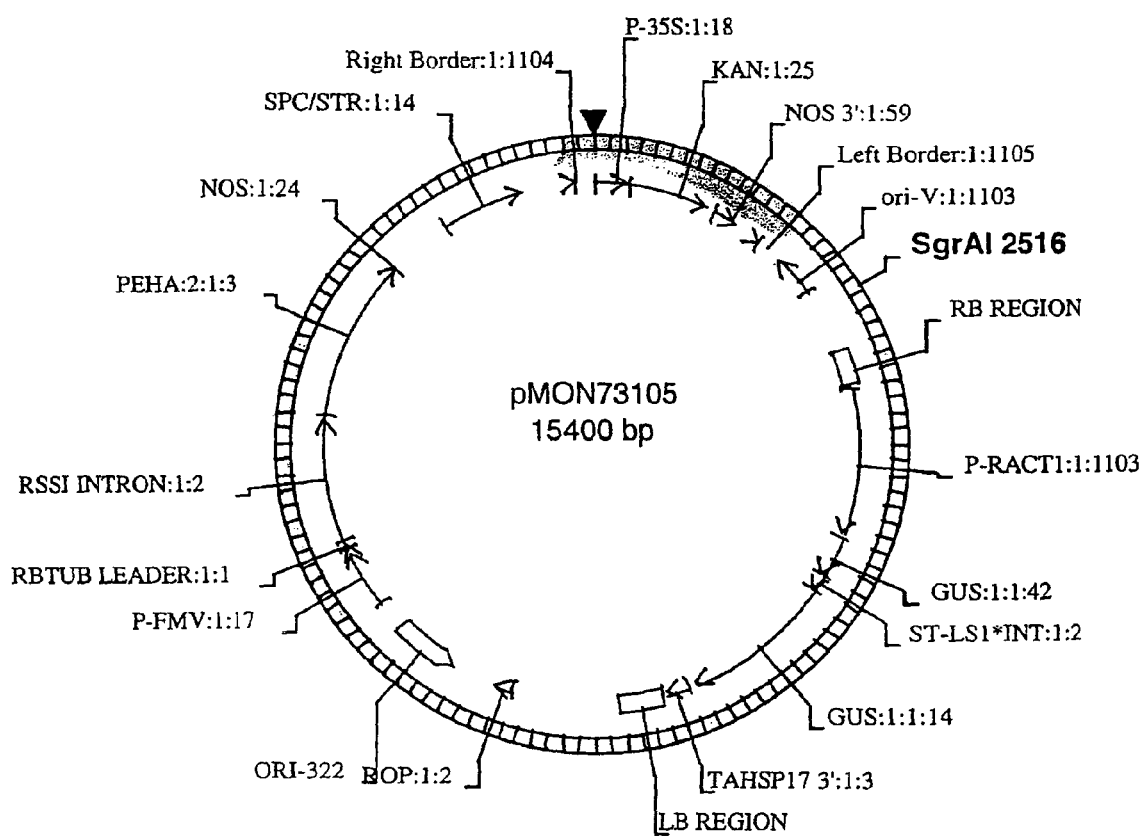
Figure 16:
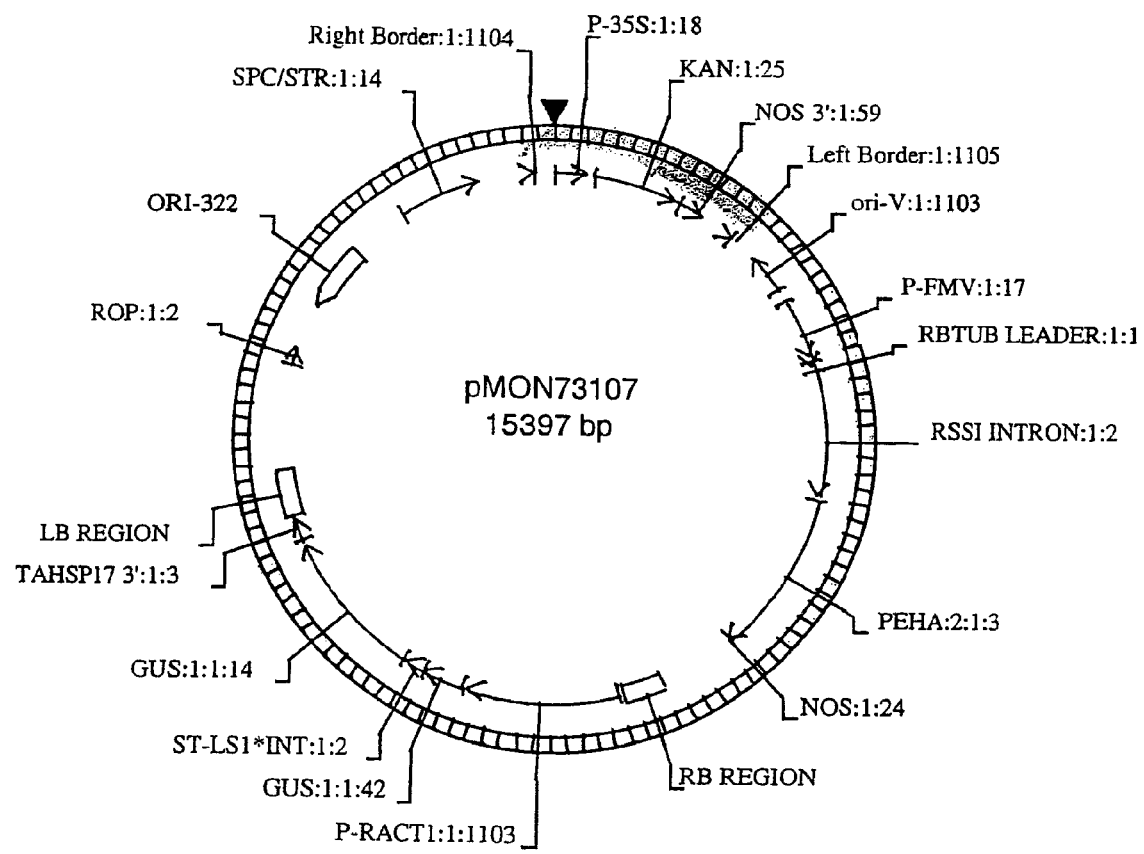
Figure 17:
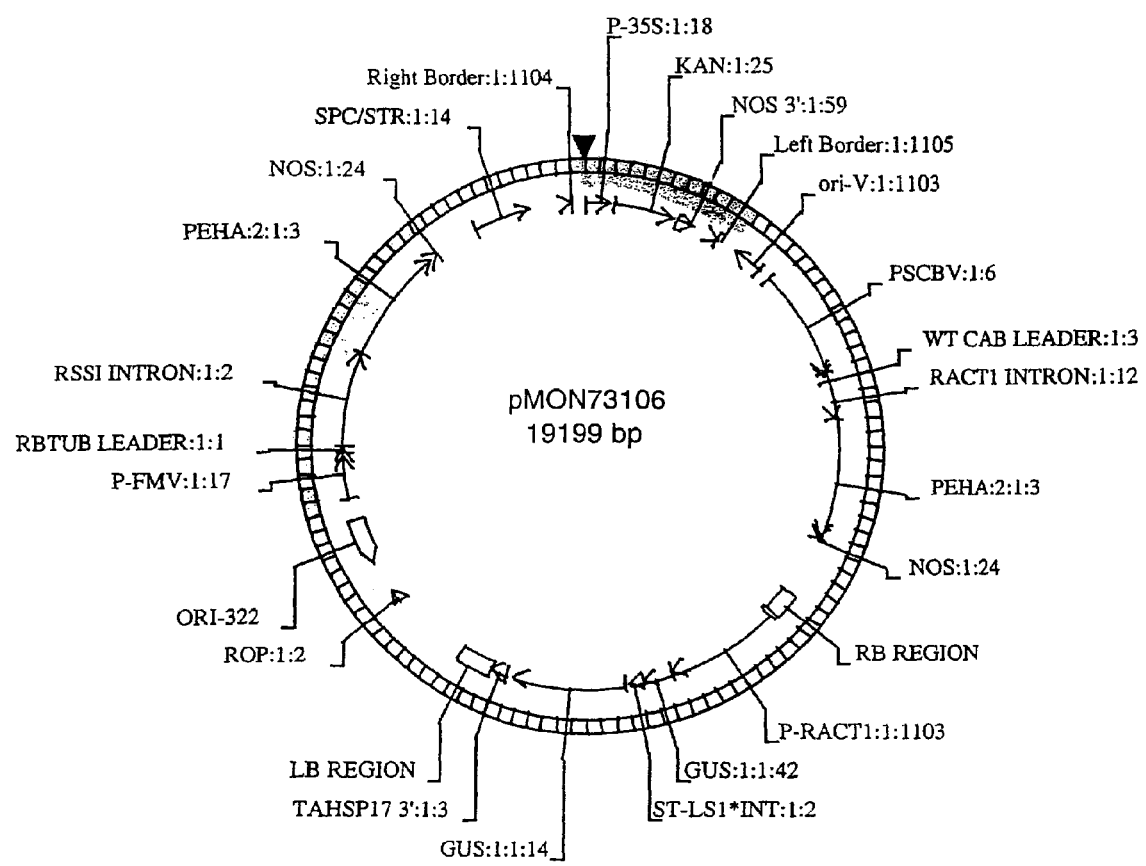
Figure 18:
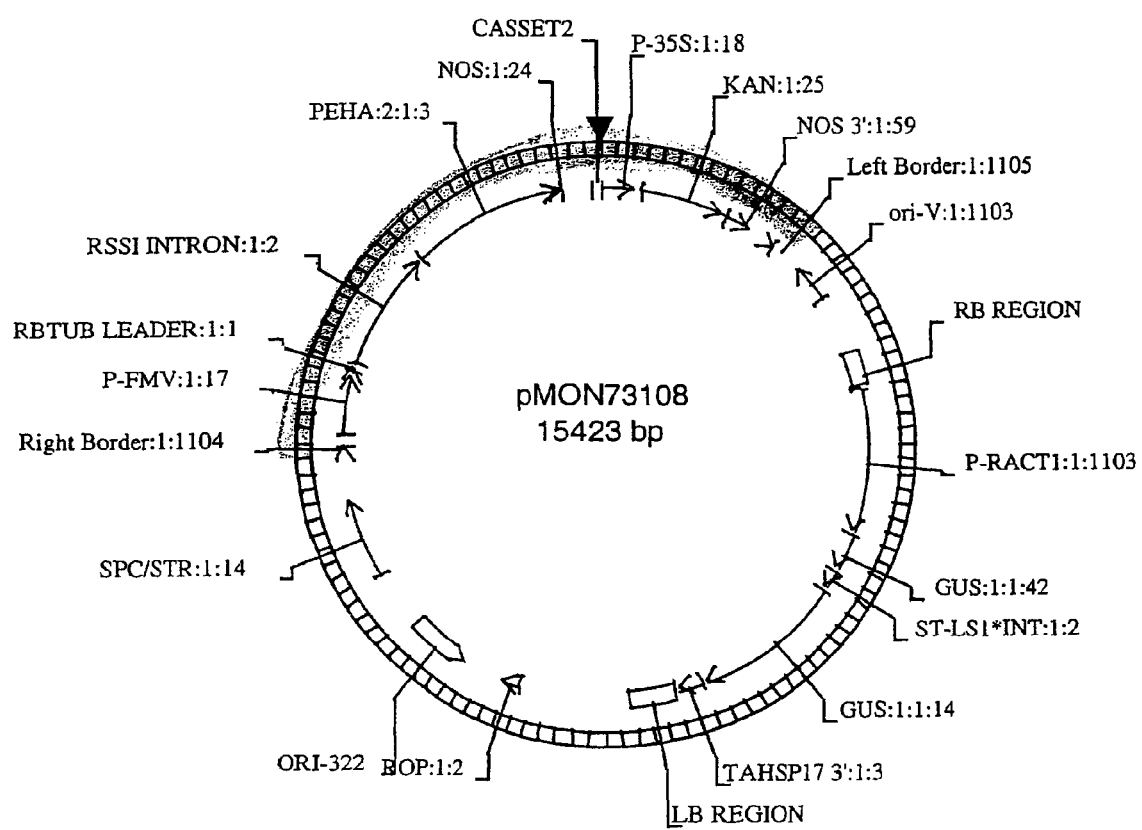

Transgenic corn plants can be produced by an *Agrobacterium* mediated transformation method. The constructs, pMON42070 (FIG. 9), pMON42071 (FIG. 10), pMON42072 (FIG. 11), a 1 T-DNA construct pMON42073 (FIG. 8) as a control construct, and constructs derived from these containing a conditional lethal gene inserted into the DNA segment located between the two T-DNAs are used to transform corn cells. For example, pMON73105 (FIG. 15, [RB]P-CaMV.35S/nptII/nos3'[LB]; [RB]P-Os.Act1/GUS:1/T-Ta.Hsp17[LB]; P-FMV/I-Os.RbcS/pehA2/nos3'; and pMON73107 (FIG. 16, [RB]P-CaMV.35S/nptII/nos3'[LB]; P-FMV/pehA2/nos3'; [RB] P-Os.Act1/GUS:1/E9 3'[LB]) construct of the present invention has an expression cassette for pehA2 inserted in one of the DNA segments of the construct. DNA constructs of the present invention have a conditional lethal gene inserted into both DNA segments, for example, pMON73106 (FIG. 17, [RB]P-CaMV.35S/nptII/nos3'[LB]; P-ScBV/I-Os.Act1/pehA2/nos3'; [RB]P-Os-.Act1/GUS; 1/T-Ta.Hsp 17-[LB]; P-FMV/I-Os.RbcS/pehA2/nos3'). These DNA constructs have a conditional lethal gene inserted into at least one T-DNA for use in eliminating this T-DNA at a desired stage in the breeding or propagation of the transgenic plant, for example pMON73108 (FIG. 18, [RB]P-FMV/I-Os.RbcS/pehA2/nos3'; P-CaMV.35S/nptII/nos3' [LB]; [RB]P-Os.Act1/GUS:1/T-Ta.Hsp17[LB].

The construct is transferred into *Agrobacterium* by a triparental mating method (Ditta et al., Proc. Natl. Acad. Sci. 77:7347-7351). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing 50 mg/l kanamycin, 50 mg/l streptomycin and spectinomycin and 25 mg/l chloramphenicol with 200 μM acetosyringone (AS). The *Agrobacterium* cells are resuspended in the inoculation medium (liquid CM4C) and the density is adjusted to $OD_{660}$ of 1. Freshly isolated Type II immature HiIIxLH198 and HiII corn embryos are inoculated with *Agrobacterium* containing the construct and co-cultured 2-3 days in the dark at 23° C. The embryos are then transferred to delay media (N6 1-100-12/micro/Carb 500/20 μM AgNO3) and incubated at 28° C. for 4 to 5 days. All subsequent cultures are kept at this temperature. Coleoptiles are removed one week after inoculation. For constructs that contain glyphosate tolerance genes, the corn embryos are transferred to the first selection medium (N61-0-12/Carb 500/0.5 mM glyphosate). Two weeks later, surviving tissue are transferred to the second selection medium (N61-0-12/Carb 500/1.0 mM glyphosate). Subculture surviving callus every 2 weeks until events can be identified. This will take 3 subcultures on 1.0 mM glyphosate. Once events are identified, bulk up the tissue to regenerate. For constructs that contain nptII tolerance genes, the corn embryos are transferred to the first selection medium (N61-0-12/Carb 500/50 mg/L paramomycin). Two weeks later, surviving tissue are transferred to the second selection medium (N61-0-12/Carb 500/100 mg/L paramomycin). Subculture surviving callus every 2 weeks until events can be identified. This will take 3 subcultures on 100-200 mg/L paramomycin. Once events are identified, bulk up the tissue to regenerate.

For regeneration, callus tissues are transferred to the regeneration medium (MSOD 0.1 µM ABA) and incubated for two weeks. The regenerating calli are transferred to a high sucrose medium and incubated for two weeks. The plantlets are transferred to MSOD media in culture vessel and kept for two weeks. Then the plants with roots are transferred into soil.

The corn plants are grown in a greenhouse to maturity, selfed and seeds collected. The seeds are planted in pots in conditions that permit germination and seedling growth. The plants are treated with an effective dose of the protoxin that corresponds to the conditional lethal gene. Leaf tissue samples are collected from the undamaged or surviving seedlings and assayed for the GUS activity by MOPS method (see for example, Jefferson et al., *EMBO J.* 6:3901, 1987, the entirety of which is herein incorporated by reference). The seedlings are also assayed for the presence of the EPSPS:CP4 enzyme by ELISA (Padgette et al. Crop Science 35:1451-1461, 1995). The segregation ratio is determined for the two T-DNAs. Plants with only the T-DNA containing the agronomic genes of interest are selfed, backcrossed or outcrossed in accordance with standard breeding methods (Fehr, *Principles of Cultivar Development* Vol. 1, pp. 2-3 (1987), the entirety of which is herein incorporated by reference.).

Transgenic wheat plants are produced by transforming immature embryos of wheat (*Triticum aestivum* L) cultivar Bobwhite with the constructs of the present invention. The constructs, pMON42070 (FIG. 9), pMON42071 (FIG. 10), pMON42072 (FIG. 11), a 1 T-DNA construct pMON42073 (FIG. 8) as a control construct, and constructs derived from these containing a conditional lethal gene inserted into the DNA segment located between the two T-DNAs are used to transform corn cells. A construct of the present invention is transferred into *Agrobacterium* by a triparental mating method (Ditta et al., Proc. Natl. Acad. Sci. 77:7347-7351). Wheat embryos are isolated from the immature caryopsis 13-15 days after pollination, and cultured on CM4C (Table 1.) for 3-4 days. The embryos showing active cell division, but no apparent callus formation are selected for *Agrobacterium* infection.

TABLE 1

Supplemental Components in Basal Media[1]

| Components | CM4 | CM4C | MMS.2C | MMS0 |
|---|---|---|---|---|
| 2,4-D (mg/l) | 0.5 | 0.5 | 0.2 | — |
| Pichloram (mg/l)[2] | | 2.2 | 2.2 | |
| Maltose (g/l) | 40.0 | 40.0 | 40.0 | 40.0 |
| Glutamine (g/l) | | 0.5 | 0.5 | |
| Magnesium Chloride (g/l) | | 0.75 | 0.7 | |
| Casein Hydrolysate (g/l) | | 0.1 | 0.1 | |
| MES (g/l) | | 1.95 | 1.95 | 1.95 |
| Ascorbic Acid (mg/l)[2] | | 100.0 | 100.0 | 100.0 |
| Gelling Agent (g/l)[3] | 2(P) | 2(P) | 2(G) | 2(G) |

[1]All media contain basal salts (MS basal salts) and vitamins (MS vitamins) from Murashige and Skoog (1962). The pH in each medium is adjusted to 5.8.
[2]Filter-sterilized and added to the medium after autoclaving.
[3]Phytagel ™ (P) or Gelrite ®(G).

Liquid cultures of *Agrobacterium* containing the constructs of the present invention are initiated from glycerol stocks or from a freshly streaked plate and grown overnight at 26° C.-28° C. with shaking (approximately 150 rpm) to mid-log phase ($OD_{660}$=1-1.5) in liquid LB medium, pH 7.0 containing 50 mg/l kanamycin, 50 mg/l streptomycin and spectinomycin and 25 mg/l chloramphenicol with 200 µM acetosyringone (AS). The *Agrobacterium* cells are resuspended in the inoculation medium (liquid CM4C) and the density is adjusted to $OD_{660}$ of 1. The immature embryos cultured in CM4C medium are transferred into sterile petri plates (16×20 mm) or wells of a 6-well cell culture plate (Costar Corporation, Cambridge, Mass.) containing 10 ml of inoculation medium per petri plate or 5 ml per cell culture cluster plate. An equal amount of the *Agrobacterium* cell suspension is added such that the final concentration of *Agrobacterium* cells is an $OD_{600}$ of 0.5. In most experiments, pluronic F68 is added to the inoculation mixture at a final concentration of 0.01%. The ratio between the *Agrobacterium* and immature embryos is about 10 ml: 20-200 IEs. The inoculation is allowed to proceed at 23° C.-26° C. from 5-60 minutes. After the inoculation period, the remaining *Agrobacterium* cells are removed from the explants by using vacuum aspiration equipment. A piece of sterile Whatman No. 1 filter paper (to fit the size of the petri plate) is placed in each of 60×15 or 60×20 mm petri dishes. Two hundred µl of sterile water is placed in the middle of the filter paper. After 2-3 minutes, the inoculated immature embryos are placed in the plates. Usually, 20-50 explants are grouped as one stack (about 1 cm in size and 60-80 mg/stack), with 4-5 stacks on each plate. The plates are immediately covered with Parafilm® and then co-cultivated in the dark at 24° C.-26° C. for 2-3 days. The co-cultivated PCIEs are transferred CM4C+500 mg/l carbenicillin medium (delay medium) at dark. After 7 days on the delay medium, the immature embryos are transferred to CM4C supplemented with 2 mM glyphosate and 500 mg/l carbenicillin for selection for one week. Then calli are transferred to MMS0.2C+0.1 mM glyphosate+250 mg/l carbenicillin medium for 2 weeks under light for further selection. Embryogenic calli are transferred to a second regeneration medium MMS0C with lower glyphosate concentration (0.02 mM) and 500 mg/L carbenicillin for plant regeneration. Those embryogenic calli are transferred onto fresh medium every two weeks. Regenerated plantlets are transferred to Sundae cups (Sweetheart Cup Company, Chicago, Ill.) containing the second regeneration medium for further growth and selection. When roots are well established from transgenic plants the plants are transferred to soil for further evaluation.

The wheat plants are grown in a greenhouse to maturity, selfed and seeds collected. The seeds are planted in pots in conditions that permit germination and seedling growth. The plants are treated with an effective dose of the protoxin that corresponds to the conditional lethal gene. Leaf tissue samples are collected from the undamaged or surviving seedlings and assayed for the reporter gene, for example, GUS by assays performed by routine methods (see for example, Jefferson et al., EMBO J. 6:3901, 1987). The seedlings are also assayed for the presence of the CP4 EPSPS enzyme or NPTII by ELISA depending on the construct used. The segregation ratio is determined for the two T-DNAs. Plants with only the T-DNA containing the agronomic genes of interest are selfed, backcrossed or outcrossed in accordance with standard breeding methods.

Transgenic *Arabidopsis* plants are produced with the DNA constructs of the present invention using the method of vacuum infiltration of *Agrobacterium* containing the DNA constructs (Bechtold et al., C R Acad Paris Life Sci 316: 1194-1199, the entirety of which is herein incorporated by reference). The constructs, a 1 T-DNA construct pMON42061 (FIG. 1) as a control construct, pMON51652

(FIG. 2), pMON51653 (FIG. 3), pMON54237 (FIG. 4), pMON51658 (FIG. 5), pMON51661 (FIG. 6), pMON51676 (FIG. 7) and constructs derived from these containing a conditional lethal gene inserted into the DNA segment located between the two T-DNAs are used to transform *Arabidopsis* cells. Seeds are potted in soil in trays in a growth chamber adjusted for 24° C., 16 hour light (120 µE m$^{-2}$ s$^{-1}$) cycle to permit normal growth and development of the seedling plants. The *Arabidopsis* seedling plants are treated with an effective dose of the protoxin that corresponds to the conditional lethal gene capability to convert the protoxin into a toxin. Leaf tissue samples are collected from the undamaged or surviving seedlings and assayed for the GUS activity. The seedlings are also assayed for the presence of the CP4 EPSPS enzyme or NPTII by ELISA depending on the construct used. The segregation ratio is determined for the two T-DNAs. Plants with only the T-DNA containing the agronomic genes of interest are selfed, backcrossed or outcrossed in accordance with standard breeding methods (Fehr, *Principles of Cultivar Development* Vol. 1, pp. 2-3 (1987), the entirety of which is herein incorporated by reference).

Transgenic soybean (*Glycine max*) containing DNA constructs of the present invention expressing a glyphosate tolerance gene are generated by *Agrobacterium tumefaciens*-mediated transformation of cotyledon explants. Asgrow (Stuttgart, Ak.) soybean cultivars A3244, A4922, and A5547 soybean seeds are soaked in sterile distilled water (SDW) at room temperature for either two hours or three minutes, drained, and left moist for two hours. Bean Germination Media (BGM, Table 2) is added after two hours to 2-3 times the depth of the seed volume and incubated at room temperature in the dark for nine to eleven hours.

At eleven to thirteen hours from initiation of germination, the seed axes are removed from seeds and held in sterile distilled water. Explants are rinsed two to three times with sterile distilled water, drained and divided into sets of 50-300. Each set is placed into a vessel along with either ABI or LBA4404 strains of *Agrobacteria* containing the DNA construct, induced with 0.2 mM Acetosryingone, 1.0 µM galacturonic acid and 0.25 mg/L GA$_3$ Examples of vessels included a 25 milliliters (ml) glass test tube with two ml of *Agrobacterium*, a 125 ml glass flask with 5-10 ml *Agrobacterium*, or a Plantcon™ with 20-50 ml *Agrobacterium*.

Each vessel is held in a sonicator (L&R Ultrasonics Model PC5 or QS140) with 500-2000 milliliters of sterile distilled water plus 0.1% Triton X100 and sonicated for five to sixty seconds. In some cases, fresh inoculum is added following sonication. Explants are inoculated for about one hour while shaking on an orbital shaker at approximately 90 RPM.

Explants are then co-cultured on one piece of Whatman grade 1 filter paper with one to seven mil of 1/10× Gamborg's B5 media (Gamborg et al., Exp. Cell Res., 50:151-158, 1968) containing 1.68 mg/L BAP, 3.9 g/L MES with inducers as listed above for two to four days at approximately 23° C., dark.

After co-culture, explants are transferred to Woody Plant Media (WPM) (McCown et al., Proc. International Plant Propagation Soc., 30:421, 1981) containing 2% sucrose, 60 mg/L Benomyl, 75 µM glyphosate plus combinations of the following antibiotics; 200 mg/L Carbenecillin, 100-200 mg/L Cefotaxime, 100 mg/L Timetin. Cultures are incubated at approximately 28° C. with a 16 hour light, 8 hour dark photoperiod. A transfer to fresh media is made after seven to fourteen days. In some cases, a third transfer is made after an additional ten to fourteen days.

Shoots are harvested between three and seven weeks post-inoculation. Shoots rooted on BRM (Table 2) with 25 to 40 µM glyphosate.

TABLE 2

| BEAN GERMINATION MEDIA (BGM 2.5%) | |
|---|---|
| COMPOUND: | QUANTITY PER LITER |
| BT STOCK #1 | 10 ml |
| BT STOCK #2 | 10 ml |
| BT STOCK #3 | 3 ml |
| BT STOCK #4 | 3 ml |
| BT STOCK #5 | 1 ml |
| SUCROSE | 25 g |

Adjust to pH 5.8.
Dispense into sterile 1 L media bottles

| ADDITIONS PRIOR TO USE: | PER 1 L |
|---|---|
| CEFOTAXIME (50 mg/ml) | 2.5 ml |
| FUNGICIDE STOCK | 3 ml |

Bt Stock for Bean Germination Medium

Make and store each stock individually. Dissolve each chemical thoroughly in the order listed before adding the next. Adjust volume of each stock accordingly. Store at 4° C.

| Bt Stock 1 (1 liter) | |
|---|---|
| KNO$_3$ | 50.5 g |
| NH$_4$NO$_3$ | 24.0 g |
| MgSO$_4$*7H$_2$O | 49.3 g |
| KH$_2$PO$_4$ | 2.7 g |
| Bt Stock 2 (1 liter) | |
| CaCl$_2$*2H$_2$O | 17.6 g |
| Bt Stock 3 (1 liter) | |
| H$_3$BO$_3$ | 0.62 g |
| MnSO$_4$—H$_2$O | 1.69 g |
| ZnSO$_4$—7H$_2$O | 0.86 g |
| KI | 0.083 g |
| NaMoO$_4$—2H$_2$O | 0.072 g |
| CuSO$_4$—5H$_2$O | 0.25 ml of 1.0 mg/ml stock |
| CoCl$_4$—6H$_2$O | 0.25 ml of 1.0 mg/ml stock |
| Bt Stock 4 (1 liter) | |
| Na$_2$EDTA | 1.116 g |
| FeSO$_4$7H$_2$O | 0.834 g |
| Bt Stock 5 (500 ml) Store in a foil wrapped container | |
| Thiamine-HCl | 0.67 g |
| Nicotinic Acid | 0.25 g |
| Pyridoxine-HCl | 0.41 g |
| FUNGICIDE STOCK (100 ml) | |
| chlorothalonile (75% WP) | 1.0 g |
| benomyl (50% WP) | 1.0 g |
| captan (50% WP) | 1.0 g |
| Add to 100 ml of sterile distilled water. | |
| Shake well before using. | |
| BEAN ROOTING MEDIA (BRM) (for 4 L) | |
| MS Salts | 8.6 g |
| Myo-Inositol (Cell Culture Grade) | 0.40 g |
| Soybean Rooting Media Vitamin Stock | 8 ml |

-continued

| | |
|---|---|
| L-Cysteine (10 mg/mL) | 40 m |
| Sucrose (Ultra Pure) | 120 g |
| | pH 5.8 |
| Washed Agar | 32 g |
| ADDITIONS AFTER AUTOCLAVING: | |
| BRM Hormone Stock | 20.0 ml |
| BRM HORMONE STOCK (1 liter) | |
| 6.0 ml IAA (0.033 mg/ml) | |
| 4.0 ml SDW | |
| VITAMIN STOCK FOR SOYBEAN ROOTING MEDIA (1 liter) | |
| Glycine | 1.0 g |
| Nicotinic Acid | 0.25 g |
| Pyridoxine HCl | 0.25 g |
| Thiamine HCl | 0.05 g |

Dissolve one ingredient at a time, bring to volume.

The soybean plants are grown in a greenhouse to maturity, selfed and seeds collected. The seeds are planted in pots in conditions that permit germination and seedling growth. The plants are treated with an effective dose of the protoxin that corresponds to the conditional lethal gene. Leaf tissue samples are collected from the undamaged or surviving seedlings and assayed for the reporter gene, for example, the GUS activity by MOPS method (see for example, Jefferson et al., $EMBO\ J.$ 6:3901, 1987). The seedlings are also assayed for the presence of the CP 4 EPSPS enzyme by ELISA (Padgette et al. Crop Science 35:1451-1461, 1995) or NPTII by ELISA depending on the construct used. The segregation ratio is determined for the two T-DNAs. Plants with only the T-DNA containing the agronomic genes of interest are selfed, backcrossed or outcrossed in accordance with standard breeding methods (Fehr, $Principles\ of\ Cultivar\ Development$ Vol. 1, pp. 2-3 (1987).

DNA constructs containing two T-DNA molecules and at least one conditional lethal gene and methods thereof are useful to enhance the identification of transgenic plants for which the T-DNAs have integrated into separate physical loci, and that can be genetically segregated in gametes and progeny. In addition, two DNA constructs each with at least one T-DNA molecule and at least one of the DNA constructs having a conditional lethal gene, when present in different $Agrobacterium$ strains and transformed into plants by mixing the different strains, provides enhancement over co-transformation methods using strains of the same type. Furthermore, the methods described in this example illustrate an aspect of the invention where when used in combination with the DNA constructs of the invention are useful for the elimination of plants containing T-DNAs comprising marker transgenes, or the selective elimination of plants containing T-DNAs with agronomic transgenes or the selective elimination of germ cells containing T-DNAs with marker transgenes or agronomic transgenes. The method and DNA constructs enhance the frequency of detecting expression of the gene of interest, enhance the selection of independent segregation events and decrease the presence of extraneous construct DNA segments in the plant genome.

Example 3

Strong constitutive promoters may influence the expression of linked transgenes that contain tissue or organ specific promoters, this results in an aberrant expression pattern from the tissue or organ specific promoters referred to as leaky expression. The leaky expression of a transgene product in non-targeted tissues is an important issue for transgenic plants, especially if the expression in the non-target tissues causes undesirable phenotypes. Additionally, often the true expression pattern and promoter strength of a tissue specific promoter cannot be precisely determined because of the influence of a linked expression cassette containing a constitutive promoter. The present invention provides a method where DNA constructs that allow for the separate integration of T-DNAs are used to reveal the true expression pattern of tissue specific promoters. The method provides plants with tissue specific expression cassettes free from an expression cassette containing a selectable marker gene.

Seed tissue is an especially useful tissue for targeting a transgene product. Pharmaceutical peptides, enzymes that enhance oil production or provide for modified oils, enzymes that enhance vitamin production, enzymes that enhance essential amino acid content, enzymes that enhance starch accumulation, proteins that provide more balanced amino acid content of the seed, enzymes that provide biopolymer production, proteins that are antimicrobial, antifungal, and insecticidal, also modified carbohydrate content, such as, low phytate, low stachyose, and enhanced fermentable sugars are some examples of products where seed specific tissue expression may be more desirable relative to constitutive plant expression. Seed specific promoters, for example, the 7Sα' and napin promoters, from soybean and $Brassica$, respectively, can show activity in vegetative tissues when the expression cassettes containing these promoters and a gene of interest are linked to expression cassettes containing constitutive promoters used to express selectable marker genes. Promoters having constitutive activity are often isolated from plant DNA viruses, e.g. caulimoviruses, such as a Figwort Mosaic Virus (FMV) promoter or a cauliflower mosaic virus (CaMV) promoter are most often used to direct expression of an antibiotic resistance gene product or herbicide resistance gene product. The NPTII antibiotic enzyme (tolerance to kanamycin) and the EPSPS:CP4 enzyme (tolerance to glyphosate) are selectable marker gene products often used as for transgenic plant production.

Figure 19:
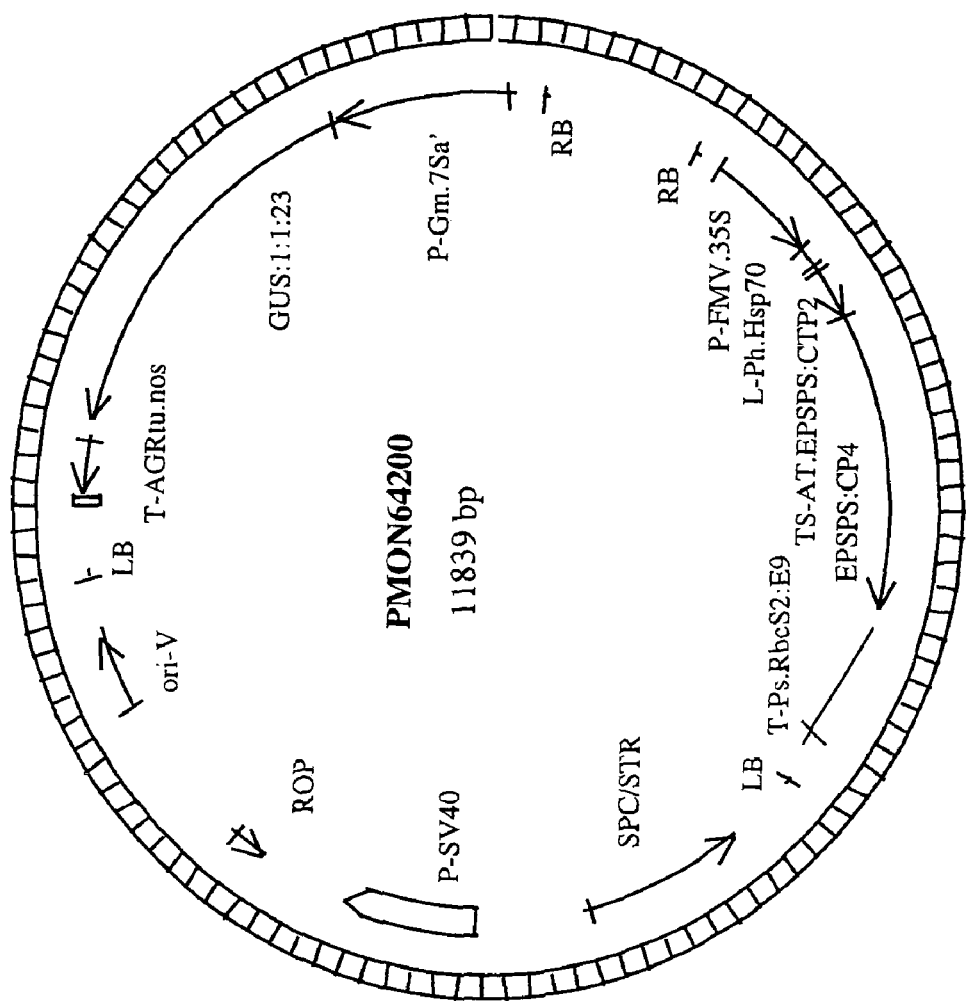

The DNA construct, pMON64200 (FIG. 19) is a 2 T-DNA vector that contains P-Gm.7Sα'/GUS/T-nos and P-FMV.35S/EPSPS:CP4/T-Ps.E9 expression cassette in separate T-DNAs that is transformed into soybean cells and fertile plants regenerated. The T-DNAs are integrated into the soybean genome either at different loci (unlinked) or at the same locus (linked). In this example, the gene of interest expresses β-glucuronidase (GUS) in seed tissue (cotyledon), however, the gene of interest could be any gene for which the expression product is desired to be expressed in a certain tissue or organ. The physical linkage between these two cassettes in R0 and R1 plants is determined by using Southern blot and PCR analysis. Phenotypic segregation of the GUS activity and the glyphosate tolerance is also documented to confirm the physical linkage analysis. GUS activity can be detected using a chromogenic substrate or the MOPS assay method and EPSPS:CP4 activity can be detected by spraying the plants with glyphosate or using an immunological method to assay for the presence of the EPSPS:CP4 protein. Because the R1 population is usually segregating, the GUS activity is examined in the cotyledons of the germinating seeds to select plants that are positive for the P-Gm.7Sα'/GUS/F-nos cassette. Because the P-Gm.7Sα' promoter is expected to be seed specific, positive GUS activity in vegetative tissue, such as leaves, is used as the indicator of leaky expression.

Figure 25:
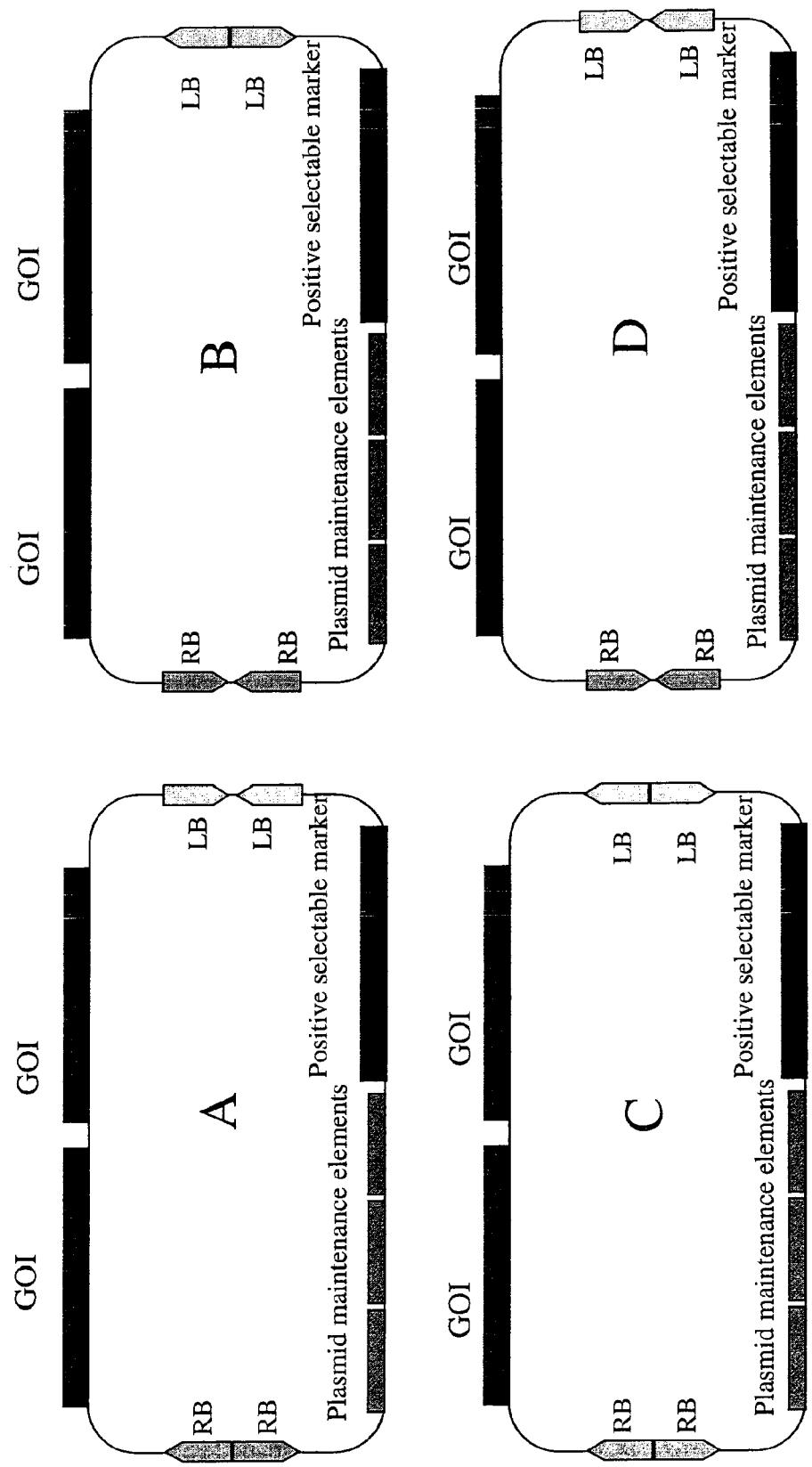
Figure 26:
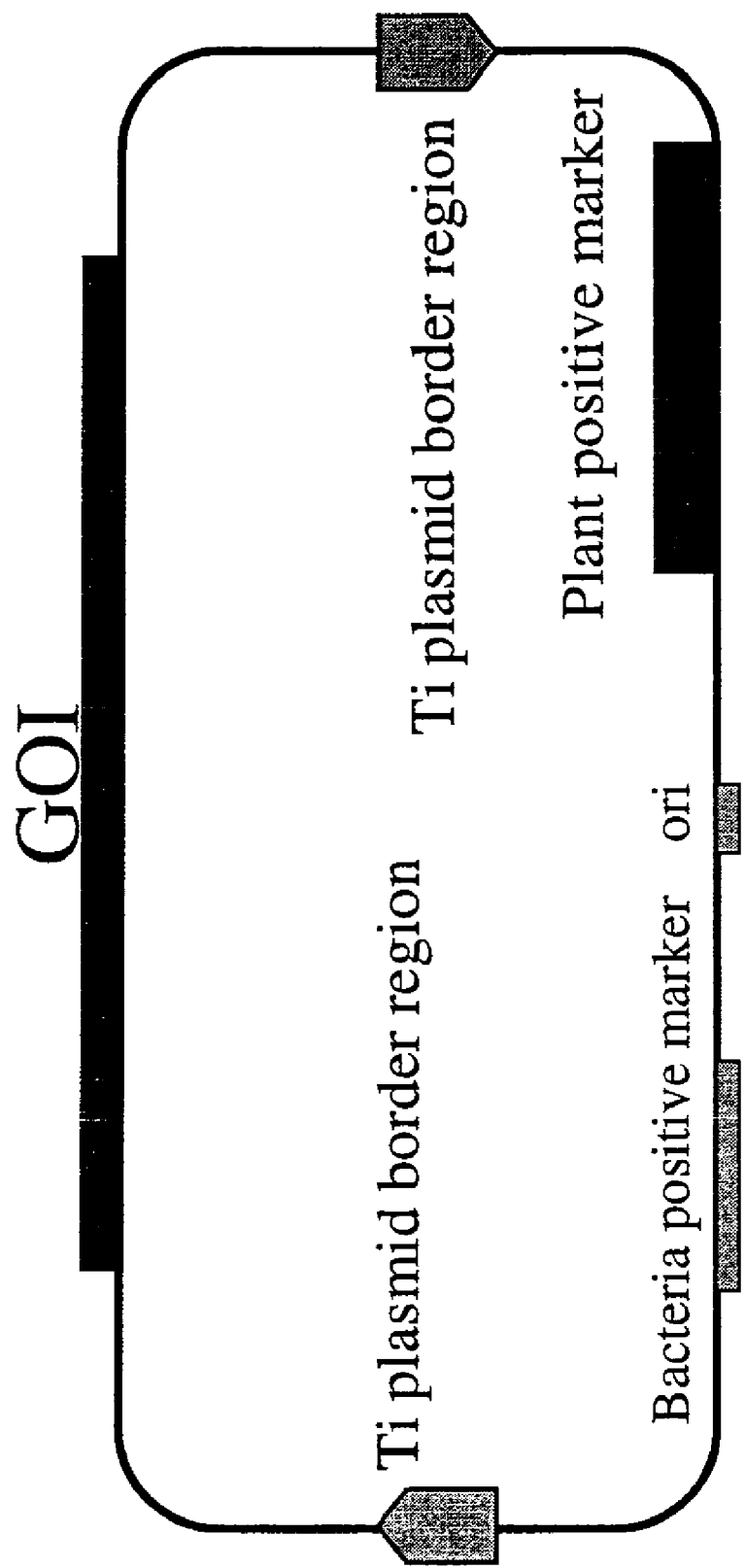

Table 3 shows the analysis of transgenic events in which a two T-DNA construct is used to determine promoter expression patterns. A positive (+) for GUS staining in leaf indicates the plant has leaky expression, a positive (+) for GUS staining in cotyledon (speed specific expression) indicates the plant has a functional copy of P-Gm.7Sα'/GUS cassette, and a positive (+) glyphosate tolerance indicates that the plant has a functional copy of the selectable marker cassette (P-FMV/EPSPS:CP4). The events are analyzed by Southern blot, phenotype, and PCR to determine the linkage of the two expression cassettes. Three events have multiple insertion loci that are identified as "locus 1 or locus 2" in the segregating progeny. Ten events are shown to have linked expression cassettes, 3 events are unlinked and 3 events are marker free. Table 3 shows that all of the marker free or unlinked events do not show leaf GUS expression, indicating that linkage with the selectable marker expression cassette adversely affects the seed specific expression pattern of the gene of interest. In contrast, 8 out of 10 linked events results in a leaky expression pattern.

marker gene and the plasmid maintenance elements. The Ti plasmid border regions are arranged in like pairs with various configurations as illustrated in FIG. 25. The arrangement of border regions, GOI, plant positive selectable marker gene, and plasmid maintenance elements in these DNA constructs will provide for efficient independent integration of the T-DNA molecules.

Example 5

DNA constructs are created that contain two Ti plasmid border regions (RB, LB or combinations thereof) in which a gene of interest is contained in a first DNA region between the two border regions that does not contain any plasmid maintenance elements, and in a second DNA region between the two border regions contains a positive selectable marker gene and plasmid maintenance elements. The second DNA region

TABLE 3

A summary of a 2T-DNA study on FMV/7Sα' promoter interaction

| pMON64200 event # | Leaf GUS (Leakiness) | Cotyledon GUS | glyphosate tolerance | Linkage Southern | CP4/GUS phenotype | Linkage PCR |
|---|---|---|---|---|---|---|
| 20095-locus1 | + | + | + | NA | linked | linked |
| 19931 | + | + | + | linked | linked | linked |
| 19937 | + | + | + | linked | linked | linked |
| 20139 | + | + | + | NA | linked | linked |
| 19927 | + | + | + | linked | linked | NA |
| 19989 | + | + | + | NA | linked | linked |
| 20038 | + | + | + | linked | linked | linked |
| 20043 | + | + | + | linked | linked | NA |
| 20286-locus1 | − | + | + | linked | linked | linked |
| 20116 | − | + | + | linked | linked | NA |
| 20282 | − | + | + | unlinked | segregating | |
| 20277 | − | + | + | unlinked | segregating | |
| 20127-locus2 | − | + | − | unlinked | segregating | |
| 20095-locus2 | − | + | − | marker free | | |
| 20286-locus2 | − | + | − | marker free | | |
| 20127-locus1 | − | + | − | marker free | | |

NA—not available

For linkage PCR analysis, two primers of GUS coding region and two primers of EPSPS:CP4 coding region are designed to accommodate all possible orientations. PCR reactions with four possible primer combination sets are performed for each linked event, and the likely orientation is based on the primer set(s) that gave PCR products.

All of the unlinked and marker free plants show GUS expression only in the cotyledon tissue indicating that linkage to the expression cassette containing the viral promoter negatively affects the tissue specific activity of the Gm.7Sα' promoter. Other tissue specific promoters known in the art of plant molecular biology can be evaluated as described and used in the constructs and methods described herein to segregate the transgene expression cassettes to provide enhanced function of the tissue specific promoter expression cassette.

Example 4

Figure 24:
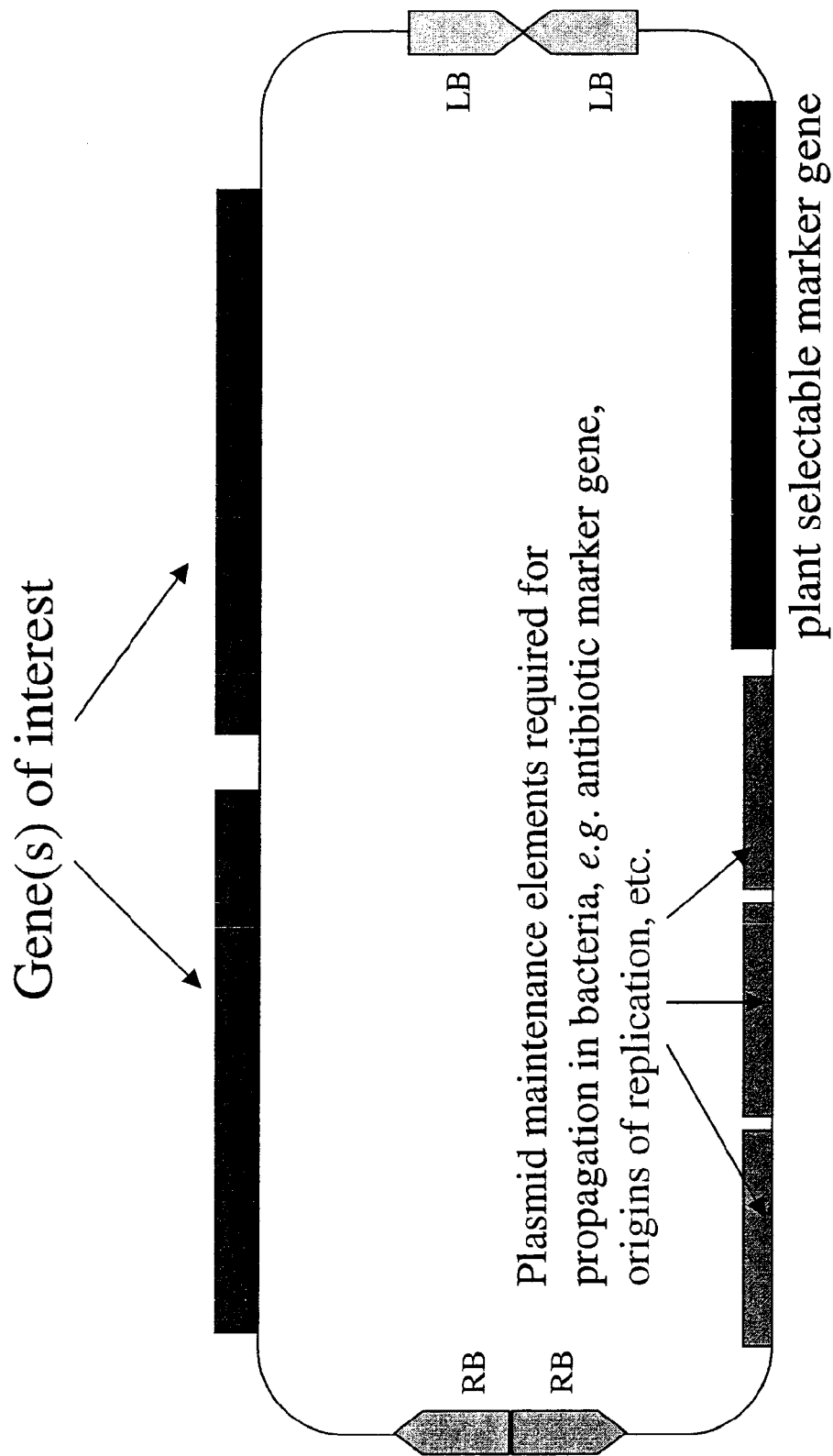

DNA constructs are created that contain four Ti plasmid border regions that comprise two T-DNA molecules, there is no substantial DNA segment between the T-DNA molecules. The basic design of this plasmid is shown in FIG. 24. One of the T-DNA molecules contains the gene(s) of interest (GOI) and the second T-DNA molecule contains the plant selectable containing the plasmid maintenance elements is often referred to as the vector backbone. It has become undesirable to have vector backbone sequences in transgenic plants. However, in the constructs of this aspect of the present invention the vector backbone becomes a DNA region that is integrated into the genome of a plant, this DNA region contains the positive selectable marker gene and is intentional selected for in the transgenic plants.

Figure 20:
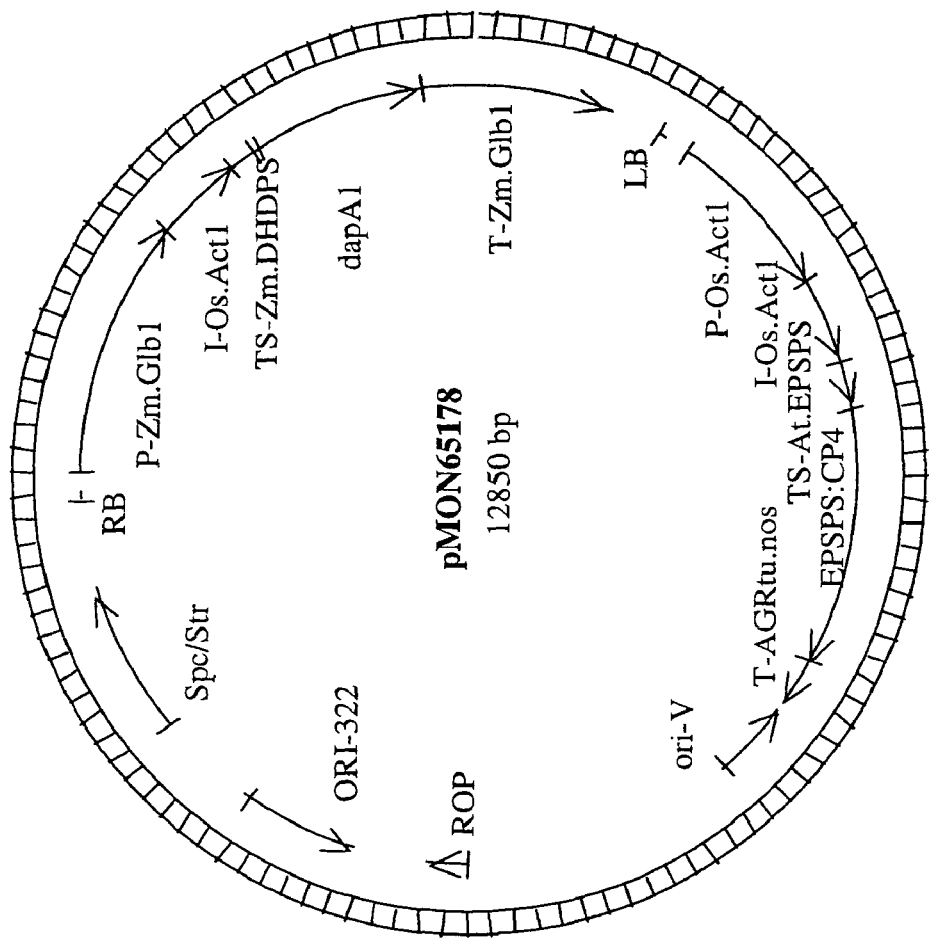
Figure 21:
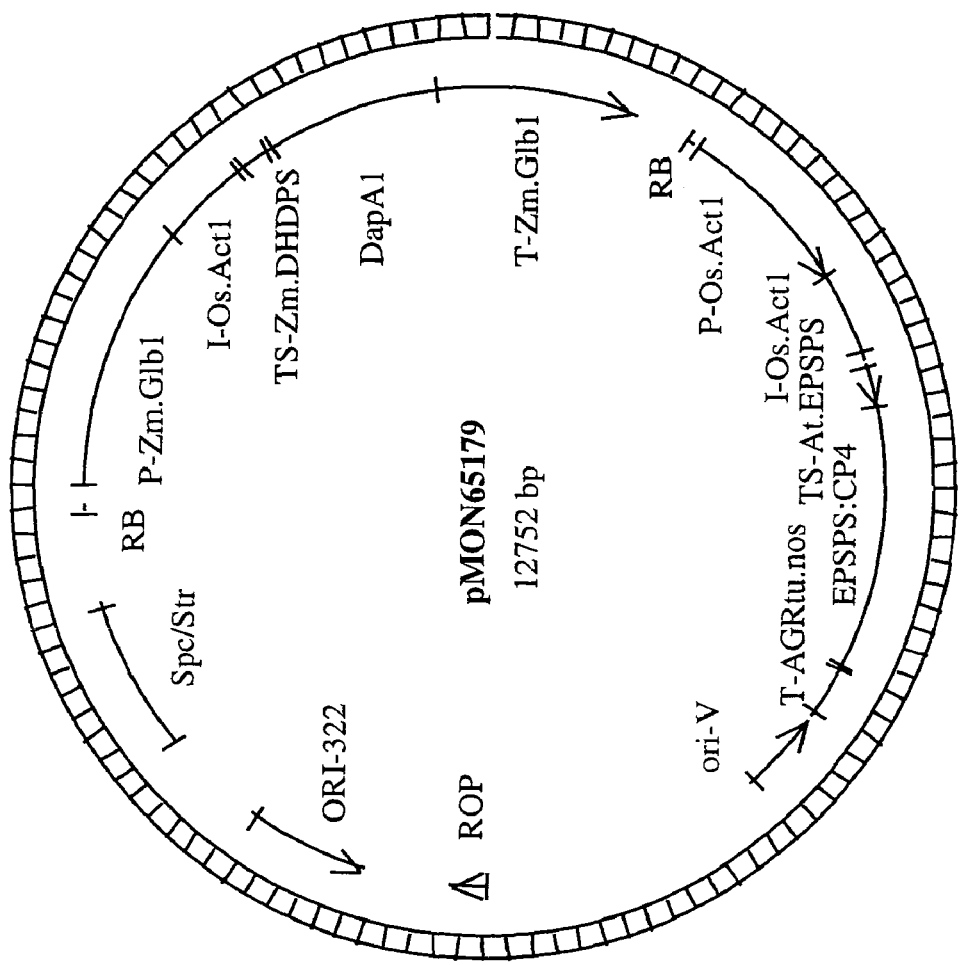
Figure 22:
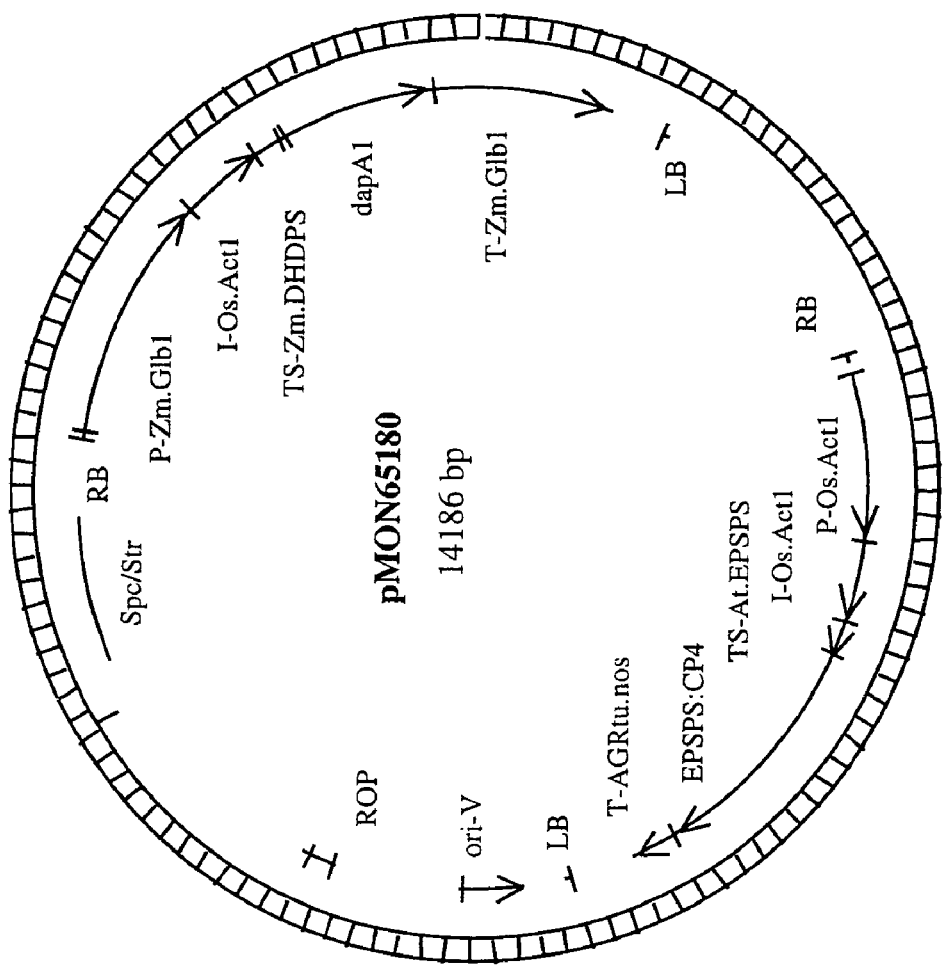
Figure 23:
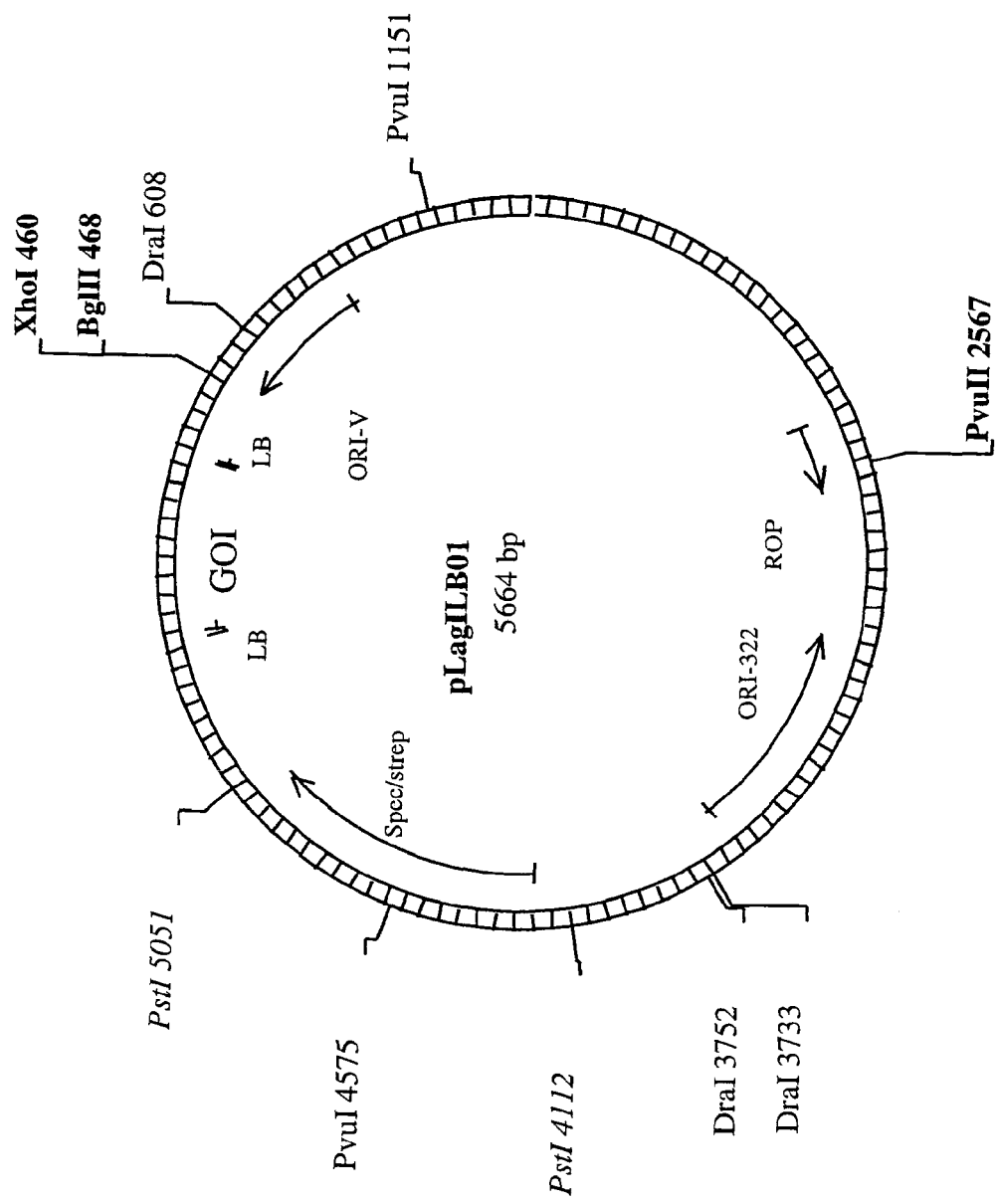

The constructs pMON65178 (FIG. 20), pMON65179 (FIG. 21), and pLagILB01 (FIG. 23) illustrate the orientations of the plant expression cassettes in the DNA constructs with respect to the border regions and the plasmid maintenance elements. The location of the positive selectable marker gene is in a region of the plasmid that contains the plasmid maintenance elements flanked by Ti plasmid border regions comprises a T-DNA, whereas the gene of interest is located in a region of the plasmid flanked by Ti plasmid border regions that does not contain any functional plasmid maintenance elements. These plasmids, and plasmids of similar design can be transferred into plants by an *Agrobacterium* mediated method. The resulting plants can be screened for the gene of interest and the selectable marker gene by methods that detect the presence of the transferred DNA in the plant genome. These methods include: DNA amplification methods, e.g., polymerase chain reaction (PCR); and DNA hybridization methods, e.g., DNA Southern Blot analysis. The R₀ Transgenic plants transformed with these constructs can be analyzed for the linkage of the T-DNAs by digesting isolated plant genomic DNA with restriction endonucleases that do not cut or cut rarely in any of the T-DNA segments, separating in an agarose gel by electrophoresis, transferring to a solid matrix and hybridizing with a labeled polynucleotide probe creating a Southern blot that is exposed to a media that detects the labeled probe. The polynucleotide probe is selected to be homologous to a DNA molecule specific to one of the T-DNAs. The Southern blot is then stripped of the first polynucleotide probe and hybridized with a second labeled probe that is specific to the other T-DNA and exposed to a media that detects the labeled probe. The resulting linkage Southern analysis can distinguish the linkage relationship of the gene of interest (GOI) and the positive selectable marker gene in the genome of the transgenic plant.

The constructs, pMON65178, pMON65179 and pMON65180 are transformed into corn cells by an *Agrobacterium* mediated method and fertile plants regenerated. In these constructs the GOI comprises a *Zea mays* Glb1 promoter, a rice actin 1 intron, a *Zea mays* DHDPS transit signal peptide, a dapA1 coding sequence (U.S. Pat. No. 6,329,574), and a *Zea mays* Glb1 transcriptional termination region. The selectable marker gene Table 3 illustrates the analysis of corn plants when analyzed by a polymerase chain reaction method for the GOI and linkage Southern blot analysis of R0 plants and PCR analysis of the R1 population and determination of the percent of fertile plants that have progeny segregating for the GOI and the selectable marker gene. This analysis indicates that pMON65178 (RB/GOI/LB::EPSPS:CP4) and pMON65179 (RB/GOI/RB::EPSPS:CP4) configurations are more effective than the more complex configuration of pMON65180 (RB/GOI/LB::RB/EPSPS:CP4/LB) for providing plants with the GOI, 88.8%, 88.9% and 67.7%, respectively. In addition, the efficiency of the genetic element configurations in the pMON65178 and pMON65179 constructs and the method for providing usable plants with unlinked GOI and selectable marker gene is as good as pMON65180 (67.7%×17.2%=11.6%) relative to pMON65179 (88.9%×12.4%=11%) and is better relative to pMON65178 (88.8%×33.7%=29.9%).

TABLE 4

Segregation analysis of 2 T-DNA containing corn plants

| pMON | Configuration | GOI | Unlinked event (R0 Southern) | Segregating marker free R1 |
|---|---|---|---|---|
| 65178 | RB/GOI/LB::CP4 | 88.8% (119/134) | 33.7% (34/101) | 100% (8/8) |
| 65179 | RB/GOI/RB::CP4 | 88.9% (232/261) | 12.4% (27/218) | 86% (12/14) |
| 65180 | RB/GOI/LB::RB/CP4/LB | 67.7% (176/260) | 17.2% (21/122) | |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim

We claim:

1. A DNA plasmid comprising in linked order a first *Agrobacterium* Ti plasmid right border region operably linked to a first DNA region comprising at least one transgene of agronomic interest operably linked to a second *Agrobacterium* Ti plasmid right border region operably linked to a second DNA region comprising an antibiotic positive plant selectable marker transgene or a herbicide positive selectable marker transgene and plasmid maintenance elements required for propagation in bacteria, wherein said second DNA region is also operably linked to said first *Agrobacterium* Ti plasmid right border region.

2. The DNA plasmid of claim 1, wherein said second DNA region further comprises a conditional lethal transgene.

3. The DNA plasmid of claim 2, wherein said conditional lethal transgene is selected from the group consisting of: phosphonate monoester hydrolase, glyphosate oxidoreductase, carboxy ester hydrolase, N-acetyl-L-ornithine deacetylase, P450 monooxygenase CPY105A1, and β-glucuronidase.

4. The DNA plasmid of claim 1, wherein said antibiotic positive plant selectable marker transgene provides tolerance to an antibiotic is selected from the group consisting of hygromycin, kanamycin, bleomycin, G418, streptomycin and spectinomycin.

5. The DNA plasmid of claim 1, wherein said herbicide selectable marker transgene provides tolerance to a herbicide selected from the group consisting of glyphosate, glufosinate, sulfonylureas, imidazolinones, bromoxynil, delapon, cyclohezanedione, a protoporphyrinogen oxidase inhibitor, and isoxaslutole herbicides.

6. The DNA plasmid of claim 1, wherein said transgene of agronomic interest provides an agronomic trait comprising herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress tolerance, increased digestibility, industrial enzyme production, pharmaceutical peptides and small molecule production, improved processing traits, proteins improved flavor, nitrogen fixation, hybrid seed production, reduced allergenicity, biopolymers, or biofuel production.

7. The DNA plasmid of claim 1, wherein said plasmid maintenance elements comprise at least one origin of replication and an antibiotic marker.

8. The DNA plasmid of claim 7, wherein said origin of replication is a pBR322 origin of replication and/or an oriV origin of replication from the RK2 plasmid.

9. The DNA plasmid of claim 7, wherein said antibiotic marker is an aad (Spc/Str) gene for bacterial spectinomycin/streptomycin resistance.

* * * * *